(12) United States Patent
Rikkerink et al.

(10) Patent No.: US 9,512,442 B2
(45) Date of Patent: Dec. 6, 2016

(54) RESISTANCE GENE AND USES THEREOF

(75) Inventors: Hendrikus Antonius Rikkerink, Waitakere (NZ); Elena Maria Hilario-Andrade, Auckland (NZ); Andrew Patrick Dare, North Shore (NZ); Susan Elizabeth Gardiner, Palmerston North (NZ); Minsoo Yoon, Auckland (NZ); Vincent Gerardus Maria Bus, Napier (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 449 days.

(21) Appl. No.: 12/740,318

(22) PCT Filed: Oct. 28, 2008

(86) PCT No.: PCT/NZ2008/000284
§ 371 (c)(1),
(2), (4) Date: Aug. 12, 2010

(87) PCT Pub. No.: WO2009/058030
PCT Pub. Date: May 7, 2009

(65) Prior Publication Data
US 2010/0306875 A1     Dec. 2, 2010

(30) Foreign Application Priority Data

Oct. 31, 2007  (NZ) .......................................... 563032
Sep. 22, 2008  (NZ) .......................................... 571416

(51) Int. Cl.
*C12N 15/82*     (2006.01)
*C07K 14/415*    (2006.01)

(52) U.S. Cl.
CPC ......... *C12N 15/8282* (2013.01); *C07K 14/415* (2013.01)

(58) Field of Classification Search
None
See application file for complete search history.

(56) References Cited

U.S. PATENT DOCUMENTS

| | | |
|---|---|---|
| 4,795,855 A | 1/1989 | Fillatti et al. |
| 5,004,863 A | 4/1991 | Umbeck |
| 5,159,135 A | 10/1992 | Umbeck |
| 5,177,010 A | 1/1993 | Goldman et al. |
| 5,187,073 A | 2/1993 | Goldman et al. |
| 5,188,958 A | 2/1993 | Moloney et al. |
| 5,416,011 A | 5/1995 | Hinchee et al. |
| 5,463,174 A | 10/1995 | Moloney et al. |
| 5,563,055 A | 10/1996 | Townsend et al. |
| 5,569,834 A | 10/1996 | Hinchee et al. |
| 5,591,616 A | 1/1997 | Hiei et al. |
| 5,750,871 A | 5/1998 | Moloney et al. |
| 5,792,935 A | 8/1998 | Arntzen et al. |
| 5,824,877 A | 10/1998 | Hinchee et al. |
| 5,846,797 A | 12/1998 | Strickland |
| 5,952,543 A | 9/1999 | Firoozabady et al. |
| 5,968,830 A | 10/1999 | Dan et al. |
| 5,981,840 A | 11/1999 | Zhao et al. |
| 6,020,539 A | 2/2000 | Goldman et al. |
| 6,037,522 A | 3/2000 | Dong et al. |
| 6,074,877 A | 6/2000 | D'Halluin et al. |

FOREIGN PATENT DOCUMENTS

| | | |
|---|---|---|
| WO | 02/00894 | 1/2002 |
| WO | 2009/058030 | 5/2009 |

OTHER PUBLICATIONS

Gardiner et al. 2003. Candidate resistance genes from an EST database prove a rich source of markers for major genes conferring resistance to important apple pests and diseases. Acta Hort. Proc. XXVI IHC. 622:141-151.*
Gassmann et al 1999. The Arabidopsis RPS4 bacterial-resistance gene is a member of the TIR-NBS-LRR family of disease-resistance genes. Plant J. 20(3):265-277.*
Guo et al. 2004. Protein tolerance to random amino acid change. PNAS. 101(25):9205-9210.*
Halterman et al. 2001. The MLA6 coiled-coil, NBS-LRR protein confers AvrMla6-dependent resistance specificity to Blumeria graminis f. sp. *hordei* in barley and wheat. Plant J. 25(3):335-348.*
Moffett et al. 2002. Interaction between domains of a plant NBS-LRR protein in disease resistance-related cell death. EMBO J. 21(17):4511-4519.*
Caffier et al 2005, Plant Pathology 54: 116-124.*
Xu et al 2002, Genetics 162: 1995-2006.*
Afunian, M.R. (Jan. 5, 2004) NCBI Nucleotide Accession No. AJ581791.1, "Pyrus communis partial gene for putative nucleotide binding site leucine-rich repeat disease resistance protein, clone RGA04," 3 pages.
Buell et al. (Feb. 7, 2003) NCBI Nucleotide Accession No. AAO37954.1, "putative resistance complex protein [Oryza sativa Japonica Group]," 4 pp.
Rikkerink et al. (Jun. 19, 2006) NCBI Nucleotide Accession No. DQ644205.1, "*Malus X domestica* clone ABFA005053CT putative NBS-LRR disease resistance protein gene, partial cds," 1 pp.
Sasaki et al. (Feb. 16, 2008) NCBI Nucleotide Accession No. BAD52970.1, "unknown protein [Oryza sativa Japonica Group]," 3 pp.

(Continued)

*Primary Examiner* — David H Kruse
(74) *Attorney, Agent, or Firm* — Lathrop & Gage LLP

(57) ABSTRACT

The invention provides methods for producing a plant with altered resistance to powdery mildew, the methods comprising transformation of a plant with a genetic construct including a polynucleotide encoding of a polypeptide with the amino acid sequence of SEQ ID NO: 1 or a variant of fragment thereof. The invention also provides isolated polypeptides, polynucleotides, constructs and vectors useful for producing a plant cell and plants transformed to contain and express the polypeptides, polynucleotides and constructs. The invention also provides plants produced by methods of the invention.

14 Claims, 17 Drawing Sheets

(56) References Cited

OTHER PUBLICATIONS

Figure 1:
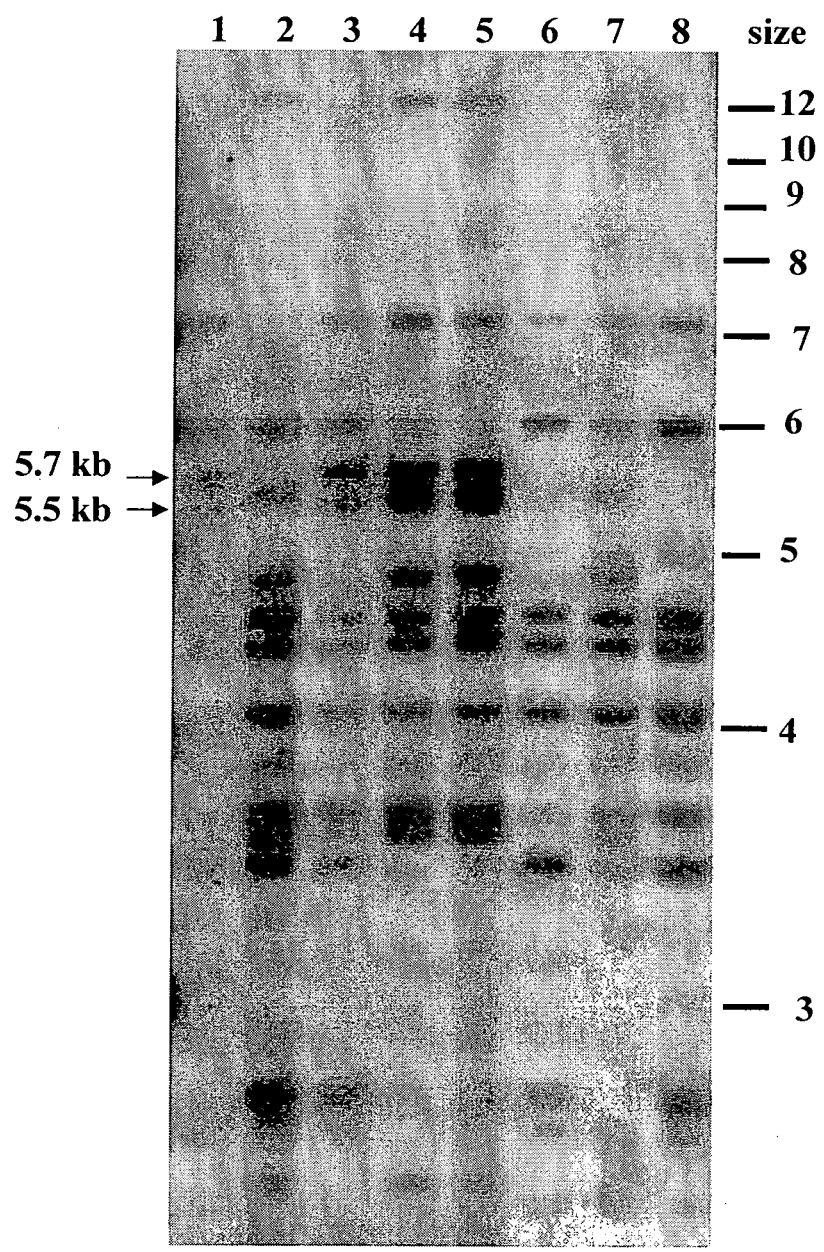

Sasaki et al. (Feb. 16, 2008) NCBI Nucleotide Accession No. AP003275.2, "Oryza sativa Japonica Group genomic DNA, chromosome 1, PAC clone: P0514H03," 62 pp.

Sato et al. (Nov. 16, 2011) NCBI Nucleotide Accession No. Q9LRR4.1, "RecName: Full=Putative disease resistance RPP13-like protein 1," 5 pp.

Simons et al. (Apr. 27, 1999) NCBI Nucleotide Accession No. AAD27815.1, "disease resistance protein I2 [Solanum lycopersicum]," 3 pp.

Yahiaoui et al. (Feb. 6, 2004) NCBI Nucleotide Accession No. AAQ96158.1, "powdery mildew resistance protein PM3b [Triticum aestivum]," 3 pp.

Yoshimura et al. (Feb. 13, 1999) NCBI Nucleotide Accession No. BAA25068.1, "XA1 [Oryza sativa (indica cultivar-group)]," 3 pp.

Search Report and Written Opinion, dated May 8, 2009, corresponding to International Application No. PCT/NZ2008/000284 (filed Oct. 28, 2008), parent of the present application, 8 pp.

Abbott et al. (2002) "Simultaneous Suppression of Multiple Genes by Single Transgenes. Down-Regulation of Three Unrelated Lignin Biosynthetic Genes in Tobacco," Plant Physiol. 128(3):844-853.

Alam et al. (1999) "Transgenic insect-resistant maintainer line (IR68899B) for improvement of hybrid rice," Plant Cell Reports 18:572-575.

Altschul et al. (1997) "Gapped BLAST and PSI-BLAST: a new generation of protein database search programs," Nucleic Acids Res 25(17):3389-3402.

Baldi et al. (2004) "Cloning and linkage mapping of resistance gene homologues in apple," Theor Appl Genet 109:231-239.

Baxevanis, A.D. (2001) "The Molecular Biology Database Collection: an updated compilation of biological database resources," Nucleic Acids Research 29(1):1-10.

Belfanti et al. (2004) "The HcrVf2 gene from a wild apple confers scab resistance to a transgenic cultivated variety," PNAS 101(3): 886-890.

Bent et al. (1994) "RPS2 of Arabidopsis thaliana: a Leucine-Rich Repeat Class of Plant Disease Resistance Genes," Science Washington 265:1856-1860.

Birch, R.G. (1997) "Plant Transformation: Problems and Strategies for Practical Application," Ann Rev Plant Phys Plant Mol Biol 48:297-326.

Braun et al. (1991) "Amino-terminal leucine rich repeats in gonadotropin receptors determine hormone selectivity," EMBO J 10(7):1885-1890.

Brueggeman et al. (2002) "The barley stem rust-resistance gene Rpg1 is a novel disease-resistance gene with homology to receptor kinases," PNAS 99(14):9328-9333.

Buschges et al. (1997) "The Barley Mlo Gene: A Novel Control Element of Plant Pathogen Resistance," Cell Cambridge 88:695-705.

Caffier et al. (2007) "Development of apple powdery mildew on sources of resistance to Podosphaera leucotricha, exposed to an inoculum virulent against the major resistance gene PI-2," Plant Breeding 126:319-322.

Cai et al. (1997) "Positional Cloning of a Gene for Nematode Resistance in Sugar Beet," Science 275:832-834.

Chang et al. (1993) "A Simple and Efficient Method for Isolating RNA From Pine Trees," Plant Molecular Biology Reporter 11(2):113-116.

Dan et al. (2006) "MicroTom—a high-throughput model transformation system for functional genomics," Plant Cell Reports 25:432-441.

Dayton, D.F. (1977) "Genetic Immunity to Apple Incited by Podoshaera leucotricha," HortScience 12(3):225-226.

De Carvalho Niebel et al. (1995) "Post Transcriptional Cosuppression of β-1,3-Glucanase Genes Does Not Affect Accumulation of Transgene Nuclear mRNA," Plant Cell 7:347-358.

Drenkard et al. (2000) "A simple procedure for the analysis of single nucleotide polymorphisms facilitates map-based cloning in Arabidopsis," Plant Physiol 124:1483-1492.

Dunemann et al. (1998) "Identification of Molecular Markers for the Major Mildew Resistance Gene $Pl_2$ in Apple," Acta Horticulturae 484:411-416.

Dunemann et al. (2007) "Mapping of the Apple Powdery Mildew Resistance Gene PI1 and its Genetic Association with an NBS-LRR Candidate Resistance Gene," Plant Breeding 126:476-481.

Durel et al. (1998) "Utilization of pedigree information to estimate genetic parameters from large unbalanced data sets in apple," Theor. Appl Genet. 96:1077-1085.

Erdin et al. (published online Dec. 15, 2006) "Mapping of the apple scab-resistance resistance gene Vb," Genome 49:1238-1245.

Feng and Doolittle (1987) "Progressive Sequence Alignment as a Prerequisite to Correct Phylogenetic Trees," J. Mol. Evol. 25:351-360.

Fischer et al. (1994) "Breeding apple cultivars with multiple resistance," Progress in Temperate Fruit Breeding, pp. 43-48.

Folta et al. (published online Apr. 14, 2006) "Characterization of LF9, an octoploid strawberry genotype selected for rapid regeneration and transformation," Planta 224:1058-1067.

Fuchigami et al. (1987) "Degree Growth Stage Model and Rest-Breaking Mechnaisms in Temperate Woody Perennials," HortScience 22(5):836-845.

Gallott et al. (1985) "Resistance to Powdery Mildew From Some Small-Fruited Malus Cultivars," Hortscience 20(6):1085-1087.

Gardiner et al. (2003) "Candidate Resistance Genes from an EST Database Prove a Rich Source of Markers for Major Genes Conferring Resistance to Important Apple Pests and Disease," Acta Horticulturae 622:141-151.

Giesen et al. (1998) "A formula for thermal stability (Tm) prediction of PNA/DNA duplexes," Nucleic Acids Res. 26(21):5004-5006.

Gleave, A.P. (1992) "A versatile binary vector system with a T-DNA organizational structure conducive to efficient integration of cloned DNA into the plant genome," Plant Molecular Biology 20:1203-1207.

Gonzalez Padilla et al. (2003) "Early antibiotic selection and efficient rooting and acclimatization improve the production of transgenic plum plants (Prunus domestica L.)," Plant Cell Reports 22(1):38-45.

Graham et al. (1995) "Agrobacterium -Mediated Transformation of Soft Fruit Rubus, Ribes, and Fragaria," Methods Mol Biol. 44:129-33.

Gygax et al. (2004) "Molecular markers linked to the apple scab resistance gene Vbj derived from Malus baccata jackii," Theor Appl Genet 109:1702-1709.

Hellens et al. (2000) "pGreen: a versatile and flexible binary Ti vector for Agrobacterium -mediated plant transformation," Plant Mol Biol 42:819-832.

Hellens et al. (2005) "Transient expression vectors for functional genomics, quantification of promoter activity and RNA silencing in plants," Plant Methods 1:13.

Hemmat et al. (1998) "Molecular Markers for the Scab Resistance (Vf) Region in Apple," Journal of the American Society of Horticultural Science 123: 992-996.

Herrera-Estrella et al. (1983) "Expression of chimaeric genes transferred into plant cells using a Ti-plasmid-derived vector," Nature 303:209-213.

Horsch et al. (1985) "A Simple and General Method for Transferring Genes into Plants," Science 227:1229-1231 with correction of authorship.

Huang, X. (1994) "On Global Sequence Alignment. Computer Applications in the Biosciences," 10(3):227-235.

Janse et al. (1994) "Early selection for partial resistance to powdery mildew, Podosphaera leucotricha(Ell. et Ev.) Salm. in apple progenies," Euphytica 77:7-9.

Jeanmougin et al. (Oct. 1998) "Multiple sequence alignment with Clustal X," Trends Biochem Sci 23:403-405.

Jobling et al. (2003) "Immunomodulation of enzyme function in plants by single-domain antibody fragments," Nat. Biotechnol. 21(1):77-80.

Jones et al. (1998) "The effect of chimeric transgene architecture on co-ordinated gene silencing," Planta 204:499-505.

(56) References Cited

OTHER PUBLICATIONS

Jones et al. (1997) "The Role of Leucine-Rich Repeat Proteins in Plant Defences," Advances Bot Res incorporating Advances Plant Pathol 24:89-167.
Jones et al. (1994) "Isolation of the Tomato *Cf-9* Gene for Resistance to *Cladosporium fulvum* by Transposon Tagging," Science Washington 266:789-793.
Jouvenot et al. (2003) "Targeted Regulation of Imprinted Genes by Synthetic Zinc-Finger Transcription Factors," Gene Therapy 10:513-522.
Kawchuk et al. (2001) "Tomato *Ve* disease resistance genes encode cell surface-like receptors," PNAS 98(11):6511-6515.
Knight et al. (1968) "Sources of Field Immunity to Mildew (*Podosphaera leucotricha*) in Apple," Can J Genet Cytol. 10:294-298.
Korban et al. (1983) "Evaluation of *Malus* Germplasm for Resistance to Powdery Mildew," HortScience 18(2):219-220.
Krens et al. (1997) "Transgenic caraway, *Carum carvi* L.: a model species for metabolic engineering," Plant Cell Reports 17:39-43.
Krüger, J. (1995) "Breeding for Mildew Resistance in Apples at Ahrensburg: Sources and Stability," Gartenbauwissenschaft 60(6):269-275. (English summary).
Kumar et al. (1996) "Potato plants expressing antisense and sense S-adenosylmethionine decarboxylase (SAMDC) transgenes show altered levels of polyamines and ethylene: antisense plants display abnormal phenotypes," The Plant J. 9(2):147-158.
Lespinasse, Y. (1992) "Breeding Apple Tree: Aims and Methods," Proceedings of the Joint Conference of the EAPR Breeding & Varietal Assessment Section and the EUCARPIA Potato Section France: Jan. 12-17, 1992, pp. 103-110.
Li et al. (1996) "Genetic transformation of cassava (*Manihot esculenta* Crantz)," Nature Biotechnology 14:736-740.
Li et al. (2001) "A fast neutron deletion mutagenesis-based reverse genetics system for plants," The Plant Journal 27(3):235-242.
Li et al. (2003) "Transgenic rose lines harboring an antimicrobial protein gene, *Ace-AMP1*, demonstrate enhanced resistance to powdery mildew (*Sphaerotheca pannosa*)," Planta 218(2):226-232.
Liu et al. (Sep. 2007) "Recent Progress in Elucidating the Structure, Function and Evolution of Disease Resistance Genes in Plants," J Genet Genom 34(9):765-776.
Lupas et al. (1991) "Predicting Coiled Coils from Protein Sequences," Science 252:1162-1164.
Markussen et al. (1995) "Identification of PCR-based markers linked to the powdery-mildew-resistance gene $Pl_1$ from *Malus robusta* in cultivated apple," Plant Breeding 114:530-534.
Martin et al. (1994) "A Member of the Tomato *Pto* Gene Family Confers Sensitivity to Fenthion Resulting in Rapid Cell Death," The Plant Cell 6:1543-1552.
Matsuda et al. (2005) "Development of an *Agrobacterium*-mediated transformation method for pear (*Pyrus communis* L.) with leaf-section and axillary shoot-meristem explants," Plant Cell Reports 24(1):45-51.
McIntyre et al. (1996) "Strategies for the suppression of peroxidase gene expression in tobacco. I. Designing efficient ribozymes," Transgenic Research 5:257-262.
Michelmore et al. (1987) "Transformation of lettuce (*Lactuca sativa*) mediated by *Agrobacterium tumefaciens*," Plant Cell Reports 6:439-442.
Napoli et al. (1990) "Introduction of a Chimeric Chalcone Synthase Gene into Petunia Results in Reversible Co-Suppression of Homologous Genes *in trans*," The Plant Cell 2:279-289.
Needleman et al. (1970) "A General Method Applicable to the Search for Similarities in the Amino Acid Sequence of Two Proteins," J. Mol. Biol. 48:443-453.
Nicholas et al. (1997) "Gene Doc: Analysis and Visualization of Genetic Variation," EMBNET.news 4:1-4.
Nielsen et al. (Dec. 6, 1991) "Sequence-Selective Recognition of DNA by Strand Displacement with a Thymine-Substituted Polyamide," Science 254(5037):1497-1500.

Niu et al. (1998) "Transgenic peppermint (*Mentha* x *piperita* L.) plants obtained by cocultivation with *Agrobacterium tumefaciens*," Plant Cell Reports 17:165-171.
Notredame et al. (2000) "T-Coffee: A Novel Method for Fast and Accurate Multiple Sequence Alignment," J. Mol. Biol. 302:205-217.
Oosumi et al. (published online Dec. 1, 2005) "High-efficiency transformation of the diploid strawberry (*Fragaria vesca*) for functional genomics," Planta 223(6):1219-1230, published online Dec. 1, 2005.
Ortiz et al. (1996) "Hygromycin resistance as an efficient selectable marker for wheat stable transformation," Plant Cell Reports 15:877-881.
Pena et al. (1995) "High efficiency *Agrobacterium*-mediated transformation and regeneration of citrus," Plant Science 104:183-191.
Perrière et a. (1996) "WWW-Query: An on-line retrieval system for biological sequence banks," Biochimie 78:364-369.
Ramesh et al. (2006) "Improved methods in *Agrobacterium*-mediated transformation of almond using positive (mannose/*pmi*) or negative (kanamycin resistance) selection-based protocols," Plant Cell Reports 25(8):821-828, published online Mar. 14, 2006.
Rice et al. (Jun. 2000) EMBOSS: The European Molecular Biology Open Software Suite, Trends in Genetics 16(6):276-277.
Riely et al. (2001) "Ancient origin of pathogen recognition specificity conferred by the tomato disease resistance gene *Pto*," PNAS 98(4):2059-2064.
Roberts et al. (1993) "Molecular differentiation in the extrahaustorial membrane of pea powdery mildew haustoria at early and late stages of development," Phys and Mol Plant Pathology 43:147-160.
Rosebrock et al. (Jul. 19, 2007) "A bacterial E3 ubiquitin ligase targets a host protein kinase to disrupt plant immunity," Nature (London) 448(7151):370-374.
Schrott, M. (1995) "Selectable Marker and Reporter Genes," In: Gene Transfer to Plants (Potrykus, T., Spangenberg. Eds) Springer Verlag. Berline, pp. 325-336.
Simons et al. (1998) "Dissection of the Fusarium *I2* Gene Cluster in Tomato Reveals Six Homologs and One Active Gene Copy," Plant Cell 10:1055-1068.
Song et al. (1995) "A Receptor Kinase-Like Protein Encoded by the Rice Disease Resistance Gene, *Xa21*," Science 270(5243):1804-1806.
Song et al. (2006) "Transformation of Montmorency sour cherry (*Prunus cerasus* L.) and Gisela 6 (*P. cerasus* x *P. canescens*) cherry rootstock mediated by *Agrobacterium tumefaciens*," Plant Cell Reports 25(2):117-123, published online Dec. 21, 2005.
Tatusova et al. (1999) "BLAST 2 Sequences, a New Tool for Comparing Protein and Nucleotide Sequences", FEMS Microbiol Lett. 174:247-250.
Thompson et al. (1994) "CLUSTAL W: improving the sensitivity of progressive multiple sequence alignment through sequence weighting, position-specific gap penalties and weight matrix choice," Nucleic Acids Research 22:4673-4680.
Thompson et al. (1997) "The Clustal_X windows interface: flexible strategies for multiple sequence alignment aided by quality analysis tools," Nucleic Acids Research 25(24):4876-4882.
Till et al. (2003) "High-throughput TILLING for functional genomics," Methods Mol Biol 236:205-220. (Abstract only).
Visser et al. (1979) "Resistance to Powdery Mildew (*Podosphaera leucotricha*) of apple seedlings growing under glasshouse and nursery conditions," Proc Eucarpia—Fruit Section, Meeting of Fruit Tree Breeding, Angers, pp. 111-120.
Wang et al. (2006) "Transformation of *Actinidia eriantha*: A potential species for functional genomics studies in *Actinidia*," Plant Cell Reports 25(5):425-431, published online Jan. 11, 2006.
Wheeler et al. (2001) "Database Resources of the National Center for Biotechnology Information," Nucleic Acids Research 29(1):11-16.
Whitham et al. (1994) "The Product of the Tobacco Mosaic Virus Resistance Gene *N*: Similarity to Toll and the Interleukin-1 Receptor," Cell 78:1101-1115.
Yahiaoui et al. (2004) "Genome analysis at different ploidy levels allows cloning of the powdery mildew resistance gene *Pm3b* from hexaploid wheat," Plant Journal 37:528-538.

(56) References Cited

OTHER PUBLICATIONS

Yahiaoui et al. (published online Jun. 1, 2006) "Rapid generation of new powdery mildew resistance genes after wheat domestication," The Plant Journal 47:85-98.
Yao et al. (1995) "Regeneration of transgenic plants from the commercial apple cultivar Royal Gala," Plant Cell Reports 14:407-412.
Yoshimura et al. (1998) "Expression of *Xa1*, a bacterial blight-resistance gene in rice, is induced by bacterial inoculation," PNAS 95:1663-1668.
Zhang et al. (accessible online Oct. 10, 2006) "Differential expression within the LOX gene family in ripening kiwifruit," J. Exp. Bot. 57(14):3825-3836.
Anderson (1993), Science, 259:1684-1687.
Azhaguvel et al. (2010), "Fundamentals of Physical Mapping" in *Principles and Practices of Plant Genomics*, vol. 3, pp. 24-62.
Newcomb (2006), Plant Phys., 141:147.
She (2003), BioTeach Journal 1:69-74.
Stein and Graner (2004), "Map-based gene isolation in cereal genomes" in *Cereal Genomics*, pp. 331-360.
Stein et al. (2000), Proc. Nat. Acad. Sci. 97:13436.
Velasco et al. (2010), Nat. Genet. 42:8331.

\* cited by examiner

```
   1 CTAGTTCTAGGATGATGTTAGAGAGACTATATATATATATATATATTTTTTTTTTTTAAG   60
  61 AAATGATATTATCTATACTAAAGAAAATTGATGAGTTCAGCGTCACAAAGTTATTAATAA  120
 121 TGTTGTTCAAATTTATATTTGGTAAAAAATCAAACTTAAAGAGTCTACTTTTAAAAAGGT  180
 181 ATGCTTATAAAATATATGAACTGACAGAAAGTTTGTAACATCTCATATCGTCTAGGGGAG  240
 241 TGGATCATCTATGTCTTATATCTATATTTTCATCTCTACCTAGCACGAGACATTTTGGGA  300
 301 GCTTACTGGTTTCGGGTTCCATCGAAACTCAGCGAGTTCGCTCGAGAGCAATCTCATGAT  360
 361 ACGTAGCACGATATTGCCTAAAACGAATAATGTCATGCTATGACGAAATCGAGACTATAT  420
 421 GTGATGGGTCCGATCCAAAATGTGACAAAATTCATGAAAACTCTTTTAAAAGAATCTTA   480
 481 TTAGCATTTTTCTTTTTCTAAACAGCATAAATATTTGGGGATTGATATTTACGAGCGTGT  540
 541 CGGAAGCAGCCGAATCGAAGTCACGAGATACGAAAAGAGTAGGCGTGGGCCGGAATGAAC  600
 601 GGATATTATGCATTTGCTGAGTCGATTCCACGACATGCAGAGTCAGATACACGTAGAAGC  660
 661 CGTCCGTTGTGGTCCCACATCTTAATTAATTAATTTCCATTTGTAGTTGGGTAGGTTTAA  720
 721 AGGATAAATTAGGATTATCACGCTCACAAAATAACATGATCAGCATTGCAAGGGAATGTT  780
 781 GCTCAGTTGTTTACGAGTCACCTTTGCACCCGAAGTTTCATGTTTGGTTCGCCATCTCCA  840
 841 AAATCGATCGCATAAAGGAAAAAAGAAATTGTAGCAAGTCTCTCAATTAAAAATTCATGA  900
 901 TCATTTGTCTCTTAATTTCCCAAAACGTGCGGCTATAGTTATTTTTGTCAACTTTATCAT  960
 961 AACTTTTGTCAAAACAAGTTAAGTTGAAAAAAACATTGCTATAATTGTATTAAAGTTAAG 1020
1021 ATATCATTGTTTCAATTAGATTAAAATTGAGAAACTATTTTACAATTTTCTCATTTAGT  1080
1081 TTTCCATATTCGCTTCTTGATTCGGCCTCATGTGCCTAGCACGTGACTCATTTTGACGAA 1140
1141 AATTTTAGCGGTGTTGACGAAATGGACTTTAGCTGCACATTTTAATGAGTTAAGAGACCA 1200
1201 ATTATCATGAATTTTTAATTAAGAGATCATTATTCTAATTTGATTAAAATTGAGAGATCA 1260
1261 TTGACACAATTTCTCCAAATGAAAAAAAAAACAGCAATAACCGTGTAGAACATAGGAGATA 1320
1321 AGAAAGCAATCAAATGATAAAACAATATGACCCCACGAAAAATAAAAAGAGAGGAAAAAG 1380
1381 AGGAGTCTAACTCTCCTTTTGGGCAGAAGGAAGAAGACTTCGTTATGGTCTTTCAACACC 1440
1441 TAATTATCTCAGCAAATTGAAGAGCTCTAAAGTAGTCTAGATCTGTTGATCTTAATGATC 1500
1501 TATGGAAACAAGTCCCTTCATCTTCATCATCTGAAAACTCCAACGCAGTAAGTTCCT    1560
1561 CTTGCAACTATACATGCCAAATCCATTATTTATTTATTTCATTTTTCTTCAAGTTTGTAT 1620
1621 GCTTAATTAATTATTTTATCAATAACCATCTATATAATCTGTGCACTTTTCAGGCTTAGT 1680
1681 TATTCCATCGTTCAGTCTGGATTTGTTGATCATAAGTGCAAACAAGTGCCCTCATGACCT 1740
1741 GATTGACTCCCATGAAACTGCTTCTTGCTACAGATCATGTCCAATATTCGTGCAAGTTCG 1800
1801 AGTCTTGAAACGTAGGATTGCAAGGTAATCCCAAAGCTGCCCATTTGTTTGTTCAACATG 1860
1861 TTAAAATTTAAGAAAAATAACCATTTATTTGTTTAACATGTTAAAATTTAAGAAAATAAT 1920
1921 GTATACTAATACATGATTTTTGCAATCATATATGATATGTTTTATTATGCTTTATTATTT 1980
1981 AAAGAGTAATGCTAGAAAAACTACATATTTATACTATATTAGTGTATCATCTCATATGGC 2040
2041 AAGTGGTGGACACAATCAATATCCTGTGAGATAAATTCATAAATTGACGTTACGTGTATA 2100
2101 CCTCACTTGCCACATTAGATGGTACATAAATGTGACACAAAATATGTGATCTTCCCAAC  2160
2161 ATTTTCCTATTAAGTAATATTATGTGGTGTGTTTATTGTGCTTTATACATACAATATCA  2220
2221 AGTTTTTTTATTTTTTATTGAAACATATAATATCAAGTTATTAGATTATTTGGTAGTAC  2280
2281 TATATTAGGGATTGTATACCTGGCGATACGGTTATGATGTTGGCAACCTTGATCTGAATG 2340
2341 CGTCCTGTTGCCTGCCATCTCTAGTCCCAAATTGTCACCTCTAGAAATGTTTACTAGGAG 2400
2401 TCCATTAATTGATTATTTCACTTTTACTATAAATTTGTATATGATTGCGCATGCATCAAT 2460
2461 AATTAGTTCTCATCATTTTAATTGGTGCAGTTGTGACTATTCTGAGTCTCGACAGATCA  2520
2521 AGCTTCCAAATTTCCAAGGAACTAGTATTTGACTGTTGATCTTCCCTTCGTTGAGTCTGT 2580
2581 ATTTGTTGATCACAAGCAGAGTTAGATTTGAACTTCCATGTAAGTTCTTATTATTTCTTT 2640
2641 GAATAAATACATTGCATTGCTTGCACATTTATTTGAACCACTTTATTTCATTTGTTTCTTC 2700
2701 ACTTAATTTGTACACATTCTGCACCTCAATATTGCTCAAGAGCGATTCGGTCTTTCTTGA 2760

2761 CTGCTTGGAGTAATCCTCGCTCTTAATATGGCACTGGGAGAGGTTTTCTTGCGGCGTTT  2820
   1                                  M  A  L  G  E  V  F  L  A  A  F    11
2821 CTACAGTTGCTGCTCGACAGGTTGACCCCTCGCGAGATTCTTGAGTACTTGGGAAATTTC 2880
  12  L  Q  L  L  L  D  R  L  T  P  R  E  I  L  E  Y  L  G  N  F   31
2881 CGGGGCGTCGGACAGAAGCTGGAGAAGTGGAGGACCACGTTGTCTACAATGGGAGCGGTG 2940
  32  R  G  V  G  Q  K  L  E  K  W  R  T  T  L  S  T  I  G  A  V   51
2941 CTGAGCGACGCTGAGGAAAGGCAACTGACTGAAGGTGGTGTGAAACTGTGGCTGGATGAT 3000
  52  L  S  D  A  E  E  R  Q  L  T  E  G  G  V  K  L  W  L  D  D   71
3001 CTCAGAGACCTGGCCTATGATATCGAAGACATGTTGGACAAATTTGCCGTTAAAATGTTG 3060
  72  L  R  D  L  A  Y  D  I  E  D  M  L  D  K  F  A  V  K  M  L   91
3061 AAGCCATGATAGAGGGATGTGATCAAGCCAGCACAAGCAGGAAGGTACGAGATCATTT   3120
  92  K  R  M  I  E  G  C  D  Q  A  S  T  S  R  K  V  R  R  S  F  111
3121 TATAAAGTTAAAATTGAGTTTTGATATGAACTCCGAAATGAAGAAGATTACGAAGCGGTTC 3180
 112  Y  K  V  K  L  S  F  D  M  N  S  E  M  K  K  I  T  K  R  L  131
3181 CAAGACATATCTGAACGGAAAGATAAGTTTGGCTTGAAAGATATTGGGACGTCTGCTAAG 3240
 132  Q  D  I  S  E  R  K  D  K  F  G  L  K  D  I  G  T  S  A  K  151
3241 GAATCGCGAAGTCTACCAAGTTCAGCAGTGTTAGATGAAAAGCTTGTTGTTGGAAGAGAT 3300
 152  E  S  R  S  L  P  S  S  D  V  L  D  E  K  L  V  V  G  R  D  171
3301 GGTGACAAATGGGAGATTATTGAATTGTTGTCAAAAAAAATACGAGCATACAGATGCCGTC 3360
```

FIG. 3

```
172  G  D  K  W  E  I  I  E  L  L  S  K  K  Y  E  H  T  D  A  V  191
3361 AATTTTGGTGTAGTTGCTATAGTTGGCATGCCCGGACTCGGGAAGACAACACTTGCTCAA 3420
192  N  F  G  V  V  A  I  V  G  M  P  G  V  G  K  T  T  L  A  Q  211
3421 CTTGTATTCAACCGCAAAGATGATGCCATGAAGGAGTTTGAGCTAAAGGTGTGGGTATGT 3480
212  L  V  F  N  R  K  D  D  A  M  K  E  F  E  L  K  V  W  V  C  231
3481 GTGTCTGATGACTTCGATGTTGAACGAGTGACGAAGGCAATTCTTGAATCAATCACATCC 3540
232  V  S  D  D  F  D  V  E  R  V  T  K  A  I  L  E  S  I  T  S  251
3541 CGACCCGTTCAAGTGCAGGAGTTTAGTCAAATTCAGCATGATTTGAGTGAGCAATTAAGA 3600
252  R  P  V  Q  V  Q  E  F  S  Q  I  Q  H  D  L  S  E  Q  L  R  271
3601 GGAAAAAGTTTTTAATCGTTTTAGATGATATCTGGAACAAAGATGACTCTGATCTATAC 3660
272  G  K  K  F  L  I  V  L  D  D  I  W  N  K  D  D  S  D  L  Y  291
3661 GATCTCTGGACAAGACTTCAATCCCCTTTTGGCATCGGAGCAGGAGGAAGTAAGATTATT 3720
292  D  L  W  T  R  L  Q  S  P  F  G  I  G  A  G  G  S  K  I  I  311
3721 GTGACAACCCGTGATGTGAATGTTGCAAAGATTATGGGAGCCACTGGAGTTCATAATTTG 3780
312  V  T  T  R  D  V  N  V  A  K  I  M  G  A  T  G  V  H  N  L  331
3781 GAGTGTATGGCAGATGATGATTGTTTGGAAATATTTGAGCGACATGCGTTCAGGGGAATT 3840
332  E  C  M  A  D  D  D  C  L  E  I  F  E  R  H  A  F  R  G  I  351
3841 AATACTGGAAAGCCGGTAAATTATGATTTAATTAAGACAAGAATTGTTGAAAAATGTCGT 3900
352  N  T  G  K  P  V  N  Y  D  L  I  K  T  R  I  V  E  K  C  R  371
3901 GGCTTACCATTAGCTGCAAGGACTCTCGGTGGTCTTTTACGTTGCAAAGAAAAGATGAG 3960
372  G  L  P  L  A  A  R  T  L  G  G  L  L  R  C  K  E  K  D  E  391
3961 TGGGGAGAAATATTGAACAACAAGTTATGGAATCTAGCCAGACAAGAGTGGCATTCTCCCC 4020
392  W  G  E  I  L  N  N  K  L  W  N  L  A  D  K  S  G  I  L  P  411
4021 GTACTAAAGTTGAGCTATCACTATCTTCCATCAAATTTGAAGAGGTGTTTTGCATATTGC 4080
412  V  L  K  L  S  Y  H  Y  L  P  S  N  L  K  R  C  F  A  Y  C  431
4081 TCAATACTTCCAAATGACTATGAATTTGGGGAGAAGCAGCTCATTCTTTTGTGGATGGCA 4140
432  S  I  L  P  N  D  Y  E  F  G  E  K  Q  L  I  L  L  W  M  A  451
4141 GAGGGTTTGATTCAACAAAATCCTGACGACAATAAACAAATAGAGGATTTGGGCCGCGAC 4200
452  E  G  L  I  Q  Q  N  P  D  D  N  K  Q  I  E  D  L  G  R  D  471
4201 TACTTTCGAGAGCTATTAGCAAGGTCGCTGTTTCAAGAATCAAGCAAAAACAATTCACGA 4260
472  Y  F  R  E  L  L  A  R  S  L  F  Q  E  S  S  K  N  N  S  R  491
4261 TATGTAATGCATGACCTCGTTAATGATTTAGCACAATGGGCAGCAGGTGAAATATGTTTT 4320
492  Y  V  M  H  D  L  V  N  D  L  A  Q  W  A  A  G  E  I  C  F  511
4321 AGATTGGAAGATAAGCAAGGTAATAACTTGCAAAGCAATTGCTTTCGAAGGGCTCGCCAT 4380
512  R  L  E  D  K  Q  G  N  N  L  Q  S  N  C  F  R  R  A  R  H  531
4381 TCGTCTTTCATTGCTGGTCGATTTGATGGAGTTATGAGATTTGAGGACTTTCCAAAAGTT 4440
532  S  S  F  I  A  G  R  F  D  G  V  M  R  F  E  D  F  P  K  V  551
4441 GAACGTTTGCGAACATTCCTGCCACTTTCACTTTCAGATTCAGGGGATGGGCCAAATAT 4500
552  E  R  L  R  T  F  L  P  L  S  L  S  D  S  R  G  W  A  K  Y  571
4501 TTGTCTCGTAAGGTTACTTTTGAGCTATTACCACAGTTGCAATACTTACGAGTGCTCTCT 4560
572  L  S  R  K  V  T  F  E  L  L  P  Q  L  Q  Y  L  R  V  L  S  591
4561 TTCAATGACTACACAATAACTGAGCTGCCAGACTCAATCGGTGATTTGAGGTTGTTACAG 4620
592  F  N  D  Y  T  I  T  E  L  P  D  S  I  G  D  L  R  L  L  Q  611
4621 TATCTTGACCTTTCCTATACACATATAGCCAGTTTGCCTAAATCAACAAGCACTCTTTAC 4680
612  Y  L  D  L  S  Y  T  H  I  A  S  L  P  K  S  T  S  T  L  Y  631
4681 CACTTGCAAACATTGATATTGGAAGGTTGTTCTCAATTGAAGTCATTGCCCGCGAACATG 4740
632  H  L  Q  T  L  I  L  E  G  C  S  Q  L  K  S  L  P  A  N  M  651
4741 AGTAATCTAATTAATTTGCGCCATCTCAACAACTCAGATGCATCTTCGTTGAAAGGAATG 4800
652  S  N  L  I  N  L  R  H  L  N  N  S  D  A  S  S  L  K  G  M  671
4801 CCTTCGCAACTAGGTCGATTGACAAATCTACAATCACTGCCTCTTTTTGTGGTGAGCGAA 4860
672  P  S  Q  L  G  R  L  T  N  L  Q  S  L  P  L  F  V  V  S  E  691
4861 GGAAGTGATCATTCAGGGATAAGAGAGATAGGGCCCCTATTGCATCTCCGAGGGACATTG 4920
692  G  S  D  H  S  G  I  R  E  I  G  P  L  L  H  L  R  G  T  L  711
4921 TGCCTCTTAGGATTGGAGAATGTGACTGATGTCGAGGATGCCAGGAGGGCCAACTTGAAA 4980
712  C  L  L  G  L  E  N  V  T  D  V  E  D  A  R  R  A  N  L  K  731
4981 TGCAAGGAGAGGCTTGATTCACTGGTCCTAAAATGGTATCATTCAAGCGACACGAGAGAA 5040
732  C  K  E  R  L  D  S  L  V  L  K  W  Y  H  S  S  D  T  R  E  751
5041 ACAGAATCCGCTGTGCTTGACATGTTACAGCCTCATACAAAGCTCAAGGAGCTCACCATC 5100
752  T  E  S  A  V  L  D  M  L  Q  P  H  T  K  L  K  E  L  T  I  771
5101 AAGGGTTATGCCAGAGAGGAATTTTCATCATGGGTTGGAGGTCCCTTGTTCTCTAATATG 5160
772  K  G  Y  A  R  E  E  F  S  S  W  V  G  G  P  L  F  S  N  M  791
5161 GTGCTTGTGCGCTTAGAGGAATGTAACAATTGTTTATCGTTGCCACCTCTCGGACAATTG 5220
792  V  L  V  R  L  E  E  C  N  N  C  L  S  L  P  P  L  G  Q  L  811
5221 CCTCGTCTCAAAGAGCTTTATATTGGAGGAATGAATGCAGTCGAAGTGTTGGTGCTGAG 5280
812  P  R  L  K  E  L  Y  I  G  G  M  N  A  V  E  S  V  G  A  E  831
5281 TTTTATGGTGAGTGTGTCATGCCTTTTCCGCTGTTACAGATTCTCGAGTTTGTGGATATG 5340
832  F  Y  G  E  C  V  M  P  F  P  L  L  E  I  L  E  F  V  D  M  851
```

FIG. 3 cont.

```
5341 CGGCATTGGAAGGTGTGGCTTCCTTTCCAACTGGATCACGGAAGTGGTGTTTTCCCTTTC 5400
 852  R  H  W  K  V  W  L  P  F  Q  L  D  H  G  S  G  V  F  P  F   871
5401 CTAAAAGGCTTTCAATCCAGGAATGTTCTAAGTTGGAAGGTAAACTGCCAGAGAAGCTT 5460
 872  L  K  R  L  S  I  Q  E  C  S  K  L  E  G  K  L  P  E  K  L   891
5461 GATTTGTTAGCCGAACTTGAAATTGTTAAATGTGAGGAATTGACGGTTTCGATTGCCAAC 5520
 892  D  L  L  A  E  L  E  I  V  K  C  E  E  L  T  V  S  I  A  N   911
5521 TACAAACAGCTTCGTCAGCTAAACATTGACGGTTGTAAAGTGTTGGAACATACAGCTGCT 5580
 912  Y  K  Q  L  R  Q  L  N  I  D  G  C  K  V  L  E  H  T  A  A   931
5581 AAGGTTGAGTTTGAGTTATTAGAGTCCTTGTGCATTTCAAACATTTCAGAGGTGATGTCT 5640
 932  K  V  E  F  E  L  L  E  S  L  C  I  S  N  I  S  E  V  M  S   951
5641 CGGCCAACAGGGGAATTGTTCAGGAAGGGACTAAGCAAGGTTAGAGATTTGAAGATCAAT 5700
 952  R  P  T  G  E  L  F  R  K  G  L  S  K  V  R  D  L  K  I  N   971
5701 GGATGTGAGAAGCTGACGTCTTCACTGAAGAATGAGGCTAGATTATTGCAGCGGTTGACT 5760
 972  G  C  E  K  L  T  S  S  L  K  N  E  A  R  L  L  Q  R  L  T   991
5761 TCTCTTGGCCGTTTGGAAATTAAAGACAACTCTCGTCTAGTTGAAGAATTGGGAGAAGAA 5820
 992  S  L  G  R  L  E  I  K  D  N  S  R  L  V  E  E  L  G  E  E  1011
5821 GCAGAGGAGTTGCTGCAATTGCAAATATTGGATTGCAAGCTTGAACTTCTAAAGTTAAGA 5880
1012  A  E  E  L  L  Q  L  Q  I  L  D  C  K  L  E  L  L  K  L  R  1031
5881 AAGTGCGAAAATCTTTTGAAGCTACCAAAAGGGTTAAATCAGCTGTCGTCTCTTCAAAAG 5940
1032  K  C  E  N  L  L  K  L  P  K  G  L  N  Q  L  S  S  L  Q  K  1051
5941 CTTCGCATAGTAGGATGTTCAAGTCTAGTTTCTTTTCCAGATGTGGTCTGCCACCTTCT  6000
1052  L  R  I  V  G  C  S  S  L  V  S  F  P  D  V  G  L  P  P  S  1071
6001 CTTAAAGACATCTGGATTGCAGAGTGCAATTCGTTGATATATTTTGCAAAATTCCAGATT 6060
1072  L  K  D  I  W  I  A  E  C  N  S  L  I  Y  F  A  K  F  Q  I  1091
6061 CCCCAAAATCTCAGAATAATACAGATAAGAGGGTGCAAAAGTTTGAAATCACTAGTAGAT 6120
1092  P  Q  N  L  R  I  I  Q  I  R  G  C  K  S  L  K  S  L  V  D  1111
6121 GAGGAGGAATGTGAACGACTGGGTTTAATAGCACCGAACGGGTTCTTCAGCGACAACACC 6180
1112  E  E  E  C  E  R  L  G  L  I  A  P  N  G  F  F  S  D  N  T  1131
6181 AATCACTGCCTTGAATCTATTTTGATCTGGAAGTGCCAAAATCGAAATCCTTACCGGAT  6240
1132  N  H  C  L  E  S  I  L  I  W  K  C  Q  N  L  K  S  L  P  D  1151
6241 GGCTTATGCCACCTCAGCAATCTTCAAACTCTAAGAATCGAATACTGTGGAAGTCTTGTT 6300
1152  G  L  C  H  L  S  N  L  Q  T  L  R  I  E  Y  C  G  S  L  V  1171
6301 TCCATCCCGAGACTGAGTGGGGGAGAAGACCCTCCAACCTGAGAGAGATCTGGATCCGA  6360
1172  S  I  P  R  L  S  G  G  R  R  P  S  N  L  R  E  I  W  I  R  1191
6361 GATTGCGAGAAATTGGAGGCGTTGCCCGAGACATGCACAATCTCAACTCTCTTGAGGAA  6420
1192  D  C  E  K  L  E  A  L  P  E  D  M  H  N  L  N  S  L  E  E  1211
6421 TTGAGGATCGACTACCGGGAAGGTTTGACTTTTCCTCCCAACCTAAAATCACTTGGAATT 6480
1212  L  R  I  D  Y  R  E  G  L  T  F  P  P  N  L  K  S  L  G  I  1231
6481 AGGAAGGTCAAGAGCTGTAAGTCATTGTGGGAGTTGGAGTGGGGGTTGCACAGACTCACC 6540
1232  R  K  V  K  S  C  K  S  L  W  E  L  E  W  G  L  H  R  L  T  1251
6541 TCTCTTAAAATCGGTGGTGAAGACCCGGATACGGTCGTTTCCACCCGACATGGTACGG  6600
1252  S  L  K  I  G  G  E  D  P  T  V  S  F  P  P  D  M  V  R  1271
6601 ATGGAGACGCTCTTCCCCAAATCTCTCACTAGCCTCTCAATAGATGGCTTCCCGAATTTG 6660
1272  M  E  T  L  F  P  K  S  L  T  S  L  S  I  D  G  F  P  N  L  1291
6661 AAGAAACTGAGCAGCAAGGGCTTTCAATTCCTCACCTCCCTTCAATCTCTTACACTCTTG 6720
1292  K  K  L  S  S  K  G  F  Q  F  L  T  S  L  Q  S  L  T  L  L  1311
6721 GATTGTCCAAAGCTAGCATCCATTCCAGAGGAGGGTCTGCCTCCTTCACTAGAGGAATTA 6780
1312  D  C  P  K  L  A  S  I  P  E  E  G  L  P  P  S  L  E  E  L  1331
6781 ATCATCGATGGGTGTCCAGTGCTAAAAGAGAGATGCCAACCAGGAAAAGGACGCTACTGG 6840
1332  I  I  D  G  C  P  V  L  K  E  R  C  Q  P  G  K  G  R  Y  W  1351
6841 CACAAAATATCCCACATCCCTTTCATAGAGATAGATTGGCACATAATTTGATGCAGATGG 6900
1352  H  K  I  S  H  I  P  F  I  E  I  D  W  H  I  I  *            1367
6901 TCCAGGTATCATCTGTCGAGGAATGTTTTAATATTAATATTATTATTATTATCTTTA     6960
6961 TTCTTTTTTTTTGGGTAATTAATCATGTTTTATTCTTGTAAAGTAAAGTAATCCACATAT 7020
7021 TTTGGTTTGGGTCAAGGTTTTGGGGGTTGAGGAGTGGCTGCTTTGGAGGTCTTCAATTG  7080
7081 GCGACAACCTGGATATTTCTCGGCCAACGTTTCTTCTCCCGGATTCCTATATTTTCTTTT 7140
7141 TTTATTTTTTTGGTAAACGATTGCTATGTTTGCTTGGCCCCTTTTCACTGATTTGTATTA 7200
7201 TAACTTTGTAAATCAGGCCACTTTCACCTAATGTTTATTTTATTTTAGCAAATTTTGAC  7260
7261 TTATGAGCTAGTTATCTTAATGCATCGAGAATAAGCAATCAACAAAAGAAATGGAAATGCA 7320
7321 AATGATGACCACTAAATGACTTCCTTTACCATAACTTGTCTTCCTGAAAGTAGATAATAT 7380
7381 GTGCCAACAAATTTTGGTCAATCAAATCCTTATACCAAGCCTTCGTCACTTATTCAAAAA 7440
7441 GTGCATTATTCATCTAATTAATATGTAATAAATTGGTGACGATTATACATTTTAACTGAG 7500
7501 TTCTAAGGAAAATTGAGGGTAGTAATACATCAGTACTAAAACGTGAATTTGTGAAAAACT  7560
7561 GGTTTGATTTATTCGTGGATTTTATGTGGGATAGTGATTGTGCAATTTTCCATTTTTTA  7620
7621 TTTGACCCTCAATTTTATTCCAAACGCAACAACACCTTCAGGGCTGACGCCGACTTAACG 7680
7681 GCGATCCGAATCATCTTTCCGTTCCGTCATTTTAAAATTATTTAGTAATCCTAAATTTCT 7740
7741 TCATCTAAACATAGTGTAACTCGTTAAGAAGACTCTCGAAGTCGAGAGAAAAGATGAGC  7800
7801 GACGCGTGGAAAATAGGGACACAAACGGAAAGAAAACAGAGAAGCGAGGGCAGTTCCGTC 7860
```

FIG. 3 cont.

```
7861  CGGACACTGGTGATCAACAGTACCGGGGGAAACTCACGTTTAGTATATATGATTTACAAG  7920
7921  CTTTATTTGGGACTGCCCGAATTTGATTCTTAAGCAATGTTTATTAAAGTGAGGTGATCT  7980
7981  GATAATGACCTGATTCATTAACAAGTTATGTTGTTTTATGTTGGGTTAATGGGTCCTGCA  8040
8041  AGACATTGCTTAATGTCTAAATTTGGCAAACAATATTTTGTCGAGTTCTTGATTCAACAA  8100
8101  TGACTCAACTTGTTAAAGGGTTCTTAATGAGTCCTAATAACGACTCGACTTGTTAACAGG  8160
8161  TTGACTAAAAACCTATTACTTTCATGTCGTTTTGTATCAAATGAACGAGTCGTGCAATAA  8220
8221  ATTGTCAGACCTAATGGGACCGTGCCAAACAATTGATCGTAGCACGATATTATCTGCTTT  8280
8281  AGGTCCTGACCACACCCTCACGGTTTTGTTTCTGATAACTCACACGAAAACTTCCCAGTG  8340
8341  GGTCATCCATCATGGGATTGCTCTCGCGCAATCTCGCTTAACTTCGAAGTTCCTATGAAA  8400
8401  TCTGAAGCCAGTGAGTTCCAAAAAGACCTTGTGCTAATTGGAGGTAGGAATGTACATATA  8460
8461  AGGCATAGAGGATCCACTCCCCTAG 8485
```

FIG. 3 cont.

```
CC region              *          20         *          40         *          60
MxdP12.1CC  : ----MA GE    AAF  Q  LD   PR---E  EYLGNFR  G  E W TT ST GA  S  :  53
AthaQ9LRR4  : -----MTG GE    AAF QA FQT  VSE------PFRSF  RRELN NL E  STA LT TA  I  :  54
LescI2CC    : MEIGLA GGA  SSA  N  FD  APNG--D NM  KHKDHVKL K  MT RG QI  S  :  58
OsatXA1CC   : ---MEE EAG  EGG RW AET LDNLDADK D  IRQIR AADTE  RAE EK DG A  :  57
TaesPM3bCC  : --MAER VT A GPL SK KD A S------Y D  VME    QHKI RK PA LD  T  :  54
OsatAAO379  : --MAEL AT V GPL C  KE A S----Y L E   VME    QHKI RK PA LD  A  :  54
OsatP0514H  : ----MATS I GPL A  NRQ  N----Y  Q  QELD   Q TI ERK PA LD   T  :  51
              6        6  6                                      1   6 6  V6
                        *          80         *         100         *         120
MxdP12.1CC  :    Q-LTEG    L DD   D A DIE    K AVKM   M EGCDQASTSRKVRR------ : 109
AthaQ9LRR4  :    Q-ITNPV EK    N    D V H E  A  DIAT    LN GAESSSSNRLRQ R--- : 110
LescI2CC    :    NKQ-ASNPS  D  N    DAVDS E  IE VNY E   LK EG--QHQNFSETSN--- : 112
OsatXA1CC   : AVKGRA-IGNRS ARS  GR  G L D  A   LD FR  QQQ EGGVTTRFEAEET GDG  : 116
TaesPM3bCC  :    QAMAQRE A A   Q      V  EXF  EK Y E   EAKKNGHYIKLGFD   ---- : 111
OsatAAO379  :    QAAKHRE A A   E   K A Q  VF  EK Y E   KAKANWQYKMLGMD   ---- : 111
OsatP0514H  :    QG-THRP  SA   KA  A A K    F  KY E   EAKRRGNHGNLSTS   ----  : 107
              d   e           w6  L4     y  a        d        L
                                        ---Coiled coil---
                        *         140         *         160         *         180
MxdP12.1CC  : -------------------------------------------------------SFYK  : 113
AthaQ9LRR4  : -------------------------------------------------------GRMS  : 114
LescI2CC    : -------------------------------------------------------QQVS  : 116
OsatXA1CC   : AEDEDDIPMDNTDVPEAVAAGSSKKRSKAWEHFTTIVEFTADGKDSKARCKYCHKDLCCTS : 176
TaesPM3bCC  : -------------------------------------------------------KLFP  : 115
OsatAAO379  : -------------------------------------------------------KLFP  : 115
OsatP0514H  : -------------------------------------------------------LAN-  : 110
```

FIG. 6A

```
                        *         200         *         220         *         240
MxdP12.1CC  : VKLSFDMNS-----E  TKR D SERK KE L ---DIGT AKES SLP  DV  EK : 165
AthaQ9LRR4  : LG F DGNSEHLET  E  TIP R AS R IL L ----ELTAMIPKQ -LP  S V ES : 170
LescI2CC    : DDFF NI D-----  EDT ET KD QE  GLL L ----EYFD IT LETRRP  S D ES : 168
OsatXA1CC   : KNGTSAL NH NVC  R   TSTD P NPSSAGE ASNATGNSVGR RM MDG  THHEAV : 236
TaesPM3bCC  : TH R AF YK G-R  CL  QA  V IA  QV  F YQP PPV  -KEW HTD-YVS  PQ : 172
OsatAAO379  : TH R VF YR G-N  M LNA  V ITE  A RF FRP PPM SMKW KTD KISEHSM : 174
OsatP0514H  : --  P VF YR S-K    SS  D VAD  A  F YRP MPT -KQW QTD-         SE : 165
                             6         g           r

*         260         *         280
MxdP12.1CC  : -----------L VG ---DG WE   EL SKKYEHT A NFG : 194
AthaQ9LRR4  : -----------E FG ---DD DE   RF  PENGKD G T-- : 197
LescI2CC    : -----------D FG ---SEIED   DR   GASGKK  T--- : 195
OsatXA1CC   : STHPWNKAELSNRIQCMTHQL EAVNE   R CR SS  QSRQGTP : 281
TaesPM3bCC  : -----------E AS SRHE  KN   G   DEA  A LT---- : 200
OsatAAO379  : -----------D AN SR EL QK   KS L  A NG LT---- : 202
OsatP0514H  : -----------N VS --  KE QH  VN L   DAS RNL  --- : 191
                          r             66   l
```

FIG. 6A cont.

FIG. 6A cont.

```
                    *         260         *         280         *         300
MxdP12.1NB  : HY SN         SL N  E GEKQ  L      E L  Q NPDDNKQ  D  RD  R  L : 283
AthaQ9LRR4  : YY  AH         S  N  GHA EKDK  L     E    Q TRS-SKN  EL NE   S  E : 281
LescI2NB    :  D  AH         S   P RKEQ  H   A SL  VKDE----IN D NQ  L  R : 276
OsatXA1NB   :  H SNP  VS   S     G S SKAQ   T      E SSE----K  QK WK LA  V : 287
TaesPM3bNB  : KD SH  VS     KIDVAK  Q      G SHKE--DS ET  QLI D  A : 275
OsatAAO379  :   C  Y       HVIDVEM   L    C    QQG---ECP IS KRI S  V : 272
OsatP0514H  :  D  Y        VIDVEM   L    D    SEEA--IRP TK KQI N  A : 270
              Lp   6   Cf  5C  6fPk        66  6W6A    6         2   G   f  EL
              --RNBS-D---            -----WMx-G
                    *         320         *         340         *         360
MxdP12.1NB  : A  L  ESSKNNSR----------          WAA EI FR EDKQGNN QSNCF : 332
AthaQ9LRR4  :   LL ---KTKTR-----------    NE   FAS EFSSKFED--GCK QVS-- : 323
LescI2NB    :  L  K PNPSKRNIEE------L       LASS L IR EESQGSH LEQ-- : 328
OsatXA1NB   : NSG L Q ESTRFSS---E-------Y       KVSQT YAT DGSECTE APS-- : 337
TaesPM3bNB  :    LD EKSKEDWEYY----SRTTCK       MSVME  VVATMEPSEIEWLP-- : 330
OsatAAO379  :     D KGIPFEFHDIKD-SKITAK        SSM K CAA DSESIGSEDFP-- : 329
OsatP0514H  :     D KEVPLHKDESGHSYRTICS        VSVIG E FT AEGHNYIEFLP-- : 328
              rs                            6HD16  d6A
                                            MHD------
                    *
MxdP12.1NB  : RRA  S FIAG : 343
AthaQ9LRR4  : ERT Y YLRD : 334
LescI2NB    : --C   YSIG : 337
OsatXA1NB   : --I   VT-  : 345
TaesPM3bNB  : DTA  F SC- : 340
OsatAAO379  : YSA  F SG- : 339
OsatP0514H  : NTV  F CS- : 338
              Rh1
```

FIG. 6A cont.

Figure 6B

| L | XXLXLXX | C/N Consensus | LRR |
|---|---|---|---|
| KVERLR | TFLPLSL | SDSRGWAKYLSRKVT | LRR 1 |
| FELLPQL | QYLRVLS | FNDYTITELPDS | LRR 2 |
| IGDLRLL | QYLDLSY | THIASLPKS | LRR 3 |
| TSTLYHL | QTLILEG | CSQLKS | LRR 4 |
| LPANMS | NLINLRH | LNNSDASSLKGMPSQ | LRR 5 |
| LGRLTNL | QSLPLFV | VSEGSDHSGIREIGP | LRR 6 |
| LLHLR | GTLCLLG | LENVTDVEDARRAN | LRR 7 |
| LKCKERL | DSLVLKW | YHSSDTRETESAVLDM | LRR 8 |
| LQPHTKL | KELTIKG | YAREEFSSWVGGP | LRR 9 |
| LFSNM | VLVRLEE | CNNCLSLPP | LRR 10 |
| LGQLPRL | KELYIGG | MNAVESVGAEFYG | LRR 11 |
| ECVMPF | PLLEILE | FVDMRHWKVWLPFQLDH | LRR 12 |
| GSGVFPFL | KRLSIQE | CSKLEGKLP | LRR 13 |
| EKLDLL | AELEIVK | CEELTVS | LRR 14 |
| IANYKQL | RQLNIDG | CKVLEHTAAK | LRR 15 |
| VEFELL | ESLCISN | ISEVMSRPGELF | LRR 16 |
| RKGLSKV | RDLKING | CEKLTSSLKNEAR | LRR 17 |
| LLQRLTSL | GRLEIKD | NSRLVEELGEEAEELLQ | LRR 18 |
| LQILDCKL | ELLKLRK | CENLLKLPK | LRR 19 |
| GLNQLSSL | QKLRIVG | CSSLVSFP | LRR 20 |
| DVGLPPSL | KDIWIAE | CNSLIYFAKF | LRR 21 |
| QIPQNL | RIIQIRG | CKSLKS | LRR 22 |
| LVDEEEC | ERLGLIA | PNGFF | LRR 23 |
| SDNTNHCL | ESILIWK | CQNLKSLPDG | LRR 24 |
| LCHLSNL | QTLRIEY | CGSLVSIPRLSG | LRR 25 |
| GRRPSNL | REIWIRD | CEKLEALPED | LRR 26 |
| MHNLNSL | EELRIDY | REGLTFP | LRR 27 |
| PNL | KSLGIRK | VKSCKSLWEL | LRR 28 |
| EWGLHRL | TSLKIGG | EDPDTVSFPPDMVRME | LRR 29 |
| TLFPKSL | TSLSIDG | FPNLKKLSSKG | LRR 30 |
| FQFLTSL | QSLTLLD | CPKLASIP | LRR 31 |
| EEGLPPSL | EELIIDG | CPVLKER | LRR 32 |

CQPGKGRYWHKISHIPFIEIDWHII

Figure 8
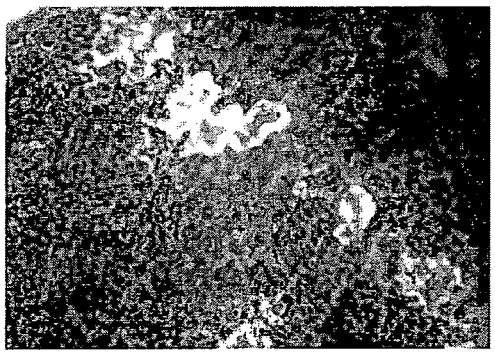
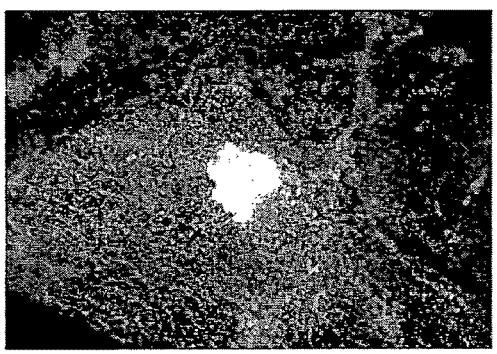
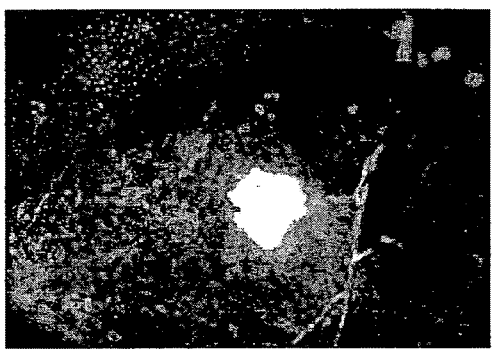
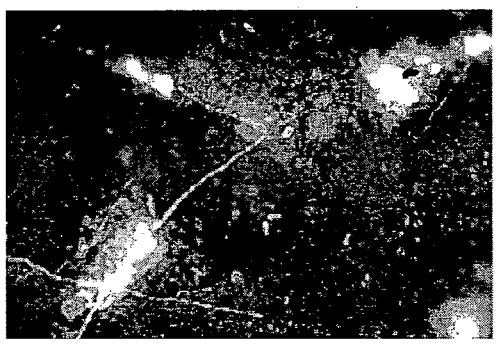
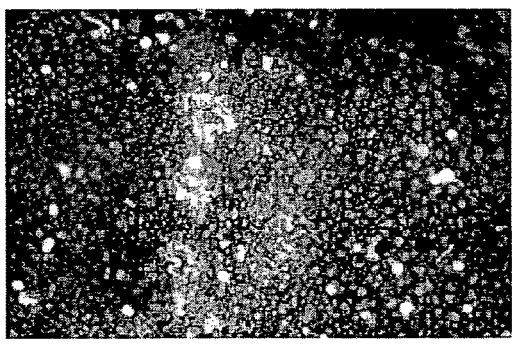

Figure 9
A
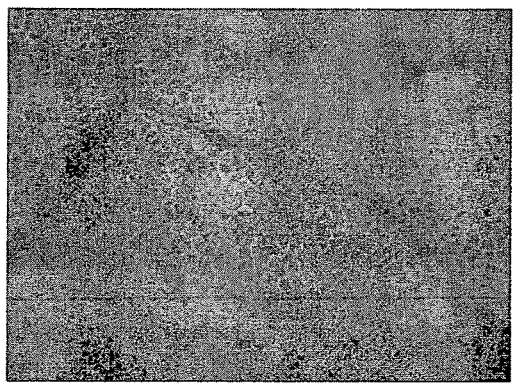
B
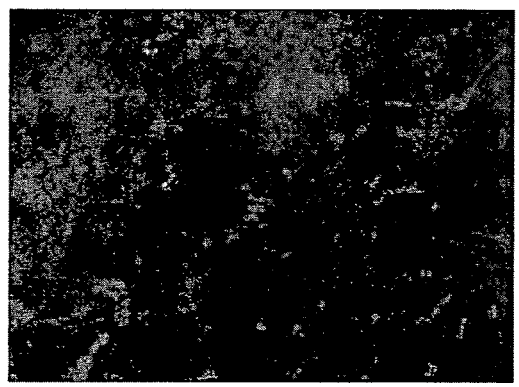
C
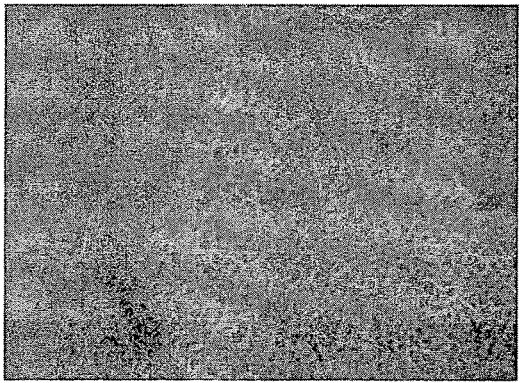

SEQUENCE LISTING

```
<160> NUMBER OF SEQ ID NOS: 35

<210> SEQ ID NO 1
<211> LENGTH: 1367
<212> TYPE: PRT
<213> ORGANISM: Malus zumi

<400> SEQUENCE: 1

Met Ala Leu Gly Glu Val Phe Leu Ala Ala Phe Leu Gln Leu Leu Leu
1               5                   10                  15

Asp Arg Leu Thr Pro Arg Glu Ile Leu Glu Tyr Leu Gly Asn Phe Arg
            20                  25                  30

Gly Val Gly Gln Lys Leu Glu Lys Trp Arg Thr Thr Leu Ser Thr Ile
        35                  40                  45

Gly Ala Val Leu Ser Asp Ala Glu Arg Gln Leu Thr Glu Gly Gly
    50                  55                  60

Val Lys Leu Trp Leu Asp Asp Leu Arg Asp Leu Ala Tyr Asp Ile Glu
65                  70                  75                  80

Asp Met Leu Asp Lys Phe Ala Val Lys Met Leu Lys Arg Met Ile Glu
                85                  90                  95

Gly Cys Asp Gln Ala Ser Thr Ser Arg Lys Val Arg Arg Ser Phe Tyr
            100                 105                 110

Lys Val Lys Leu Ser Phe Asp Met Asn Ser Glu Met Lys Lys Ile Thr
        115                 120                 125

Lys Arg Leu Gln Asp Ile Ser Glu Arg Lys Asp Lys Phe Gly Leu Lys
    130                 135                 140

Asp Ile Gly Thr Ser Ala Lys Glu Ser Arg Ser Leu Pro Ser Ser Asp
145                 150                 155                 160

Val Leu Asp Glu Lys Leu Val Val Gly Arg Asp Gly Asp Lys Trp Glu
                165                 170                 175

Ile Ile Glu Leu Leu Ser Lys Lys Tyr Glu His Thr Asp Ala Val Asn
            180                 185                 190

Phe Gly Val Val Ala Ile Val Gly Met Pro Gly Val Gly Lys Thr Thr
```

```
            195                 200                 205
Leu Ala Gln Leu Val Phe Asn Arg Lys Asp Ala Met Lys Glu Phe
210                 215                 220

Glu Leu Lys Val Trp Val Cys Val Ser Asp Asp Phe Asp Val Glu Arg
225                 230                 235                 240

Val Thr Lys Ala Ile Leu Glu Ser Ile Thr Ser Arg Pro Val Gln Val
                245                 250                 255

Gln Glu Phe Ser Gln Ile Gln His Asp Leu Ser Glu Gln Leu Arg Gly
                260                 265                 270

Lys Lys Phe Leu Ile Val Leu Asp Asp Ile Trp Asn Lys Asp Asp Ser
            275                 280                 285

Asp Leu Tyr Asp Leu Trp Thr Arg Leu Gln Ser Pro Phe Gly Ile Gly
        290                 295                 300

Ala Gly Gly Ser Lys Ile Ile Val Thr Thr Arg Asp Val Asn Val Ala
305                 310                 315                 320

Lys Ile Met Gly Ala Thr Gly Val His Asn Leu Glu Cys Met Ala Asp
                325                 330                 335

Asp Asp Cys Leu Glu Ile Phe Glu Arg His Ala Phe Arg Gly Ile Asn
            340                 345                 350

Thr Gly Lys Pro Val Asn Tyr Asp Leu Ile Lys Thr Arg Ile Val Glu
        355                 360                 365

Lys Cys Arg Gly Leu Pro Leu Ala Ala Arg Thr Leu Gly Gly Leu Leu
370                 375                 380

Arg Cys Lys Glu Lys Asp Glu Trp Gly Glu Ile Leu Asn Asn Lys Leu
385                 390                 395                 400

Trp Asn Leu Ala Asp Lys Ser Gly Ile Leu Pro Val Leu Lys Leu Ser
                405                 410                 415

Tyr His Tyr Leu Pro Ser Asn Leu Lys Arg Cys Phe Ala Tyr Cys Ser
            420                 425                 430

Ile Leu Pro Asn Asp Tyr Glu Phe Gly Glu Lys Gln Leu Ile Leu Leu
        435                 440                 445

Trp Met Ala Glu Gly Leu Ile Gln Gln Asn Pro Asp Asp Asn Lys Gln
450                 455                 460

Ile Glu Asp Leu Gly Arg Asp Tyr Phe Arg Glu Leu Leu Ala Arg Ser
465                 470                 475                 480

Leu Phe Gln Glu Ser Ser Lys Asn Asn Ser Arg Tyr Val Met His Asp
                485                 490                 495

Leu Val Asn Asp Leu Ala Gln Trp Ala Ala Gly Glu Ile Cys Phe Arg
            500                 505                 510

Leu Glu Asp Lys Gln Gly Asn Asn Leu Gln Ser Asn Cys Phe Arg Arg
        515                 520                 525

Ala Arg His Ser Ser Phe Ile Ala Gly Arg Phe Asp Gly Val Met Arg
530                 535                 540

Phe Glu Asp Phe Pro Lys Val Glu Arg Leu Arg Thr Phe Leu Pro Leu
545                 550                 555                 560

Ser Leu Ser Asp Ser Arg Gly Trp Ala Lys Tyr Leu Ser Arg Lys Val
                565                 570                 575

Thr Phe Glu Leu Leu Pro Gln Leu Gln Tyr Leu Arg Val Leu Ser Phe
            580                 585                 590

Asn Asp Tyr Thr Ile Thr Glu Leu Pro Asp Ser Ile Gly Asp Leu Arg
        595                 600                 605

Leu Leu Gln Tyr Leu Asp Leu Ser Tyr Thr His Ile Ala Ser Leu Pro
610                 615                 620
```

```
Lys Ser Thr Ser Thr Leu Tyr His Leu Gln Thr Leu Ile Leu Glu Gly
625                 630                 635                 640

Cys Ser Gln Leu Lys Ser Leu Pro Ala Asn Met Ser Asn Leu Ile Asn
                645                 650                 655

Leu Arg His Leu Asn Asn Ser Asp Ala Ser Ser Leu Lys Gly Met Pro
            660                 665                 670

Ser Gln Leu Gly Arg Leu Thr Asn Leu Gln Ser Leu Pro Leu Phe Val
        675                 680                 685

Val Ser Glu Gly Ser Asp His Ser Gly Ile Arg Glu Ile Gly Pro Leu
    690                 695                 700

Leu His Leu Arg Gly Thr Leu Cys Leu Leu Gly Leu Glu Asn Val Thr
705                 710                 715                 720

Asp Val Glu Asp Ala Arg Arg Ala Asn Leu Lys Cys Lys Glu Arg Leu
                725                 730                 735

Asp Ser Leu Val Leu Lys Trp Tyr His Ser Ser Asp Thr Arg Glu Thr
            740                 745                 750

Glu Ser Ala Val Leu Asp Met Leu Gln Pro His Thr Lys Leu Lys Glu
        755                 760                 765

Leu Thr Ile Lys Gly Tyr Ala Arg Glu Phe Ser Ser Trp Val Gly
    770                 775                 780

Gly Pro Leu Phe Ser Asn Met Val Leu Val Arg Leu Glu Glu Cys Asn
785                 790                 795                 800

Asn Cys Leu Ser Leu Pro Pro Leu Gly Gln Leu Pro Arg Leu Lys Glu
                805                 810                 815

Leu Tyr Ile Gly Gly Met Asn Ala Val Glu Ser Val Gly Ala Glu Phe
            820                 825                 830

Tyr Gly Glu Cys Val Met Pro Phe Pro Leu Leu Glu Ile Leu Glu Phe
        835                 840                 845

Val Asp Met Arg His Trp Lys Val Trp Leu Pro Phe Gln Leu Asp His
    850                 855                 860

Gly Ser Gly Val Phe Pro Phe Leu Lys Arg Leu Ser Ile Gln Glu Cys
865                 870                 875                 880

Ser Lys Leu Glu Gly Lys Leu Pro Glu Lys Leu Asp Leu Leu Ala Glu
                885                 890                 895

Leu Glu Ile Val Lys Cys Glu Glu Leu Thr Val Ser Ile Ala Asn Tyr
            900                 905                 910

Lys Gln Leu Arg Gln Leu Asn Ile Asp Gly Cys Lys Val Leu Glu His
        915                 920                 925

Thr Ala Ala Lys Val Glu Phe Glu Leu Leu Glu Ser Leu Cys Ile Ser
    930                 935                 940

Asn Ile Ser Glu Val Met Ser Arg Pro Thr Gly Glu Leu Phe Arg Lys
945                 950                 955                 960

Gly Leu Ser Lys Val Arg Asp Leu Lys Ile Asn Gly Cys Glu Lys Leu
                965                 970                 975

Thr Ser Ser Leu Lys Asn Glu Ala Arg Leu Leu Gln Arg Leu Thr Ser
            980                 985                 990

Leu Gly Arg Leu Glu Ile Lys Asp Asn Ser Arg Leu Val Glu Glu Leu
        995                 1000                1005

Gly Glu Glu Ala Glu Glu Leu Leu Gln Leu Gln Ile Leu Asp Cys
    1010                1015                1020

Lys Leu Glu Leu Leu Lys Leu Arg Lys Cys Glu Asn Leu Leu Lys
    1025                1030                1035
```

```
Leu Pro Lys Gly Leu Asn Gln Leu Ser Ser Leu Gln Lys Leu Arg
    1040                1045                1050

Ile Val Gly Cys Ser Ser Leu Val Ser Phe Pro Asp Val Gly Leu
    1055                1060                1065

Pro Pro Ser Leu Lys Asp Ile Trp Ile Ala Glu Cys Asn Ser Leu
    1070                1075                1080

Ile Tyr Phe Ala Lys Phe Gln Ile Pro Gln Asn Leu Arg Ile Ile
    1085                1090                1095

Gln Ile Arg Gly Cys Lys Ser Leu Lys Ser Leu Val Asp Glu Glu
    1100                1105                1110

Glu Cys Glu Arg Leu Gly Leu Ile Ala Pro Asn Gly Phe Phe Ser
    1115                1120                1125

Asp Asn Thr Asn His Cys Leu Glu Ser Ile Leu Ile Trp Lys Cys
    1130                1135                1140

Gln Asn Leu Lys Ser Leu Pro Asp Gly Leu Cys His Leu Ser Asn
    1145                1150                1155

Leu Gln Thr Leu Arg Ile Glu Tyr Cys Gly Ser Leu Val Ser Ile
    1160                1165                1170

Pro Arg Leu Ser Gly Gly Arg Arg Pro Ser Asn Leu Arg Glu Ile
    1175                1180                1185

Trp Ile Arg Asp Cys Glu Lys Leu Glu Ala Leu Pro Glu Asp Met
    1190                1195                1200

His Asn Leu Asn Ser Leu Glu Glu Leu Arg Ile Asp Tyr Arg Glu
    1205                1210                1215

Gly Leu Thr Phe Pro Pro Asn Leu Lys Ser Leu Gly Ile Arg Lys
    1220                1225                1230

Val Lys Ser Cys Lys Ser Leu Trp Glu Leu Glu Trp Gly Leu His
    1235                1240                1245

Arg Leu Thr Ser Leu Lys Ile Gly Gly Glu Asp Pro Asp Thr Val
    1250                1255                1260

Ser Phe Pro Pro Asp Met Val Arg Met Glu Thr Leu Phe Pro Lys
    1265                1270                1275

Ser Leu Thr Ser Leu Ser Ile Asp Gly Phe Pro Asn Leu Lys Lys
    1280                1285                1290

Leu Ser Ser Lys Gly Phe Gln Phe Leu Thr Ser Leu Gln Ser Leu
    1295                1300                1305

Thr Leu Leu Asp Cys Pro Lys Leu Ala Ser Ile Pro Glu Glu Gly
    1310                1315                1320

Leu Pro Pro Ser Leu Glu Glu Leu Ile Ile Asp Gly Cys Pro Val
    1325                1330                1335

Leu Lys Glu Arg Cys Gln Pro Gly Lys Gly Arg Tyr Trp His Lys
    1340                1345                1350

Ile Ser His Ile Pro Phe Ile Glu Ile Asp Trp His Ile Ile
    1355                1360                1365
```

<210> SEQ ID NO 2
<211> LENGTH: 8485
<212> TYPE: DNA
<213> ORGANISM: Malus zumi

<400> SEQUENCE: 2

```
ctagttctag gatgatgtta gagagactat atatatatat atatattttt ttttttttaag    60 aaatgatatt atctatacta aagaaaattg atgagttcag cgtcacaaag ttattaataa   120
tgttgttcaa atttatattt ggtaaaaaat caaacttaaa gagtctactt ttaaaaaggt   180
```

-continued

```
atgcttataa aatatatgaa ctgacagaaa gtttgtaaca tctcatatcg tctaggggag    240
tggatcatct atgtcttata tctatatttt catctctacc tagcacgaga cattttggga    300
gcttactggt ttcgggttcc atcgaaactc agcgagttcg ctcgagagca atctcatgat    360
acgtagcacg atattgccta aaacgaataa tgtcatgcta tgacgaaatc gagactatat    420
gtgatgggtc cgatccaaaa tgtgacaaaa ttcatgaaaa actcttttaa aagaatctta    480
ttagcatttt tctttttcta aacagcataa atatttgggg attgatattt acgagcgtgt    540
cggaagcagc cgaatcgaag tcacgagata cgaaagagt aggcgtgggc cggaatgaac     600
ggatattatg catttgctga gtcgattcca cgacatgcag agtcagatac acgtagaagc    660
cgtccgttgt ggtcccacat cttaattaat taatttccat ttgtagttgg gtaggtttaa    720
aggataaatt aggattatca cgctcacaaa ataacatgat cagcattgca agggaatgtt    780
gctcagttgt ttacgagtca cctttgcacc cgaagtttca tgtttggttc gccatctcca    840
aaatcgatcg cataaaggaa aaagaaatt gtagcaagtc tctcaattaa aaattcatga     900
tcatttgtct cttaatttcc caaaacgtgc ggctatagtt attttgtca actttatcat      960 aacttttgtc aaaacaagtt aagttgaaaa aacattgct ataattgtat taaagttaag    1020
atatcattgt ttcaattaga ttaaaattga gaaactattt ttacaattt ctcatttagt    1080 tttccatatt cgcttcttga ttcggcctca tgtgcctagc acgtgactca ttttgacgaa    1140
aattttagcg gtgttgacga aatggacttt agctgcacat tttaatgagt taagagacca    1200
attatcatga attttttaatt aagagatcat tattctaatt tgattaaaat tgagagatca   1260
ttgacacaat ttctccaaat gaaaaaaaaa cagcaataac cgtgtagaac ataggagata    1320
agaaagcaat caaatgataa aacaatatga ccccacgaaa aataaaaaga gaggaaaaag    1380
aggagtctaa ctctcctttt gggcagaagg aagaagactt cgttatggtc tttcaacacc    1440
taattatctc agcaaattga agagctctaa agtagtctag atctgttgat cttaatgatc    1500
tatggaaaca agtcccttca tcttcatcat catctgaaaa ctccaacgca gtaagttcct    1560
cttgcaacta tacatgccaa atccattatt tatttatttc attttttcttc aagtttgtat   1620 gcttaattaa ttattttatc aataaccatc tatataatct gtgcactttt caggcttagt    1680
tattccatcg ttcagtctgg atttgttgat cataagtgca aacaagtgcc ctcatgacct    1740
gattgactcc catgaaactg cttcttgcta cagatcatgt ccaatattcg tgcaagttcg    1800
agtcttgaaa cgtaggattg caaggtaatc ccaaagctgc ccatttgttt gttcaacatg    1860
ttaaaattta agaaaataa ccatttattt gtttaacatg ttaaaattta agaaaataat     1920
gtatactaat acatgatttt tgcaatcata tatgatatgt tttattatgc tttattattt    1980
aaagagtaat gctagaaaaa ctacatattt atactatatt agtgtatcat ctcatatggc    2040
aagtggtgga cacaatcaat atcctgtgag ataaattcat aaattgacgt tacgtgtata    2100
cctcacttgc cacattagat ggtacataaa tgtgacacaa aaatatgtga tcttcccaac    2160
attttcctat taagtaatat tatgtggtgt gttttattgt gctttataca tacaatatca    2220
agtttttttt atttttttatt gaaacatata atatcaagtt attagattat ttggtagtac    2280
tatattaggg attgtatacc tggcgatacg gttatgatgt tggcaacctt gatctgaatg    2340
cgtcctgttg cctgccatct ctagtcccaa attgtcacct ctagaaatgt ttactaggag    2400
tccattaatt gattatttca cttttactat aaatttgtat atgattgcgc atgcatcaat    2460
aattagttct catcatttta attggtgcag ttgtgactat ttctgagtct cgacagatca    2520
```

```
agcttccaaa tttccaagga actagtattt gactgttgat cttcccttcg ttgagtctgt    2580
atttgttgat cacaagcaga gttagatttg aacttccatg taagttctta ttatttgttt    2640
gaataataca ttggttgttt tgcattttat ttgaaccact ttttattcat ttgtttcttc    2700
acttaatttg tacagttctg cacctcaata ttgctcaaga gcgattcggt ctttctttga    2760
ctgcttggag taatcctcgc tcttaatatg gcactgggag aggttttct tgcggcgttt     2820 ctacagttgc tgctcgacag gttgacccct cgcgagattc ttgagtactt gggaaatttc    2880
cggggcgtcg gacagaagct ggagaagtgg aggaccacgt tgtctacaat cggagcggtg    2940
ctgagcgacg ctgaggaaag gcaactgact gaaggtggtg tgaaactgtg gctggatgat    3000
ctcagagacc tggcctatga tatcgaagac atgttggaca aatttgccgt taaaatgttg    3060
aagcgcatga tagagggatg tgatcaagcc agcacaagca ggaaggtacg gagatcattt    3120
tataaagtta aattgagttt tgatatgaac tccgaaatga gaagattac gaagcggttg     3180 caagacatat ctgaacggaa agataagttt ggcttgaaag atattgggac gtctgctaag    3240
gaatcgcgaa gtctaccaag ttcagacgtg ttagatgaaa agcttgttgt tggaagagat    3300
ggtgacaaat gggagattat tgaattgttg tcaaaaaaat acgagcatac agatgccgtc    3360
aattttggtg tagttgctat agttggcatg cccggagtcg ggaagacaac acttgctcaa    3420
cttgtattca accgcaaaga tgatgccatg aaggagtttg agctaaaggt gtgggtatgt    3480
gtgtctgatg acttcgatgt tgaacgagtg acgaaggcaa ttcttgaatc aatcacatcc    3540
cgacccgttc aagtgcagga gtttagtcaa attcagcatg atttgagtga gcaattaaga    3600
ggaaaaaagt tttaatcgt tttagatgat atctggaaca aagatgactc tgatctatac     3660
gatctctgga caagacttca atcccctttt ggcatcggag caggaggaag taagattatt    3720
gtgacaaccc gtgatgtgaa tgttgcaaag attatgggag ccactggagt tcataatttg    3780
gagtgtatgg cagatgatga ttgtttggaa atatttgagc gacatgcgtt caggggaatt    3840
aatactggaa agccggtaaa ttatgattta attaagacaa gaattgttga aaaatgtcgt    3900
ggcttaccat tagctgcaag gactctcggt ggtcttttac gttgcaaaga aaaagatgag    3960 tgggagaaa tattgaacaa caagttatgg aatctagcag acaagagtgg cattctcccc    4020
gtactaaagt tgagctatca ctatcttcca tcaaatttga agaggtgttt tgcatattgc    4080
tcaatacttc caaatgacta tgaatttggg gagaagcagc tcattctttt gtggatggca    4140
gagggtttga ttcaacaaaa tcctgacgac aataaacaaa tagaggattt gggccgcgac    4200
tactttcgag agctattagc aaggtcgctg tttcaagaat caagcaaaaa caattcacga    4260
tatgtaatgc atgacctcgt taatgattta gcacaatggg cagcaggtga aatatgtttt    4320
agattggaag ataagcaagg taataacttg caaagcaatt gctttcgaag gctcgccat    4380 tcgtctttca ttgctggtcg atttgatgga gttatgagat ttgaggactt tccaaaagtt    4440
gaacgtttgc gaacattcct gccactttca cttcagatt ccaggggatg gccaaatat    4500 ttgtctcgta aggttacttt tgagctatta ccacagttgc aatacttacg agtgctctct    4560
ttcaatgact acacaataac tgagctgcca gactcaatcg tgatttgag gttgttacag    4620 tatcttgacc tttcctatac acatatagcc agtttgccta atcaacaag cactctttac    4680 cacttgcaaa cattgatatt ggaaggttgt tctcaattga agtcattgcc cgcgaacatg    4740
agtaatctaa ttaatttgcg ccatctcaac aactcagatg catcttcgtt gaaaggaatg    4800
ccttcgcaac taggtcgatt gacaaatcta caatcactgc ctctttttgt ggtgagcgaa    4860
ggaagtgatc attcagggat aagagagata gggcccctat tgcatctccg agggacattg    4920
```

```
tgcctcttag gattggagaa tgtgactgat gtcgaggatg ccaggagggc caacttgaaa    4980
tgcaaggaga ggcttgattc actggtccta aatggtatc attcaagcga cacgagagaa     5040
acagaatccg ctgtgcttga catgttacag cctcatacaa agctcaagga gctcaccatc    5100
aagggttatg ccagagagga attttcatca tgggttggag gtcccttgtt ctctaatatg    5160
gtgcttgtgc gcttagagga atgtaacaat tgtttatcgt tgccacctct cggacaattg    5220
cctcgtctca aagagcttta tattggagga atgaatgcag tcgaaagtgt tggtgctgag    5280
ttttatggtg agtgtgtcat gccttttccg ctgttagaga ttctcgagtt tgtggatatg    5340
cggcattgga aggtgtggct tccttttcca ctggatcacg aagtggtgt tttccctttc     5400 ctaaaaaggc tttcaatcca ggaatgttct aagttggaag gtaaactgcc agagaagctt    5460
gatttgttag ccgaacttga aattgttaaa tgtgaggaat tgacggtttc gattgccaac    5520
tacaaacagc ttcgtcagct aaacattgac ggttgtaaag tgttggaaca tacagctgct    5580
aaggttgagt tgagttatt agagtccttg tgcatttcaa acatttcaga ggtgatgtct     5640
cggccaacag gggaattgtt caggaaggga ctaagcaagg ttagagattt gaagatcaat    5700
ggatgtgaga agctgacgtc ttcactgaag aatgaggcta gattattgca gcggttgact    5760
tctcttggcc gtttggaaat taaagacaac tctcgtctag ttgaagaatt gggagaagaa    5820
gcagaggagt tgctgcaatt gcaaatattg gattgcaagc ttgaacttct aaagttaaga    5880
aagtgcgaaa atcttttgaa gctaccaaaa gggttaaatc agctgtcgtc tcttcaaaag    5940
cttcgcatag taggatgttc aagtctagtt tcttttccag atgttggtct gccaccttct    6000
cttaaagaca tctggattgc agagtgcaat tcgttgatat attttgcaaa attccagatt    6060
ccccaaaatc tcagaataat acagataaga gggtgcaaaa gtttgaaatc actagtagat    6120
gaggaggaat gtgaacgact gggtttaata gcaccgaacg ggttcttcag cgacaacacc    6180
aatcactgcc ttgaatctat tttgatctgg aagtgccaaa atctgaaatc cttaccggat    6240
ggcttatgcc acctcagcaa tcttcaaact ctaagaatcg aatactgtgg aagtcttgtt    6300
tccatcccga gactgagtgg ggggagaaga ccctccaacc tgagagagat ctggatccga    6360
gattgcgaga aattggaggc gttgcccgaa gacatgcaca atctcaactc tcttgaggaa    6420
ttgaggatcg actaccggga aggtttgact tttcctccca acctaaaatc acttggaatt    6480
aggaaggtca agagctgtaa gtcattgtgg gagttggagt gggggttgca cagactcacc    6540
tctcttaaaa tcggtggtga agacccggat acggtgtcgt ttccacccga catggtacgg    6600
atggagacgc tcttccccaa atctctcact agcctctcaa tagatggctt cccgaatttg    6660
aagaaactga gcagcaaggg ctttcaattc ctcacctccc ttcaatctct tacactcttg    6720
gattgtccaa agctagcatc cattccagag gagggtctgc ctccttcact agaggaatta    6780
atcatcgatg ggtgtccagt gctaaaagag agatgccaac caggaaaagg acgctactgg    6840
cacaaaatat cccacatccc tttcatagag atagattggc acataaattg atgcagatgg    6900
tccaggtatc atctgtcgag gaatgtttta atattaatat tattattatt attatcttta    6960 ttctttttt tttgggtaat taatcatgtt tattcttgta aagtaaagta atccacatat     7020
tttggtttgg gtcaaggttt tggggggttga ggagtggctg ctttgggagg tcttcaattg   7080
gcgacaacct ggatatttct cggccaacgt ttcttctccc ggattcctat attttctttt    7140
tttatttttt tggtaaacga ttgctatgtt tgcttggccc cttttcactg atttgtatta    7200
taactttgta aatcaggcca ctttcaccta atgttttatt ttatttagc aaattttgac     7260
```

-continued

```
ttatgagcta gttatcttaa tgcatcgaga ataagcaatc aacaaagaaa tggaaatgca      7320
aatgatgacc actaaatgac ttcctttacc ataacttgtc ttcctgaaag tagataatat      7380
gtgccaacaa attttggtca atcaaatcct tataccaagc cttcgtcact tattcaaaaa      7440
gtgcattatt catctaatta atatgtaata aattggtgac gattatacat tttaactgag      7500
ttctaaggaa aattgagggt agtaatacat cagtactaaa acgtgaattt gtgaaaaact      7560
ggtttgattt tattcgtgga ttttatgtgg gatagtgatt gtgcaatttt ccattttta      7620 tttgacccte aattttatte caaacgcaca aaccacttca gggctgacgc cgacttaacg      7680
gcgatccgaa tcatctttcc gttccgtcat tttaaaatta tttagtaatc ctaaatttct      7740
tcatctaaac atagtgtaac tcgttaagaa gactctcgaa gtcgagagaa aaagatgagc      7800
gacgcgtgga aaatagggac acaaacggaa agaaaacaga gaagcgaggg cagttccgtc      7860
cggacactgg tgatcaacag taccgggga aactcacgtt tagtatatat gatttacaag      7920
ctttatttgg gactgcccga atttgattct taagcaatgt ttattaaagt gaggtgatct      7980
gataatgacc tgattcatta acaagttatg ttgttttatg ttgggttaat gggtcctgca      8040
agacattgct taatgtctaa atttggcaaa caatattttg tcgagttctt gattcaacaa      8100
tgactcaact tgttaaaggg ttcttaatga gtcctaataa cgactcgact tgttaacagg      8160
ttgactaaaa acctattact ttcatgtcgt tttgtatcaa atgaacgagt cgtgcaataa      8220
attgtcagac ctaatgggac cgtgccaaac aattgatcgt agcacgatat tatctgcttt      8280
aggtcctgac cacaccctca cggttttgtt tctgataact cacacgaaaa cttcccagtg      8340
ggtcatccat catgggattg ctctcgcgca atctcgctta acttcgaagt tcctatgaaa      8400
tctgaagcca gtgagttcca aaaagacctt gtgctaattg gaggtaggaa tgtacatata      8460
aggcatagag gatccactcc cctag                                           8485
```

<210> SEQ ID NO 3
<211> LENGTH: 4101
<212> TYPE: DNA
<213> ORGANISM: Malus zumi

<400> SEQUENCE: 3

```
atggcactgg gagaggtttt tcttgcggcg tttctacagt tgctgctcga caggttgacc        60
cctcgcgaga ttcttgagta cttgggaaat ttccggggcg tcggacagaa gctggagaag       120
tggaggacca cgttgtctac aatcggagcg gtgctgagcg acgctgagga aaggcaactg       180
actgaaggtg gtgtgaaact gtggctggat gatctcagag acctggccta tgatatcgaa       240
gacatgttgg acaaatttgc cgttaaaatg ttgaagcgca tgatagaggg atgtgatcaa       300
gccagcacaa gcaggaaggt acggagatca tttttataaag ttaaattgag ttttgatatg       360
aactccgaaa tgaagaagat tacgaagcgg ttgcaagaca tatctgaacg gaaagataag       420
tttggcttga agatattgg gacgtctgct aaggaatcgc gaagtctacc aagttcagac       480
gtgttagatg aaaagcttgt tgttggaaga gatggtgaca aatgggagat tattgaattg       540
ttgtcaaaaa aatacgagca tacagatgcc gtcaattttg gtgtagttgc tatagttggc       600
atgcccggag tcgggaagac aacacttgct caacttgtat tcaaccgcaa agatgatgcc       660
atgaaggagt ttgagctaaa ggtgtgggta tgtgtgtctg atgacttcga tgttgaacga       720
gtgacgaagg caattcttga atcaatcaca tcccgacccg ttcaagtgca ggagtttagt       780
caaattcagc atgatttgag tgagcaatta agaggaaaaa agttttaat cgttttagat       840 gatatctgga acaaagatga ctctgatcta tacgatctct ggacaagact tcaatcccct       900
```

```
tttggcatcg gagcaggagg aagtaagatt attgtgacaa cccgtgatgt gaatgttgca    960
aagattatgg gagccactgg agttcataat ttggagtgta tggcagatga tgattgtttg   1020
gaaatatttg agcgacatgc gttcagggga attaatactg gaaagccggt aaattatgat   1080
ttaattaaga caagaattgt tgaaaaatgt cgtggcttac cattagctgc aaggactctc   1140
ggtggtcttt tacgttgcaa agaaaaagat gagtggggag aaatattgaa caacaagtta   1200
tggaatctag cagacaagag tggcattctc cccgtactaa agttgagcta tcactatctt   1260
ccatcaaatt tgaagaggtg ttttgcatat tgctcaatac ttccaaatga ctatgaattt   1320
ggggagaagc agctcattct tttgtggatg cagagggtt tgattcaaca aaatcctgac    1380
gacaataaac aaatagagga tttgggccgc gactactttc gagagctatt agcaaggtcg   1440
ctgtttcaag aatcaagcaa aaacaattca cgatatgtaa tgcatgacct cgttaatgat   1500
ttagcacaat gggcagcagg tgaaatatgt tttagattgg aagataagca aggtaataac   1560
ttgcaaagca attgctttcg aagggctcgc cattcgtctt tcattgctgg tcgatttgat   1620
ggagttatga gatttgagga cttt ccaaaa gttgaacgtt gcgaacatt cctgccactt    1680
tcactttcag attccagggg atgggccaaa tatttgtctc gtaaggttac ttttgagcta   1740
ttaccacagt tgcaatactt acgagtgctc tctttcaatg actacacaat aactgagctg   1800
ccagactcaa tcggtgattt gaggttgtta cagtatcttg accttcccta tacacatata   1860
gccagtttgc ctaaatcaac aagcactctt taccacttgc aaacattgat attggaaggt   1920
tgttctcaat tgaagtcatt gcccgcgaac atgagtaatc taattaattt gcgccatctc   1980
aacaactcag atgcatcttc gttgaaagga atgccttcgc aactaggtcg attgacaaat   2040
ctacaatcac tgcctctttt tgtggtgagc gaaggaagtg atcattcagg ataagagag    2100
atagggcccc tattgcatct ccgagggaca ttgtgcctct taggattgga gaatgtgact   2160
gatgtcgagg atgccaggag ggccaacttg aaatgcaagg agaggcttga ttcactggtc   2220
ctaaaatggt atcattcaag cgacacgaga gaaacagaat ccgctgtgct tgacatgtta   2280
cagcctcata caaagctcaa ggagctcacc atcaagggtt atgccagaga ggaattttca   2340
tcatgggttg gaggtcccct gttctctaat atggtgcttg tgcgcttaga ggaatgtaac   2400
aattgtttat cgttgccacc tctcggacaa ttgcctcgtc tcaaagagct ttatattgga   2460
ggaatgaatg cagtcgaaag tgttggtgct gagttttatg gtgagtgtgt catgcctttt   2520
ccgctgttag agattctcga gtttgtggat atgcggcatt ggaaggtgtg gcttccttttc   2580
caactggatc acgaagtgg tgttttccct ttcctaaaaa ggctttcaat ccaggaatgt    2640
tctaagttgg aaggtaaact gccagagaag cttgatttgt tagccgaact tgaaattgtt   2700
aaatgtgagg aattgacggt ttcgattgcc aactacaaac agcttcgtca gctaaacatt   2760
gacggttgta aagtgttgga acatacagct gctaaggttg agtttgagtt attagagtcc   2820
ttgtgcattt caaacatttc agaggtgatg tctcggccaa caggggaatt gttcaggaag   2880
ggactaagca aggttagaga tttgaagatc aatggatgtg agaagctgac gtcttcactg   2940
aagaatgagg ctagattatt gcagcggttg acttctcttg gccgtttgga aattaaagac   3000
aactctcgtc tagttgaaga attgggagaa gaagcagagg agttgctgca attgcaaata   3060
ttggattgca agcttgaact tctaaagtta agaaagtgcg aaaatctttt gaagctacca   3120
aaagggttaa atcagctgtc gtctcttcaa aagcttcgca tagtaggatg ttcaagtcta   3180
gtttcttttc cagatgttgg tctgccacct tctcttaaag acatctggat tgcagagtgc   3240
```

```
aattcgttga tatattttgc aaaattccag attccccaaa atctcagaat aatacagata    3300
agagggtgca aaagtttgaa atcactagta gatgaggagg aatgtgaacg actgggttta    3360
atagcaccga acgggttctt cagcgacaac accaatcact gccttgaatc tattttgatc    3420
tggaagtgcc aaaatctgaa atccttaccg gatggcttat gccacctcag caatcttcaa    3480
actctaagaa tcgaatactg tggaagtctt gtttccatcc cgagactgag tgggggaga    3540 agaccctcca acctgagaga gatctggatc cgagattgcg agaaattgga ggcgttgccc    3600
gaagacatgc acaatctcaa ctctcttgag gaattgagga tcgactaccg ggaaggtttg    3660
acttttcctc ccaacctaaa atcacttgga attaggaagg tcaagagctg taagtcattg    3720
tgggagttgg agtgggggtt gcacagactc acctctctta aaatcggtgg tgaagacccg    3780
gatacggtgt cgtttccacc cgacatggta cggatggaga cgctcttccc caaatctctc    3840
actagcctct caatagatgg cttcccgaat ttgaagaaac tgagcagcaa gggctttcaa    3900
ttcctcacct cccttcaatc tcttacactc ttggattgtc caaagctagc atccattcca    3960
gaggagggtc tgcctccttc actagaggaa ttaatcatcg atgggtgtcc agtgctaaaa    4020
gagagatgcc aaccaggaaa aggacgctac tggcacaaaa tatcccacat ccctttcata    4080
gagatagatt ggcacataat t                                              4101

<210> SEQ ID NO 4
<211> LENGTH: 7126
<212> TYPE: DNA
<213> ORGANISM: Malus zumi

<400> SEQUENCE: 4
ctagttctag gatgatgtta gagagactat atatatatat atatattttt ttttttaag      60 aaatgatatt atctatacta aagaaaattg atgagttcag cgtcacaaag ttattaataa    120
tgttgttcaa atttatattt ggtaaaaaat caaacttaaa gagtctactt ttaaaaaggt    180
atgcttataa aatatatgaa ctgacagaaa gtttgtaaca tctcatatcg tctaggggag    240
gggatcatct atgtcttata tctatatttt catctctacc tagcacgaga cattttggga    300
gcttactggt ttcgggttcc atcgaaactc agcgagttcg ctcgagcaa atctcatgat     360 acgtagcacg atattgccta aaacgaataa tgtcatgcta tgacgaaatc gagactatat    420
gtgatgggtc cgatccaaaa tgtgacaaaa ttcatgaaaa actcttttaa aagaatctta    480
ttagcatttt tcttttttcta aacagcataa atatttgggg attgatattt acgagcgtgt   540
cggaagcagc cgaatcgaag tcacgagata cgaaaagagt aggcgtgggc cggaatgaac    600
ggatattatg catttgctga gtcgattcca cgacatgcag agtcagatac acgtagaagc    660
cgtccgtcgt ggtcccacat cttaattaat taatttccat ttgtagttgg gtaggtttaa    720 aggataaaatt aggattatca cgctcacaaa ataacatgat cagcattgca agggaatgtt    780
gctcagttgt ttacgagtca cctttgcacc cgaagtttca tgtttggttc gccatctcca    840
aaatcgatcg cataaaggaa aaagaaaatt gtagcaagtc tctcaattaa aaattcatga    900
tcatttgtct cttaatttcc caaaacgtgc ggctatagtt attttgtca actttatcat     960 aactttgtc aaaacaagtt aagttgaaaa aacattgct ataattgtat taagttaag     1020 atatcattgt ttcaattaga ttaaaattga gaactatttt tacaattttt ctcatttagt   1080
tttccatatt cgcttcttga ttcggcctca tgtgcctagc acgtgactca ttttgacgaa   1140
aattttagcg gtgttgacga aatggacttt agctgcacat tttaatgagt taagagacca   1200
attatcatga attttttaatt aagagatcat tattctaatt tgattaaat tgagagatca   1260
```

```
ttgacacaat tttctccaaa tgaaaaaaaa acagcaataa ccgtgtagaa cataggagat    1320
aagaaagcaa tcaaatgata aaacaatatg accccacgaa aaataaaaag agaggaaaaa    1380
gaggagtcta actctccttt tgggcagaag gaagaagact tcgttatggt ctttcaacac    1440
ctaattatct cagcaaattg aagagctcta aagtagtcta gatctgttga tcttaatgat    1500
ctatggaaac aagtcccttc atcttcatca tcatctgaaa actccaacgc agtaagttcc    1560
tcttgcaact atacatgcca aatccattat ttatttattt cattttctt caagtttgta    1620 tgcttaatta attattttat caataaccat ctatataatc tgtgcacttt tcaggcttag    1680
ttattccatc gttcagtctg gatttgttga tcataagtgc aaacaagtgc cctcatgacc    1740
tgattgactc ccatgaaact gcttcttgct acagatcatg tccaatattc gtgcaagttc    1800
gagtcttgaa acgtaggatt gcaaggtaat cccaaagctg cccatttgtt tgttcaacat    1860
gttaaaattt aagaaaaata accatttatt tgtttaacat gttaaaattt aagaaaataa    1920
tgtatactaa tacatgattt ttgcaatcat atatgatatg ttttattatg ctttattatt    1980
taaagagtaa tgctagaaaa actacatatt tatactatat tagtgtatca tctcatatgg    2040
caagtggtgg acacaatcaa tatcctgtga gataaattca taaattgacg ttacgtgtat    2100
acctcacttg ccacattaga tggtacataa atgtgacaca aaaatatgtg atcttcccaa    2160
cattttccta ttaagtaata ttatgtggtg tgttttattg tgcttatac atacaatatc    2220 aagttttttt tatttttat tgaaacatat aatatcaagt tattagatta tttggtagta    2280
ctatattagg gattgtatac ctggcgatac ggttatgatg ttggcaacct tgatctgaat    2340
gcgtcctgtt gcctgccatc tctagtccca aattgtcacc tctagaaatg tttactagga    2400
gtccattaat tgattattc acttttacta taaatttgta tatgattgcg catgcatcaa    2460
taattagttc tcatcatttt aattggtgca gttgtgacta tttctgagtc tcgacagatc    2520
aagcttccaa atttccaagg aactagtatt tgactgttga tcttcccttc gttgagtctg    2580
tatttgttga tcacaagcag agttagattt gaacttccat gtaagttctt attatttgtt    2640
tgaataatac attggttgtt ttgcatttta tttgaaccac ttttattca tttgtttctt    2700 cacttaattt gtacagttct gcacctcaat attgctcaag agcgattcgg tctttctttg    2760
actgcttgga gtaatcctcg ctcttaatat ggcactggga gaggttttc ttgcggcgtt    2820 tctacagttg ctgctcgaca ggttgacccc tcgcgagatt cttgagtact tgggaaattt    2880
ccggggcgtc ggacagaagc tggagaagtg gaggaccacg ttgtctacaa tcggagcggt    2940
gctgagcgac gctgaggaaa ggcaactgac tgaaggtggt gtgaaactgt ggctggatga    3000
tctcagagac ctggcctatg atatcgaaga catgttggac aaatttgccg ttaaaatgtt    3060
gaagcgcatg atagagggat gtgatcaagc cagcacaagc aggaaggtac ggagatcatt    3120
ttataaagtt aaattgagtt ttgatatgaa ctccgaaatg aagaagatta cgaagcggtt    3180
gcaagacata tctgaacgga aagataagtt tggcttgaaa gatattggga cgtctgctaa    3240
ggaatcgcga agtctaccaa gttcagacgt gttagatgaa aagcttgttg ttggaagaga    3300
tggtgacaaa tggagagatta ttgaattgtt gtcaaaaaaa tacgagcata cagatgccgt    3360
caattttggt gtagttgcta tagttggcat gcccggagtc gggaagacaa cacttgctca    3420
acttgtattc aaccgcaaag atgatgccat gaaggagttt gagctaaagg tgtgggtatg    3480
tgtgtctgat gacttcgatg ttgaacgagt gacgaaggca attcttgaat caatcacatc    3540
ccgacccgtt caagtgcagg agtttagtca aattcagcat gatttgagtg agcaattaag    3600
```

```
aggaaaaaag ttttaatcg ttttagatga tatctggaac aaagatgact ctgatctata    3660
cgatctctgg acaagacttc aatccccttt tggcatcgga gcaggaggaa gtaagattat    3720
tgtgacaacc cgtgatgtga atgttgcaaa gattatggga gccactggag ttcataattt    3780
ggagtgtatg gcagatgatg attgtttgga aatatttgag cgacatgcgt tcagggaat    3840 taatactgga aagccggtaa attatgattt aattaagaca agaattgttg aaaaatgtcg    3900
tggcttacca ttagctgcaa ggactctcgg tggtctttta cgttgcaaag aaaaagatga    3960
gtggggagaa atattgaaca acaagttatg gaatctagca gacaagagtg gcattctccc    4020
cgtactaaag ttgagctatc actatcttcc atcaaatttg aagaggtgtt ttgcatattg    4080
ctcaatactt ccaaatgact atgaatttgg ggagaagcag ctcattcttt tgtggatggc    4140
agagggtttg attcaacaaa atcctgacga caataaacaa atagaggatt tgggccgcga    4200
ctactttcga gagctattag caaggtcgct gtttcaagaa tcaagcaaaa acaattcacg    4260
atatgtaatg catgacctcg ttaatgattt agcacaatgg gcagcaggtg aaatatgttt    4320
tagattggaa gataagcaag gtaataactt gcaaagcaat tgctttcgaa gggctcgcca    4380
ttcgtctttc attgctggtc gatttgatgg agttatgaga tttgaggact ttccaaaagt    4440
tgaacgtttg cgaacattcc tgccactttc actttcagat tccaggggat gggccaaata    4500
tttgtctcgt aaggttactt ttgagctatt accacagttg caatacttac gagtgctctc    4560
tttcaatgac tacacaataa ctgagctgcc agactcaatc ggtgatttga ggttgttaca    4620
gtatcttgac ctttcctata cacatatagc cagtttgcct aaatcaacaa gcactcttta    4680
ccacttgcaa acattgatat tggaaggttg ttctcaattg aagtcattgc ccgcgaacat    4740
gagtaatcta attaatttgc gccatctcaa caactcagat gcatcttcgt tgaaaggaat    4800
gggttcttca gcgacaacac caatcactgc cttgaatcta ttttgatctg gaagtgccaa    4860
aatctgaaat ccttaccgga tggcttatgc caccctcagca atcttcaaac tctaagaatc    4920
gaatactgtg gaagtcttgt ttccatcccg agactgagtg gggggagaag accctccaac    4980
ctgagagaga tctggatccg agattgcgag aaattggagg cgttgcccga agacatgcac    5040
aatctcaact ctcttgagga attgaggatc gactaccggg aaggtttgac ttttcctccc    5100
aacctaaaat cacttggaat taggaaggtc aagagctgta agtcattgtg ggagttggag    5160
tgggggttgc acagactcac ctctcttaaa atcggtggtg aagacccgga tacggtgtcg    5220
tttccacccg acatggtacg gatggagacg ctcttcccca aatctctcac tagcctctca    5280
atagatggct tcccgaattt gaagaaactg agcagcaagg gctttcaatt cctcacctcc    5340
cttcaatctc ttacactctt ggattgtcca aagctagcat ccattccaga ggagggtctg    5400
cctccttcac tagaggaatt aatcatcgat gggtgtccag tgctaaaaga gagatgccaa    5460
ccaggaaaag gacgctactg gcacaaaata tcccacatcc ctttcataga gatagattgg    5520
cacataattt gatgcagatg gtccaggtat catctgtcga ggaatgtttt aatattaata    5580
ttattattat tattatcttt attcttttt ttttgggtaa ttaatcatgt ttattcttgt    5640
aaagtaaagt aatccacata ttttggtttg ggtcaaggtt ttgggggttg aggagtggct    5700
gctttgggag gtcttcaatt ggcgacaacc tggatatttc tcggccaacg tttcttctcc    5760
cggattccta tattttcttt tttattttt ttggtaaacg attgctatgt ttgcttggcc    5820
ccttttcact gatttgtatt ataactttgt aaatcaggcc actttcacct aatgtttat    5880 tttatttag caaatttga cttatgagct agttatctta atgcatcgag aataagcaat    5940
caacaaagaa atggaaatgc aaatgatgac cactaaatga cttcctttac cataacttgt    6000
```

```
cttcctgaaa gtagataata tgtgccaaca aatttggtc  aatcaaatcc ttataccaag    6060
ccttcgtcac ttattcaaaa agtgcattat tcatctaatt aatatgtaat aaattggtga    6120
cgattataca ttttaactga gttctaagga aaattgaggg tagtaataca tcagtactaa    6180
aacgtgaatt tgtgaaaaac tggtttgatt ttattcgtgg attttatgtg ggatagtgat    6240
tgtgcaattt tccatttttt atttgaccct caatttttatt ccaaacgcac aaaccacttc    6300
agggctgacg ccgacttaac ggcgatccga atcatctttc cgttccgtca ttttaaaatt    6360
atttagtaat cctaaatttc ttcatctaaa catagtgtaa ctcgttaaga agactctcga    6420
agtcgagaga aaaagatgag cgacgcgtgg aaaatagga  cacaaacgga agaaaacag    6480 agaagcgagg gcagttccgt ccggacactg gtgatcaaca gtaccggggg aaactcacgt    6540
ttagtatata tgatttacaa gctttatttg ggactgcccg aatttgattc ttaagcaatg    6600
tttattaaag tgaggtgatc tgataatgac ctgattcatt aacaagttat gttgttttat    6660
gttgggttaa tgggtcctgc aagacattgc ttaatgtcta aatttggcaa acaatatttt    6720
gtcgagttct tgattcaaca atgactcaac ttgttaaagg gttcttaatg agtcctaata    6780
acgactcgac ttgttaacag gttgactaaa aacctattac tttcatgtcg ttttgtatca    6840
aatgaacgag tcgtgcaata aattgtcaga cctaatggga ccgtgccaaa caattgatcg    6900
tagcacgata ttatctgctt taggtcctga ccacaccctc acggttttgt ttctgataac    6960
tcacacgaaa acttcccagt gggtcatcca tcatgggatt gctctcgcgc aatctcgctt    7020
aacttcgaag ttcctatgaa atctgaagcc agtgagttcc aaaaagacct tgtgctaatt    7080
ggaggtagga atgtacatat aaggcataga ggatccactc ccctag                  7126
```

<210> SEQ ID NO 5
<211> LENGTH: 685
<212> TYPE: PRT
<213> ORGANISM: Malus zumi

<400> SEQUENCE: 5

Met Ala Leu Gly Glu Val Phe Leu Ala Ala Phe Leu Gln Leu Leu Leu
1               5                   10                  15

Asp Arg Leu Thr Pro Arg Glu Ile Leu Glu Tyr Leu Gly Asn Phe Arg
                20                  25                  30

Gly Val Gly Gln Lys Leu Glu Lys Trp Arg Thr Thr Leu Ser Thr Ile
            35                  40                  45

Gly Ala Val Leu Ser Asp Ala Glu Glu Arg Gln Leu Thr Glu Gly Gly
        50                  55                  60

Val Lys Leu Trp Leu Asp Asp Leu Arg Asp Leu Ala Tyr Asp Ile Glu
65                  70                  75                  80

Asp Met Leu Asp Lys Phe Ala Val Lys Met Leu Lys Arg Met Ile Glu
                85                  90                  95

Gly Cys Asp Gln Ala Ser Thr Ser Arg Lys Val Arg Arg Ser Phe Tyr
            100                 105                 110

Lys Val Lys Leu Ser Phe Asp Met Asn Ser Glu Met Lys Lys Ile Thr
        115                 120                 125

Lys Arg Leu Gln Asp Ile Ser Glu Arg Lys Asp Lys Phe Gly Leu Lys
    130                 135                 140

Asp Ile Gly Thr Ser Ala Lys Glu Ser Arg Ser Leu Pro Ser Ser Asp
145                 150                 155                 160

Val Leu Asp Glu Lys Leu Val Val Gly Arg Asp Gly Asp Lys Trp Glu
                165                 170                 175

-continued

```
Ile Ile Glu Leu Leu Ser Lys Lys Tyr Glu His Thr Asp Ala Val Asn
            180                 185                 190

Phe Gly Val Val Ala Ile Val Gly Met Pro Gly Val Gly Lys Thr Thr
        195                 200                 205

Leu Ala Gln Leu Val Phe Asn Arg Lys Asp Asp Ala Met Lys Glu Phe
    210                 215                 220

Glu Leu Lys Val Trp Val Cys Val Ser Asp Asp Phe Asp Val Glu Arg
225                 230                 235                 240

Val Thr Lys Ala Ile Leu Glu Ser Ile Thr Ser Arg Pro Val Gln Val
                245                 250                 255

Gln Glu Phe Ser Gln Ile Gln His Asp Leu Ser Glu Gln Leu Arg Gly
            260                 265                 270

Lys Lys Phe Leu Ile Val Leu Asp Asp Ile Trp Asn Lys Asp Asp Ser
        275                 280                 285

Asp Leu Tyr Asp Leu Trp Thr Arg Leu Gln Ser Pro Phe Gly Ile Gly
    290                 295                 300

Ala Gly Gly Ser Lys Ile Ile Val Thr Thr Arg Asp Val Asn Val Ala
305                 310                 315                 320

Lys Ile Met Gly Ala Thr Gly Val His Asn Leu Glu Cys Met Ala Asp
                325                 330                 335

Asp Asp Cys Leu Glu Ile Phe Glu Arg His Ala Phe Arg Gly Ile Asn
            340                 345                 350

Thr Gly Lys Pro Val Asn Tyr Asp Leu Ile Lys Thr Arg Ile Val Glu
        355                 360                 365

Lys Cys Arg Gly Leu Pro Leu Ala Ala Arg Thr Leu Gly Gly Leu Leu
    370                 375                 380

Arg Cys Lys Glu Lys Asp Glu Trp Gly Glu Ile Leu Asn Asn Lys Leu
385                 390                 395                 400

Trp Asn Leu Ala Asp Lys Ser Gly Ile Leu Pro Val Leu Lys Leu Ser
                405                 410                 415

Tyr His Tyr Leu Pro Ser Asn Leu Lys Arg Cys Phe Ala Tyr Cys Ser
            420                 425                 430

Ile Leu Pro Asn Asp Tyr Glu Phe Gly Glu Lys Gln Leu Ile Leu Leu
        435                 440                 445

Trp Met Ala Glu Gly Leu Ile Gln Gln Asn Pro Asp Asp Asn Lys Gln
    450                 455                 460

Ile Glu Asp Leu Gly Arg Asp Tyr Phe Arg Glu Leu Leu Ala Arg Ser
465                 470                 475                 480

Leu Phe Gln Glu Ser Ser Lys Asn Asn Ser Arg Tyr Val Met His Asp
                485                 490                 495

Leu Val Asn Asp Leu Ala Gln Trp Ala Ala Gly Glu Ile Cys Phe Arg
            500                 505                 510

Leu Glu Asp Lys Gln Gly Asn Asn Leu Gln Ser Asn Cys Phe Arg Arg
        515                 520                 525

Ala Arg His Ser Ser Phe Ile Ala Gly Arg Phe Asp Gly Val Met Arg
    530                 535                 540

Phe Glu Asp Phe Pro Lys Val Glu Arg Leu Arg Thr Phe Leu Pro Leu
545                 550                 555                 560

Ser Leu Ser Asp Ser Arg Gly Trp Ala Lys Tyr Leu Ser Arg Lys Val
                565                 570                 575

Thr Phe Glu Leu Leu Pro Gln Leu Gln Tyr Leu Arg Val Leu Ser Phe
            580                 585                 590
```

-continued

```
Asn Asp Tyr Thr Ile Thr Glu Leu Pro Asp Ser Ile Gly Asp Leu Arg
            595                 600                 605

Leu Leu Gln Tyr Leu Asp Leu Ser Tyr Thr His Ile Ala Ser Leu Pro
610                 615                 620

Lys Ser Thr Ser Thr Leu Tyr His Leu Gln Thr Leu Ile Leu Glu Gly
625                 630                 635                 640

Cys Ser Gln Leu Lys Ser Leu Pro Ala Asn Met Ser Asn Leu Ile Asn
                645                 650                 655

Leu Arg His Leu Asn Asn Ser Asp Ala Ser Ser Leu Lys Gly Met Gly
                660                 665                 670

Ser Ser Ala Thr Thr Pro Ile Thr Ala Leu Asn Leu Phe
                675                 680                 685

<210> SEQ ID NO 6
    <211> LENGTH: 537
    <212> TYPE: PRT
    <213> ORGANISM: Malus zumi

<400> SEQUENCE: 6

Met Ala Leu Gly Glu Val Phe Leu Ala Ala Phe Leu Gln Leu Leu Leu
1               5                   10                  15

Asp Arg Leu Thr Pro Arg Glu Ile Leu Glu Tyr Leu Gly Asn Phe Arg
                20                  25                  30

Gly Val Gly Gln Lys Leu Glu Lys Trp Arg Thr Thr Leu Ser Thr Ile
            35                  40                  45

Gly Ala Val Leu Ser Asp Ala Glu Arg Gln Leu Thr Glu Gly Gly
        50                  55                  60

Val Lys Leu Trp Leu Asp Asp Leu Arg Asp Leu Ala Tyr Asp Ile Glu
65                  70                  75                  80

Asp Met Leu Asp Lys Phe Ala Val Lys Met Leu Lys Arg Met Ile Glu
                85                  90                  95

Gly Cys Asp Gln Ala Ser Thr Ser Arg Lys Val Arg Arg Ser Phe Tyr
            100                 105                 110

Lys Val Lys Leu Ser Phe Asp Met Asn Ser Glu Met Lys Lys Ile Thr
        115                 120                 125

Lys Arg Leu Gln Asp Ile Ser Glu Arg Lys Asp Lys Phe Gly Leu Lys
    130                 135                 140

Asp Ile Gly Thr Ser Ala Lys Glu Ser Arg Ser Leu Pro Ser Ser Asp
145                 150                 155                 160

Val Leu Asp Glu Lys Leu Val Val Gly Arg Asp Gly Asp Lys Trp Glu
                165                 170                 175

Ile Ile Glu Leu Leu Ser Lys Lys Tyr Glu His Thr Asp Ala Val Asn
            180                 185                 190

Phe Gly Val Val Ala Ile Val Gly Met Pro Gly Val Gly Lys Thr Thr
        195                 200                 205

Leu Ala Gln Leu Val Phe Asn Arg Lys Asp Ala Met Lys Glu Phe
    210                 215                 220

Glu Leu Lys Val Trp Val Cys Val Ser Asp Asp Phe Asp Val Glu Arg
225                 230                 235                 240

Val Thr Lys Ala Ile Leu Glu Ser Ile Thr Ser Arg Pro Val Gln Val
                245                 250                 255

Gln Glu Phe Ser Gln Ile Gln His Asp Leu Ser Glu Gln Leu Arg Gly
            260                 265                 270

Lys Lys Phe Leu Ile Val Leu Asp Asp Ile Trp Asn Lys Asp Asp Ser
        275                 280                 285
```

```
Asp Leu Tyr Asp Leu Trp Thr Arg Leu Gln Ser Pro Phe Gly Ile Gly
        290                 295                 300
Ala Gly Gly Ser Lys Ile Ile Val Thr Thr Arg Asp Val Asn Val Ala
305                 310                 315                 320
Lys Ile Met Gly Ala Thr Gly Val His Asn Leu Glu Cys Met Ala Asp
                325                 330                 335
Asp Asp Cys Leu Glu Ile Phe Glu Arg His Ala Phe Arg Gly Ile Asn
                340                 345                 350
Thr Gly Lys Pro Val Asn Tyr Asp Leu Ile Lys Thr Arg Ile Val Glu
        355                 360                 365
Lys Cys Arg Gly Leu Pro Leu Ala Ala Arg Thr Leu Gly Gly Leu Leu
370                 375                 380
Arg Cys Lys Glu Lys Asp Glu Trp Gly Glu Ile Leu Asn Asn Lys Leu
385                 390                 395                 400
Trp Asn Leu Ala Asp Lys Ser Gly Ile Leu Pro Val Leu Lys Leu Ser
                405                 410                 415
Tyr His Tyr Leu Pro Ser Asn Leu Lys Arg Cys Phe Ala Tyr Cys Ser
                420                 425                 430
Ile Leu Pro Asn Asp Tyr Glu Phe Gly Glu Lys Gln Leu Ile Leu Leu
        435                 440                 445
Trp Met Ala Glu Gly Leu Ile Gln Gln Asn Pro Asp Asp Asn Lys Gln
450                 455                 460
Ile Glu Asp Leu Gly Arg Asp Tyr Phe Arg Glu Leu Leu Ala Arg Ser
465                 470                 475                 480
Leu Phe Gln Glu Ser Ser Lys Asn Asn Ser Arg Tyr Val Met His Asp
                485                 490                 495
Leu Val Asn Asp Leu Ala Gln Trp Ala Ala Gly Glu Ile Cys Phe Arg
                500                 505                 510
Leu Glu Asp Lys Gln Gly Asn Asn Leu Gln Ser Asn Cys Phe Arg Arg
        515                 520                 525
Ala Arg His Ser Ser Phe Ile Ala Gly
        530                 535

<210> SEQ ID NO 7
<211> LENGTH: 2055
<212> TYPE: DNA
<213> ORGANISM: Artificial
<220> FEATURE:
<223> OTHER INFORMATION: Synthetic construct

<400> SEQUENCE: 7
atggcactgg gagaggtttt tcttgcggcg tttctacagt tgctgctcga caggttgacc      60
cctcgcgaga ttcttgagta cttgggaaat ttccggggcg tcggacagaa gctggagaag     120
tggaggacca cgttgtctac aatcggagcg gtgctgagcg acgctgagga aaggcaactg     180
actgaaggtg gtgtgaaact gtggctggat gatctcagag acctggccta tgatatcgaa     240
gacatgttgg acaaatttgc cgttaaaatg ttgaagcgca tgatagaggg atgtgatcaa     300
gccagcacaa gcaggaaggt acggagatca tttttataaag ttaaattgag ttttgatatg     360
aactccgaaa tgaagaagat tacgaagcgg ttgcaagaca tatctgaacg aaagataag     420 tttggcttga agatattgg gacgtctgct aaggaatcgc gaagtctacc aagttcagac     480
gtgttagatg aaaagcttgt tgttggaaga gatggtgaca atgggagat tattgaattg     540 ttgtcaaaaa aatacgagca tacagatgcc gtcaattttg gtgtagttgc tatagttggc     600
```

| | |
|---|---|
| atgcccggag tcgggaagac aacacttgct caacttgtat tcaaccgcaa agatgatgcc | 660 |
| atgaaggagt ttgagctaaa ggtgtgggta tgtgtgtctg atgacttcga tgttgaacga | 720 |
| gtgacgaagg caattcttga atcaatcaca tcccgacccg ttcaagtgca ggagtttagt | 780 |
| caaattcagc atgatttgag tgagcaatta agaggaaaaa agttttaat cgttttagat | 840 |
| gatatctgga acaaagatga ctctgatcta tacgatctct ggacaagact tcaatcccct | 900 |
| tttggcatcg gagcaggagg aagtaagatt attgtgacaa cccgtgatgt gaatgttgca | 960 |
| aagattatgg gagccactgg agttcataat ttggagtgta tggcagatga tgattgtttg | 1020 |
| gaaatatttg agcgacatgc gttcagggga attaatactg gaaagccggt aaattatgat | 1080 |
| ttaattaaga caagaattgt tgaaaaatgt cgtggcttac cattagctgc aaggactctc | 1140 |
| ggtggtcttt tacgttgcaa agaaaaagat gagtggggag aaatattgaa caacaagtta | 1200 |
| tggaatctag cagacaagag tggcattctc cccgtactaa agttgagcta tcactatctt | 1260 |
| ccatcaaatt tgaagaggtg ttttgcatat tgctcaatac ttccaaatga ctatgaattt | 1320 |
| ggggagaagc agctcattct tttgtggatg cagagggtt tgattcaaca aaatcctgac | 1380 |
| gacaataaac aaatagagga tttgggccgc gactactttc gagagctatt agcaaggtcg | 1440 |
| ctgtttcaag aatcaagcaa aaacaattca cgatatgtaa tgcatgacct cgttaatgat | 1500 |
| ttagcacaat gggcagcagg tgaaatatgt tttagattgg aagataagca aggtaataac | 1560 |
| ttgcaaagca attgctttcg aagggctcgc cattcgtctt tcattgctgg tcgatttgat | 1620 |
| ggagttatga gatttgagga ctttccaaaa gttgaacgtt tgcgaacatt cctgccactt | 1680 |
| tcactttcag attccagggg atgggccaaa tatttgtctc gtaaggttac ttttgagcta | 1740 |
| ttaccacagt tgcaatactt acgagtgctc tctttcaatg actacacaat aactgagctg | 1800 |
| ccagactcaa tcggtgattt gaggttgtta cagtatcttg acctttccta tacacatata | 1860 |
| gccagtttgc ctaaatcaac aagcactctt taccacttgc aaacattgat attggaaggt | 1920 |
| tgttctcaat tgaagtcatt gcccgcgaac atgagtaatc taattaattt gcgccatctc | 1980 |
| aacaactcag atgcatcttc gttgaaagga atgggttctt cagcgacaac accaatcact | 2040 |
| gccttgaatc tattt | 2055 |

```
<210> SEQ ID NO 8
<211> LENGTH: 1611
<212> TYPE: DNA
<213> ORGANISM: Artificial
<220> FEATURE:
<223> OTHER INFORMATION: Synthetic construct

<400> SEQUENCE: 8
```

| | |
|---|---|
| atggcactgg gagaggtttt tcttgcggcg tttctacagt tgctgctcga caggttgacc | 60 |
| cctcgcgaga ttcttgagta cttgggaaat ttccggggcg tcggacagaa gctggagaag | 120 |
| tggaggacca cgttgtctac aatcggagcg gtgctgagcg acgctgagga aaggcaactg | 180 |
| actgaaggtg gtgtgaaact gtggctggat gatctcagag acctggccta tgatatcgaa | 240 |
| gacatgttgg acaaatttgc cgttaaaatg ttgaagcgca tgatagaggg atgtgatcaa | 300 |
| gccagcacaa gcaggaaggt acggagatca tttttataaag ttaaattgag ttttgatatg | 360 |
| aactccgaaa tgaagaagat tacgaagcgg ttgcaagaca tatctgaacg gaaagataag | 420 |
| tttggcttga agatattgg gacgtctgct aaggaatcgc gaagtctacc aagttcagac | 480 |
| gtgttagatg aaaagcttgt tgttggaaga atggtgacaa atgggagat tattgaattg | 540 |
| ttgtcaaaaa aatacgagca tacagatgcc gtcaattttg gtgtagttgc tatagttggc | 600 |

```
atgcccggag tcgggaagac aacacttgct caacttgtat tcaaccgcaa agatgatgcc    660
atgaaggagt ttgagctaaa ggtgtgggta tgtgtgtctg atgacttcga tgttgaacga    720
gtgacgaagg caattcttga atcaatcaca tcccgacccg ttcaagtgca ggagtttagt    780
caaattcagc atgatttgag tgagcaatta agaggaaaaa agttttaat cgttttagat     840 gatatctgga acaaagatga ctctgatcta tacgatctct ggacaagact tcaatcccct    900
tttggcatcg gagcaggagg aagtaagatt attgtgacaa cccgtgatgt gaatgttgca    960
aagattatgg gagccactgg agttcataat ttggagtgta tggcagatga tgattgtttg   1020
gaaatatttg agcgacatgc gttcagggga attaatactg gaaagccggt aaattatgat   1080
ttaattaaga caagaattgt tgaaaaatgt cgtggcttac cattagctgc aaggactctc   1140
ggtggtcttt tacgttgcaa agaaaaagat gagtggggag aaatattgaa caacaagtta   1200
tggaatctag cagacaagag tggcattctc cccgtactaa agttgagcta tcactatctt   1260
ccatcaaatt tgaagaggtg ttttgcatat tgctcaatac ttccaaatga ctatgaattt   1320
ggggagaagc agctcattct tttgtggatg gcagagggtt tgattcaaca aaatcctgac   1380
gacaataaac aaatagagga tttgggccgc gactactttc gagagctatt agcaaggtcg   1440
ctgtttcaag aatcaagcaa aaacaattca cgatatgtaa tgcatgacct cgttaatgat   1500
ttagcacaat gggcagcagg tgaaatatgt tttagattgg aagataagca aggtaataac   1560
ttgcaaagca attgctttcg aagggctcgc cattcgtctt tcattgctgg t            1611
```

<210> SEQ ID NO 9
<211> LENGTH: 22
<212> TYPE: DNA
<213> ORGANISM: Artificial
<220> FEATURE:
<223> OTHER INFORMATION: primer

<400> SEQUENCE: 9
tcataattta ccggctttcc tg                                              22

<210> SEQ ID NO 10
<211> LENGTH: 21
<212> TYPE: DNA
<213> ORGANISM: Artificial
<220> FEATURE:
<223> OTHER INFORMATION: primer

<400> SEQUENCE: 10
tctgatgact tcgatgttga a                                               21

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
caccacaaaa agaggcagtg                                                 20

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
cattgctggt cgatttgatg                                           20

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
gcgattcggt ctttctttga                                           20

<210> SEQ ID NO 14
<211> LENGTH: 25
<212> TYPE: DNA
<213> ORGANISM: Artificial
<220> FEATURE:
<223> OTHER INFORMATION: primer

<400> SEQUENCE: 14
ctacaccaaa attgacggca tctgt                                     25

<210> SEQ ID NO 15
<211> LENGTH: 26
<212> TYPE: DNA
<213> ORGANISM: Artificial
<220> FEATURE:
<223> OTHER INFORMATION: primer

<400> SEQUENCE: 15
caaaaaaata cgagcataca gatgcc                                    26

<210> SEQ ID NO 16
<211> LENGTH: 21
<212> TYPE: DNA
<213> ORGANISM: Artificial
<220> FEATURE:
<223> OTHER INFORMATION: primer

<400> SEQUENCE: 16
aaaacattcc tcgacagatg a                                         21

<210> SEQ ID NO 17
<211> LENGTH: 20
<212> TYPE: DNA
<213> ORGANISM: Artificial
<220> FEATURE:
<223> OTHER INFORMATION: primer

<400> SEQUENCE: 17
aggaatcgcg aagtctacca                                           20

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
gcagagcgtg aaattgtgag                                           20

<210> SEQ ID NO 19
<211> LENGTH: 20

```
<212> TYPE: DNA
<213> ORGANISM: Artificial
<220> FEATURE:
<223> OTHER INFORMATION: primer

<400> SEQUENCE: 19
atgacctgcc catctggtaa                                              20

<210> SEQ ID NO 20
<211> LENGTH: 21
<212> TYPE: DNA
<213> ORGANISM: Artificial
<220> FEATURE:
<223> OTHER INFORMATION: primer

<400> SEQUENCE: 20
cttgacccaa accaaaatat g                                            21

<210> SEQ ID NO 21
<211> LENGTH: 21
<212> TYPE: DNA
<213> ORGANISM: Artificial
<220> FEATURE:
<223> OTHER INFORMATION: primer

<400> SEQUENCE: 21
ttgactgttg atcttccctt c                                            21

<210> SEQ ID NO 22
<211> LENGTH: 194
<212> TYPE: PRT
<213> ORGANISM: Malus x domestica

<400> SEQUENCE: 22
```

Met Ala Leu Gly Glu Val Phe Leu Ala Ala Phe Leu Gln Leu Leu Leu
1               5                   10                  15

Asp Arg Leu Thr Pro Arg Glu Ile Leu Glu Tyr Leu Gly Asn Phe Arg
            20                  25                  30

Gly Val Gly Gln Lys Leu Glu Lys Trp Arg Thr Thr Leu Ser Thr Ile
        35                  40                  45

Gly Ala Val Leu Ser Asp Ala Glu Glu Arg Gln Leu Thr Glu Gly Gly
    50                  55                  60

Val Lys Leu Trp Leu Asp Asp Leu Arg Asp Leu Ala Tyr Asp Ile Glu
65                  70                  75                  80

Asp Met Leu Asp Lys Phe Ala Val Lys Met Leu Lys Arg Met Ile Glu
                85                  90                  95

Gly Cys Asp Gln Ala Ser Thr Ser Arg Lys Val Arg Arg Ser Phe Tyr
            100                 105                 110

Lys Val Lys Leu Ser Phe Asp Met Asn Ser Glu Met Lys Lys Ile Thr
        115                 120                 125

Lys Arg Leu Gln Asp Ile Ser Glu Arg Lys Asp Lys Phe Gly Leu Lys
    130                 135                 140

Asp Ile Gly Thr Ser Ala Lys Glu Ser Arg Ser Leu Pro Ser Ser Asp
145                 150                 155                 160

Val Leu Asp Glu Lys Leu Val Val Gly Arg Asp Gly Asp Lys Trp Glu
                165                 170                 175

Ile Ile Glu Leu Leu Ser Lys Lys Tyr Glu His Thr Asp Ala Val Asn
            180                 185                 190

Phe Gly

<210> SEQ ID NO 23
<211> LENGTH: 197
<212> TYPE: PRT
<213> ORGANISM: Arabidopsis thaliana

<400> SEQUENCE: 23

```
Met Thr Gly Ile Gly Glu Met Phe Leu Ala Ala Phe Leu Gln Ala Leu
1               5                   10                  15

Phe Gln Thr Leu Val Ser Glu Pro Phe Arg Ser Phe Lys Arg Arg
            20                  25                  30

Glu Leu Asn Glu Asn Leu Leu Glu Arg Leu Ser Thr Ala Leu Leu Thr
                35                  40                  45

Ile Thr Ala Val Leu Ile Asp Ala Glu Glu Lys Gln Ile Thr Asn Pro
50                  55                  60

Val Val Glu Lys Trp Val Asn Glu Leu Arg Asp Val Val Tyr His Ala
65                  70                  75                  80

Glu Asp Ala Leu Asp Asp Ile Ala Thr Glu Ala Leu Arg Leu Asn Ile
                85                  90                  95

Gly Ala Glu Ser Ser Ser Ser Asn Arg Leu Arg Gln Leu Arg Gly Arg
            100                 105                 110

Met Ser Leu Gly Asp Phe Leu Asp Gly Asn Ser Glu His Leu Glu Thr
        115                 120                 125

Arg Leu Glu Lys Val Thr Ile Arg Leu Glu Arg Leu Ala Ser Gln Arg
    130                 135                 140

Asn Ile Leu Gly Leu Lys Glu Leu Thr Ala Met Ile Pro Lys Gln Arg
145                 150                 155                 160

Leu Pro Thr Thr Ser Leu Val Asp Glu Ser Glu Val Phe Gly Arg Asp
                165                 170                 175

Asp Asp Lys Asp Glu Ile Met Arg Phe Leu Ile Pro Glu Asn Gly Lys
            180                 185                 190

Asp Asn Gly Ile Thr
        195
```

<210> SEQ ID NO 24
<211> LENGTH: 195
<212> TYPE: PRT
<213> ORGANISM: Lycopersicon esclalentum

<400> SEQUENCE: 24

```
Met Glu Ile Gly Leu Ala Val Gly Gly Ala Phe Leu Ser Ser Ala Leu
1               5                   10                  15

Asn Val Leu Phe Asp Arg Leu Ala Pro Asn Gly Asp Leu Leu Asn Met
            20                  25                  30

Phe Arg Lys His Lys Asp His Val Lys Leu Leu Lys Lys Leu Lys Met
        35                  40                  45

Thr Leu Arg Gly Ile Gln Ile Val Leu Ser Asp Ala Glu Asn Lys Gln
    50                  55                  60

Ala Ser Asn Pro Ser Val Arg Asp Trp Leu Asn Glu Leu Arg Asp Ala
65                  70                  75                  80

Val Asp Ser Ala Glu Asn Leu Ile Glu Glu Val Asn Tyr Glu Ala Leu
                85                  90                  95

Arg Leu Lys Val Glu Gly Gln His Gln Asn Phe Ser Glu Thr Ser Asn
            100                 105                 110

Gln Gln Val Ser Asp Asp Phe Phe Leu Asn Ile Lys Asp Lys Leu Glu
        115                 120                 125
```

```
Asp Thr Ile Glu Thr Leu Lys Asp Leu Gln Glu Gln Ile Gly Leu Leu
    130                 135                 140

Gly Leu Lys Glu Tyr Phe Asp Ser Thr Lys Leu Glu Thr Arg Arg Pro
145                 150                 155                 160

Ser Thr Ser Val Asp Asp Glu Ser Asp Ile Phe Gly Arg Gln Ser Glu
                165                 170                 175

Ile Glu Asp Leu Ile Asp Arg Leu Leu Ser Glu Gly Ala Ser Gly Lys
                180                 185                 190

Lys Leu Thr
        195

<210> SEQ ID NO 25
<211> LENGTH: 281
<212> TYPE: PRT
<213> ORGANISM: Oryza sativa

<400> SEQUENCE: 25

Met Glu Glu Val Glu Ala Gly Trp Leu Glu Gly Gly Ile Arg Trp Leu
1               5                   10                  15

Ala Glu Thr Ile Leu Asp Asn Leu Asp Ala Asp Lys Leu Asp Glu Trp
                20                  25                  30

Ile Arg Gln Ile Arg Leu Ala Ala Asp Thr Glu Lys Leu Arg Ala Glu
            35                  40                  45

Ile Glu Lys Val Asp Gly Val Ala Ala Val Lys Gly Arg Ala Ile
    50                  55                  60

Gly Asn Arg Ser Leu Ala Arg Ser Leu Gly Arg Leu Arg Gly Leu Leu
65                  70                  75                  80

Tyr Asp Ala Asp Asp Ala Val Asp Glu Leu Asp Tyr Phe Arg Leu Gln
                85                  90                  95

Gln Gln Val Glu Gly Gly Val Thr Thr Arg Phe Glu Ala Glu Glu Thr
                100                 105                 110

Val Gly Asp Gly Ala Glu Asp Glu Asp Ile Pro Met Asp Asn Thr
            115                 120                 125

Asp Val Pro Glu Ala Val Ala Ala Gly Ser Ser Lys Lys Arg Ser Lys
    130                 135                 140

Ala Trp Glu His Phe Thr Thr Val Glu Phe Thr Ala Asp Gly Lys Asp
145                 150                 155                 160

Ser Lys Ala Arg Cys Lys Tyr Cys His Lys Asp Leu Cys Cys Thr Ser
                165                 170                 175

Lys Asn Gly Thr Ser Ala Leu Arg Asn His Leu Asn Val Cys Lys Arg
                180                 185                 190

Lys Arg Val Thr Ser Thr Asp Gln Pro Val Asn Pro Ser Ser Ala Gly
            195                 200                 205

Glu Gly Ala Ser Asn Ala Thr Gly Asn Ser Val Gly Arg Lys Arg Met
    210                 215                 220

Arg Met Asp Gly Thr Ser Thr His His Glu Ala Val Ser Thr His Pro
225                 230                 235                 240

Trp Asn Lys Ala Glu Leu Ser Asn Arg Ile Gln Cys Met Thr His Gln
                245                 250                 255

Leu Glu Glu Ala Val Asn Glu Val Met Arg Leu Cys Arg Ser Ser Ser
                260                 265                 270

Ser Asn Gln Ser Arg Gln Gly Thr Pro
    275                 280

<210> SEQ ID NO 26
```

```
<211> LENGTH: 200
<212> TYPE: PRT
<213> ORGANISM: Ttiticum aestivicum

<400> SEQUENCE: 26
```

Met Ala Glu Arg Val Val Thr Met Ala Ile Gly Pro Leu Val Ser Met
1               5                   10                  15

Leu Lys Asp Lys Ala Ser Ser Tyr Leu Leu Asp Gln Tyr Lys Val Met
            20                  25                  30

Glu Gly Met Glu Glu Gln His Lys Ile Leu Lys Arg Lys Leu Pro Ala
        35                  40                  45

Ile Leu Asp Val Ile Thr Asp Val Glu Gln Ala Met Ala Gln Arg
    50                  55                  60

Glu Gly Ala Lys Ala Trp Leu Gln Leu Arg Thr Val Ala Tyr Val
65                  70                  75                  80

Ala Asn Glu Val Phe Asp Glu Phe Lys Tyr Glu Ala Leu Arg Arg Glu
                85                  90                  95

Ala Lys Lys Asn Gly His Tyr Ile Lys Leu Gly Phe Asp Val Ile Lys
            100                 105                 110

Leu Phe Pro Thr His Asn Arg Val Ala Phe Arg Tyr Lys Met Gly Arg
        115                 120                 125

Lys Leu Cys Leu Ile Leu Gln Ala Val Glu Val Leu Ile Ala Glu Met
130                 135                 140

Gln Val Phe Gly Phe Lys Tyr Gln Pro Gln Pro Val Ser Lys Glu
145                 150                 155                 160

Trp Arg His Thr Asp Tyr Val Ser Ile Asp Pro Gln Glu Ile Ala Ser
                165                 170                 175

Arg Ser Arg His Glu Asp Lys Lys Asn Ile Ile Gly Ile Leu Val Asp
            180                 185                 190

Glu Ala Ser Asn Ala Asp Leu Thr
        195                 200

```
<210> SEQ ID NO 27
<211> LENGTH: 202
<212> TYPE: PRT
<213> ORGANISM: Oryza sativa

<400> SEQUENCE: 27
```

Met Ala Glu Leu Met Ala Thr Met Val Val Gly Pro Leu Val Ser Met
1               5                   10                  15

Val Lys Glu Lys Ala Ser Ser Tyr Leu Met Glu Gln Tyr Lys Val Met
            20                  25                  30

Glu Gly Met Glu Glu Gln His Lys Ile Leu Lys Arg Lys Leu Pro Ala
        35                  40                  45

Ile Leu Asp Val Ile Ala Asp Ala Glu Glu Gln Ala Ala Lys His Arg
    50                  55                  60

Glu Gly Ala Lys Ala Trp Leu Glu Glu Leu Arg Lys Val Ala Tyr Gln
65                  70                  75                  80

Ala Asn Asp Val Phe Asp Glu Phe Lys Tyr Glu Ala Leu Arg Arg Lys
                85                  90                  95

Ala Lys Ala Asn Trp Gln Tyr Lys Met Leu Gly Met Asp Val Ile Lys
            100                 105                 110

Leu Phe Pro Thr His Asn Arg Ile Val Phe Arg Tyr Arg Met Gly Asn
        115                 120                 125

Lys Leu Arg Met Ile Leu Asn Ala Ile Glu Val Leu Ile Thr Glu Met
130                 135                 140

```
Asn Ala Phe Arg Phe Lys Phe Arg Pro Glu Pro Met Ser Ser Met
145                 150                 155                 160

Lys Trp Arg Lys Thr Asp Ser Lys Ile Ser Glu His Ser Met Asp Ile
                165                 170                 175

Ala Asn Arg Ser Arg Glu Glu Asp Arg Gln Lys Ile Val Lys Ser Leu
            180                 185                 190

Leu Ser Gln Ala Ser Asn Gly Asp Leu Thr
        195                 200

<210> SEQ ID NO 28
<211> LENGTH: 191
<212> TYPE: PRT
<213> ORGANISM: Oryza sativa

<400> SEQUENCE: 28

Met Ala Thr Ser Met Leu Leu Gly Pro Leu Ile Ala Leu Val Asn Arg
1               5                   10                  15

Gln Val Ser Asn Tyr Leu Leu Gln Tyr Gln Glu Leu Asp Gly Met
            20                  25                  30

Glu Glu Gln Leu Thr Ile Leu Glu Arg Lys Leu Pro Ala Ile Leu Asp
        35                  40                  45

Val Ile Ile Asp Ala Glu Gln Gly Thr His Arg Pro Gly Val Ser
50                  55                  60

Ala Trp Leu Lys Ala Leu Lys Ala Val Ala Tyr Lys Ala Asn Asp Ile
65                  70                  75                  80

Phe Asp Glu Phe Lys Tyr Glu Ala Leu Arg Arg Glu Ala Lys Arg Arg
                85                  90                  95

Gly Asn His Gly Asn Leu Ser Thr Ser Ile Val Leu Ala Asn Asn Pro
            100                 105                 110

Leu Val Phe Arg Tyr Arg Met Ser Lys Lys Leu Arg Lys Ile Val Ser
        115                 120                 125

Ser Ile Glu Asp Leu Val Ala Asp Met Asn Ala Phe Gly Phe Arg Tyr
    130                 135                 140

Arg Pro Gln Met Pro Thr Ser Lys Gln Trp Arg Gln Thr Asp Ser Ile
145                 150                 155                 160

Ile Ile Asp Ser Glu Asn Ile Val Ser Arg Glu Lys Glu Lys Gln His
                165                 170                 175

Ile Val Asn Leu Leu Leu Thr Asp Ala Ser Asn Arg Asn Leu Met
            180                 185                 190

<210> SEQ ID NO 29
<211> LENGTH: 343
<212> TYPE: PRT
<213> ORGANISM: Malus x domestica

<400> SEQUENCE: 29

Val Val Ala Ile Val Gly Met Pro Gly Val Gly Lys Thr Thr Leu Ala
1               5                   10                  15

Gln Leu Val Phe Asn Arg Lys Asp Asp Ala Met Lys Glu Phe Glu Leu
            20                  25                  30

Lys Val Trp Val Cys Val Ser Asp Asp Phe Asp Val Glu Arg Val Thr
        35                  40                  45

Lys Ala Ile Leu Glu Ser Ile Thr Ser Arg Pro Val Gln Val Gln Glu
    50                  55                  60

Phe Ser Gln Ile Gln His Asp Leu Ser Glu Gln Leu Arg Gly Lys Lys
65                  70                  75                  80
```

```
Phe Leu Ile Val Leu Asp Asp Ile Trp Asn Lys Asp Ser Asp Leu
                85                  90                  95

Tyr Asp Leu Trp Thr Arg Leu Gln Ser Pro Phe Gly Ile Gly Ala Gly
            100                 105                 110

Gly Ser Lys Ile Ile Val Thr Thr Arg Asp Val Asn Val Ala Lys Ile
        115                 120                 125

Met Gly Ala Thr Gly Val His Asn Leu Glu Cys Met Ala Asp Asp Asp
    130                 135                 140

Cys Leu Glu Ile Phe Glu Arg His Ala Phe Arg Gly Ile Asn Thr Gly
145                 150                 155                 160

Lys Pro Val Asn Tyr Asp Leu Ile Lys Thr Arg Ile Val Glu Lys Cys
                165                 170                 175

Arg Gly Leu Pro Leu Ala Ala Arg Thr Leu Gly Gly Leu Leu Arg Cys
            180                 185                 190

Lys Glu Lys Asp Glu Trp Gly Glu Ile Leu Asn Asn Lys Leu Trp Asn
        195                 200                 205

Leu Ala Asp Lys Ser Gly Ile Leu Pro Val Leu Lys Leu Ser Tyr His
    210                 215                 220

Tyr Leu Pro Ser Asn Leu Lys Arg Cys Phe Ala Tyr Cys Ser Ile Leu
225                 230                 235                 240

Pro Asn Asp Tyr Glu Phe Gly Glu Lys Gln Leu Ile Leu Leu Trp Met
                245                 250                 255

Ala Glu Gly Leu Ile Gln Gln Asn Pro Asp Asp Asn Lys Gln Ile Glu
            260                 265                 270

Asp Leu Gly Arg Asp Tyr Phe Arg Glu Leu Leu Ala Arg Ser Leu Phe
        275                 280                 285

Gln Glu Ser Ser Lys Asn Asn Ser Arg Tyr Val Met His Asp Leu Val
    290                 295                 300

Asn Asp Leu Ala Gln Trp Ala Ala Gly Glu Ile Cys Phe Arg Leu Glu
305                 310                 315                 320

Asp Lys Gln Gly Asn Asn Leu Gln Ser Asn Cys Phe Arg Arg Ala Arg
                325                 330                 335

His Ser Ser Phe Ile Ala Gly
            340

<210> SEQ ID NO 30
<211> LENGTH: 334
<212> TYPE: PRT
<213> ORGANISM: Arabidopsis thaliana

<400> SEQUENCE: 30

Val Val Ala Ile Val Gly Ile Gly Gly Val Gly Lys Thr Thr Leu Ser
1               5                   10                  15

Gln Leu Leu Tyr Asn Asp Gln His Val Arg Ser Tyr Phe Gly Thr Lys
            20                  25                  30

Val Trp Ala His Val Ser Glu Glu Phe Asp Val Phe Lys Ile Thr Lys
        35                  40                  45

Lys Val Tyr Glu Ser Val Thr Ser Arg Pro Cys Glu Phe Thr Asp Leu
    50                  55                  60

Asp Val Leu Gln Val Lys Leu Lys Glu Arg Leu Thr Gly Thr Gly Leu
65                  70                  75                  80

Pro Phe Leu Leu Val Leu Asp Asp Leu Trp Asn Glu Asn Phe Ala Asp
                85                  90                  95

Trp Asp Leu Leu Arg Gln Pro Phe Ile His Ala Ala Gln Gly Ser Gln
```

```
                100             105             110
Ile Leu Val Thr Thr Arg Ser Gln Arg Val Ala Ser Ile Met Cys Ala
            115             120             125

Val His Val His Asn Leu Gln Pro Leu Ser Asp Gly Asp Cys Trp Ser
130             135             140

Leu Phe Met Lys Thr Val Phe Gly Asn Gln Glu Pro Cys Leu Asn Arg
145             150             155             160

Glu Ile Gly Asp Leu Ala Glu Arg Ile Val His Lys Cys Arg Gly Leu
                165             170             175

Pro Leu Ala Val Lys Thr Leu Gly Gly Val Leu Arg Phe Glu Gly Lys
            180             185             190

Val Ile Glu Trp Glu Arg Val Leu Ser Ser Arg Ile Trp Asp Leu Pro
        195             200             205

Ala Asp Lys Ser Asn Leu Leu Pro Val Leu Arg Val Ser Tyr Tyr Tyr
    210             215             220

Leu Pro Ala His Leu Lys Arg Cys Phe Ala Tyr Cys Ser Ile Phe Pro
225             230             235             240

Lys Gly His Ala Phe Glu Lys Asp Lys Val Val Leu Leu Trp Met Ala
                245             250             255

Glu Gly Phe Leu Gln Gln Thr Arg Ser Ser Lys Asn Leu Glu Glu Leu
            260             265             270

Gly Asn Glu Tyr Phe Ser Glu Leu Glu Ser Arg Ser Leu Leu Gln Lys
        275             280             285

Thr Lys Thr Arg Tyr Ile Met His Asp Phe Ile Asn Glu Leu Ala Gln
    290             295             300

Phe Ala Ser Gly Glu Phe Ser Lys Phe Glu Asp Gly Cys Lys Leu
305             310             315             320

Gln Val Ser Glu Arg Thr Arg Tyr Leu Ser Tyr Leu Arg Asp
                325             330

<210> SEQ ID NO 31
<211> LENGTH: 337
<212> TYPE: PRT
<213> ORGANISM: Lycopersicon esclalentum

<400> SEQUENCE: 31

Val Val Pro Ile Val Gly Met Gly Gly Gln Gly Lys Thr Thr Leu Ala
1               5               10              15

Lys Ala Val Tyr Asn Asp Glu Arg Val Lys Asn His Phe Asp Leu Lys
            20              25              30

Ala Trp Tyr Cys Val Ser Glu Gly Phe Asp Ala Leu Arg Ile Thr Lys
        35              40              45

Glu Leu Leu Gln Glu Ile Gly Lys Phe Asp Ser Lys Asp Val His Asn
    50              55              60

Asn Leu Asn Gln Leu Gln Val Lys Leu Lys Ser Leu Lys Gly Lys
65              70              75              80

Lys Phe Leu Ile Val Leu Asp Asp Val Trp Asn Glu Asn Tyr Asn Glu
                85              90              95

Trp Asn Asp Leu Arg Asn Ile Phe Ala Gln Gly Asp Ile Gly Ser Lys
            100             105             110

Ile Ile Val Thr Thr Arg Lys Asp Ser Val Ala Leu Met Met Gly Asn
        115             120             125

Glu Gln Ile Arg Met Gly Asn Leu Ser Thr Glu Ala Ser Trp Ser Leu
    130             135             140
```

Phe Gln Arg His Ala Phe Glu Asn Met Asp Pro Met Gly His Pro Glu
145                 150                 155                 160

Leu Glu Glu Val Gly Arg Gln Ile Ala Ala Lys Cys Lys Gly Leu Pro
                165                 170                 175

Leu Ala Leu Lys Thr Leu Ala Gly Met Leu Arg Ser Lys Ser Glu Val
            180                 185                 190

Glu Glu Trp Lys Arg Ile Leu Arg Ser Glu Ile Trp Glu Leu Pro His
        195                 200                 205

Asn Asp Ile Leu Pro Ala Leu Met Leu Ser Tyr Asn Asp Leu Pro Ala
    210                 215                 220

His Leu Lys Arg Cys Phe Ser Phe Cys Ala Ile Phe Pro Lys Asp Tyr
225                 230                 235                 240

Pro Phe Arg Lys Glu Gln Val Ile His Leu Trp Ile Ala Asn Gly Leu
                245                 250                 255

Val Pro Val Lys Asp Glu Ile Asn Gln Asp Leu Gly Asn Gln Tyr Phe
            260                 265                 270

Leu Glu Leu Arg Ser Arg Ser Leu Phe Glu Lys Val Pro Asn Pro Ser
        275                 280                 285

Lys Arg Asn Ile Glu Glu Leu Phe Leu Met His Asp Leu Val Asn Asp
    290                 295                 300

Leu Ala Gln Leu Ala Ser Ser Lys Leu Cys Ile Arg Leu Glu Glu Ser
305                 310                 315                 320

Gln Gly Ser His Met Leu Glu Gln Cys Arg His Leu Ser Tyr Ser Ile
                325                 330                 335

Gly

<210> SEQ ID NO 32
<211> LENGTH: 345
<212> TYPE: PRT
<213> ORGANISM: Oryza sativa

<400> SEQUENCE: 32

Val Leu Pro Ile Val Gly Asn Gly Gly Ile Gly Lys Thr Thr Leu Ala
1               5                   10                  15

Gln Leu Val Cys Lys Asp Leu Val Ile Lys Ser Gln Phe Asn Val Lys
            20                  25                  30

Ile Trp Val Tyr Val Ser Asp Lys Phe Asp Val Val Lys Ile Thr Arg
        35                  40                  45

Gln Ile Leu Asp His Val Ser Asn Gln Ser His Glu Gly Ile Ser Asn
    50                  55                  60

Leu Asp Thr Leu Gln Gln Asp Leu Glu Glu Gln Met Lys Ser Lys Lys
65                  70                  75                  80

Phe Leu Ile Val Leu Asp Asp Val Trp Glu Ile Arg Thr Asp Asp Trp
                85                  90                  95

Lys Lys Leu Leu Ala Pro Leu Arg Pro Asn Asp Gln Val Asn Ser Ser
            100                 105                 110

Gln Glu Glu Ala Thr Gly Asn Met Ile Ile Leu Thr Thr Arg Ile Gln
        115                 120                 125

Ser Ile Ala Lys Ser Leu Gly Thr Val Gln Ser Ile Lys Leu Glu Ala
    130                 135                 140

Leu Lys Asp Asp Ile Trp Ser Leu Phe Lys Val His Ala Phe Gly
145                 150                 155                 160

Asn Asp Lys His Asp Ser Ser Pro Gly Leu Gln Val Leu Gly Lys Gln
                165                 170                 175

-continued

```
Ile Ala Ser Glu Leu Lys Gly Asn Pro Leu Ala Ala Lys Thr Val Gly
            180                 185                 190

Ser Leu Leu Gly Thr Asn Leu Thr Ile Asp His Trp Asp Ser Ile Ile
        195                 200                 205

Lys Ser Glu Glu Trp Lys Ser Leu Gln Gln Ala Tyr Gly Ile Met Gln
210                 215                 220

Ala Leu Lys Leu Ser Tyr Asp His Leu Ser Asn Pro Leu Gln Gln Cys
225                 230                 235                 240

Val Ser Tyr Cys Ser Leu Phe Pro Lys Gly Tyr Ser Phe Ser Lys Ala
                245                 250                 255

Gln Leu Ile Gln Ile Trp Ile Ala Gln Gly Phe Val Glu Glu Ser Ser
            260                 265                 270

Glu Lys Leu Glu Gln Lys Gly Trp Lys Tyr Leu Ala Glu Leu Val Asn
        275                 280                 285

Ser Gly Phe Leu Gln Gln Val Glu Ser Thr Arg Phe Ser Ser Glu Tyr
    290                 295                 300

Phe Val Met His Asp Leu Met His Asp Leu Ala Gln Lys Val Ser Gln
305                 310                 315                 320

Thr Glu Tyr Ala Thr Ile Asp Gly Ser Glu Cys Thr Glu Leu Ala Pro
                325                 330                 335

Ser Ile Arg His Leu Ser Ile Val Thr
            340                 345

<210> SEQ ID NO 33
<211> LENGTH: 340
<212> TYPE: PRT
<213> ORGANISM: Ttiticum aestivicum

<400> SEQUENCE: 33

Val Val Pro Val Val Ala Met Gly Gly Leu Gly Lys Thr Thr Leu Ala
1               5                   10                  15

Gln Leu Ile Tyr Asn Asp Pro Glu Ile Gln Lys His Phe Gln Leu Leu
            20                  25                  30

Leu Trp Val Cys Val Ser Asp Thr Phe Asp Val Asn Ser Leu Ala Lys
        35                  40                  45

Ser Ile Val Glu Ala Ser Pro Asn Lys Asn Val Asp Thr Asp Lys Pro
    50                  55                  60

Pro Leu Ala Arg Leu Gln Lys Leu Val Ser Gly Gln Arg Tyr Leu Leu
65                  70                  75                  80

Val Leu Asp Asp Val Trp Asp Asn Lys Glu Leu Arg Lys Trp Glu Arg
                85                  90                  95

Leu Lys Val Cys Leu Gln His Gly Gly Met Gly Ser Ala Val Leu Thr
            100                 105                 110

Thr Thr Arg Asp Lys Arg Val Ala Glu Ile Met Gly Ala Asp Arg Ala
        115                 120                 125

Ala Tyr Asn Leu Asn Ala Leu Glu Asp His Phe Ile Lys Glu Ile Ile
    130                 135                 140

Val Asp Arg Ala Phe Ser Ser Glu Asn Gly Lys Ile Pro Glu Leu Leu
145                 150                 155                 160

Glu Met Val Gly Glu Ile Val Lys Arg Cys Cys Gly Ser Pro Leu Ala
                165                 170                 175

Ala Ser Ala Leu Gly Ser Val Leu Arg Thr Lys Thr Thr Val Lys Glu
            180                 185                 190

Trp Asn Ala Ile Ala Ser Arg Ser Ser Ile Cys Thr Glu Glu Thr Gly
        195                 200                 205
```

Ile Leu Pro Ile Leu Lys Leu Ser Tyr Asn Asp Leu Pro Ser His Met
            210                 215                 220

Lys Gln Cys Phe Ala Phe Cys Ala Val Phe Pro Lys Asp Tyr Lys Ile
225                 230                 235                 240

Asp Val Ala Lys Leu Ile Gln Leu Trp Ile Ala Asn Gly Phe Ile Pro
                245                 250                 255

Glu His Lys Glu Asp Ser Leu Glu Thr Ile Gly Gln Leu Ile Phe Asp
            260                 265                 270

Glu Leu Ala Ser Arg Ser Phe Phe Leu Asp Ile Glu Lys Ser Lys Glu
        275                 280                 285

Asp Trp Glu Tyr Tyr Ser Arg Thr Thr Cys Lys Ile His Asp Leu Met
290                 295                 300

His Asp Ile Ala Met Ser Val Met Glu Lys Glu Cys Val Val Ala Thr
305                 310                 315                 320

Met Glu Pro Ser Glu Ile Glu Trp Leu Pro Asp Thr Ala Arg His Leu
                325                 330                 335

Phe Leu Ser Cys
            340

<210> SEQ ID NO 34
<211> LENGTH: 339
<212> TYPE: PRT
<213> ORGANISM: Oryza sativa

<400> SEQUENCE: 34

Val Ile Pro Ile Val Gly Met Gly Gly Met Gly Lys Thr Thr Leu Ala
1               5                   10                  15

Gln Leu Ile Tyr Asn Asp Pro Gln Ile Gln Lys His Phe Gln Leu Leu
            20                  25                  30

Leu Trp Val Cys Val Ser Asp Asn Phe Asp Val Asp Ser Leu Ala Lys
        35                  40                  45

Ser Ile Val Glu Ala Ala Arg Lys Gln Lys Asn Cys Asn Glu Arg Ala
    50                  55                  60

Glu Phe Lys Glu Val Val Asn Gly Gln Arg Phe Leu Leu Val Leu Asp
65                  70                  75                  80

Asp Val Trp Asn Arg Glu Ala Ser Lys Trp Glu Ala Leu Lys Ser Tyr
                85                  90                  95

Val Gln His Gly Gly Ser Gly Ser Ser Val Leu Thr Thr Thr Arg Asp
            100                 105                 110

Lys Thr Val Ala Glu Ile Met Ala Pro Pro Lys Glu Val His His Leu
        115                 120                 125

Lys Asp Leu Asn Glu Asn Phe Ile Lys Glu Ile Ile Glu Arg Ser Ala
    130                 135                 140

Phe Asn Ser Glu Glu Glu Lys Arg Gln Ser Glu Leu Leu Glu Met Val
145                 150                 155                 160

Gly Asp Ile Ala Lys Lys Cys Ser Gly Ser Pro Leu Ala Ala Thr Ala
                165                 170                 175

Leu Gly Ser Thr Leu Arg Thr Lys Thr Lys Lys Glu Trp Glu Ala
            180                 185                 190

Ile Leu Arg Arg Ser Thr Ile Cys Asp Glu Glu Asn Gly Ile Leu Pro
        195                 200                 205

Ile Leu Lys Leu Ser Tyr Asn Cys Leu Pro Ser Tyr Met Arg Gln Cys
    210                 215                 220

Phe Ala Phe Cys Ala Ile Phe Pro Lys Asp His Val Ile Asp Val Glu

```
                225                 230                 235                 240
        Met Leu Ile Gln Leu Trp Met Ala Asn Cys Phe Ile Pro Glu Gln Gln
                        245                 250                 255

Gly Glu Cys Pro Glu Ile Ser Gly Lys Arg Ile Phe Ser Glu Leu Val
                        260                 265                 270

Ser Arg Ser Phe Phe Gln Asp Val Lys Gly Ile Pro Phe Glu Phe His
                        275                 280                 285

Asp Ile Lys Asp Ser Lys Ile Thr Ala Lys Ile His Asp Leu Met His
                        290                 295                 300

Asp Val Ala Gln Ser Ser Met Gly Lys Glu Cys Ala Ala Ile Asp Ser
        305                 310                 315                 320

Glu Ser Ile Gly Ser Glu Asp Phe Pro Tyr Ser Ala Arg His Leu Phe
                        325                 330                 335

Leu Ser Gly

<210> SEQ ID NO 35
<211> LENGTH: 338
<212> TYPE: PRT
<213> ORGANISM: Oryza sativa

<400> SEQUENCE: 35

Val Leu Pro Ile Ile Gly Met Gly Gly Leu Gly Lys Thr Thr Phe Ala
        1               5                   10                  15

Gln Ile Ile Tyr Asn Asp Pro Glu Ile Gln Lys His Phe Gln Leu Arg
                        20                  25                  30

Lys Trp Val Cys Val Leu Asp Asp Phe Asp Val Thr Ser Ile Ala Asn
                        35                  40                  45

Lys Ile Ser Met Ser Ile Glu Lys Glu Cys Glu Asn Ala Leu Glu Lys
                        50                  55                  60

Leu Gln Gln Glu Val Arg Gly Lys Arg Tyr Leu Leu Ile Leu Asp Asp
        65                  70                  75                  80

Val Trp Asn Cys Asp Ala Asp Lys Trp Ala Lys Leu Lys Tyr Cys Leu
                        85                  90                  95

Gln Gln Tyr Gly Gly Val Gly Ser Ala Ile Leu Met Thr Thr Arg Asp
                        100                 105                 110

Gln Gly Val Ala Gln Leu Met Gly Thr Thr Lys Ala His Gln Leu Val
                        115                 120                 125

Arg Met Glu Lys Glu Asp Leu Leu Ala Ile Phe Glu Lys Arg Ala Phe
                        130                 135                 140

Arg Phe Asp Glu Gln Lys Pro Asp Glu Leu Val Gln Ile Gly Trp Glu
        145                 150                 155                 160

Ile Met Asp Arg Cys His Gly Ser Pro Leu Ala Ala Lys Ala Leu Gly
                        165                 170                 175

Ser Met Leu Ser Thr Arg Lys Ala Val Glu Glu Trp Arg Ala Val Leu
                        180                 185                 190

Thr Lys Ser Ser Ile Cys Asp Asp Glu Asn Gly Ile Leu Pro Ile Leu
                        195                 200                 205

Lys Leu Ser Tyr Asp Asp Leu Pro Ser Tyr Met Lys Gln Cys Phe Ala
                        210                 215                 220

Phe Cys Ala Ile Phe Pro Lys Asn Tyr Val Ile Asp Val Glu Met Leu
        225                 230                 235                 240

Ile Leu Leu Trp Met Ala Asn Asp Phe Ile Pro Ser Glu Glu Ala Ile
                        245                 250                 255

Arg Pro Glu Thr Lys Gly Lys Gln Ile Phe Asn Glu Leu Ala Ser Arg
```

```
                    260                 265                 270
Ser Phe Phe Gln Asp Val Lys Glu Val Pro Leu His Lys Asp Glu Ser
            275                 280                 285

Gly His Ser Tyr Arg Thr Ile Cys Ser Ile His Asp Leu Met His Asp
            290                 295                 300

Val Ala Val Ser Val Ile Gly Lys Glu Cys Phe Thr Ile Ala Glu Gly
305                 310                 315                 320

His Asn Tyr Ile Glu Phe Leu Pro Asn Thr Val Arg His Leu Phe Leu
                325                 330                 335

Cys Ser
```

RESISTANCE GENE AND USES THEREOF

CROSS-REFERENCE TO RELATED APPLICATIONS

This application is a National Stage Application filed under 35 U.S.C. §371 of PCT Application No. PCT/NZ2008/000284, filed on Oct. 28, 2008 and published in English on May 7, 2009 as WO 2009/058030, which claims the benefit of New Zealand Application No. 563032, filed Oct. 31, 2007, and New Zealand Application No. 571416, filed Sep. 22, 2008, each of which applications are incorporated by reference in its entirety herein.

TECHNICAL FIELD

The present invention is in the field of disease resistance genes from plants.

BACKGROUND ART

The development of apple (*Malus×domestica*) cultivars carrying natural resistance against major pathogens and pests is a crucial component of any successful breeding strategy. The two most significant fungal diseases of apple are apple scab and powdery mildew. Powdery mildew (caused by *Podosphaera leucotricha*) is a particularly serious problem in relatively dry apple growing areas but is prevalent in all growing regions.

A number of sources of resistance to powdery mildew have been identified in non-commercial apples and breeding to incorporate these resistances into new commercial varieties is in progress using various strategies [11, 13, 26, 27].

Two sources of resistance in particular have been used in a number of different breeding programmes. These sources of powdery mildew resistance are: 1. An open-pollinated seedling of *Malus zumi* (MAL68/5) carrying the Pl2 resistance locus, and 2. An open-pollinated seedling of *Malus robusta* (MAL59/9) carrying the Pl1 resistance locus. Genetic analysis of these sources has indicated that in some genetic backgrounds at least these loci appear to segregate as a single major dominant locus for resistance [10, 24, 29]. Other powdery mildew resistance loci that have been genetically characterized include PlMIS [8], Pld [40], Pl8 [25] and Plw [15]. None of the genes responsible for these resistances have been isolated.

To date, about 70 resistance genes have been cloned from at least 14 different plant species conferring resistance to various diseases [28]. The encoded proteins have been grouped into classes based on a number of characteristic domains.

The first class consists of genes encoding proteins with characteristics of serine/threonine (S/T) kinases. This class includes the first cloned plant disease resistance gene, Pto from tomato [29]. This class also includes two close relatives of the Pto gene, the LhirPto [33] and Fen [30, 34] genes, and the Rpg1 gene [4].

The second class of resistance genes consists of those encoding proteins containing a central nucleotide binding site (NBS) and a carboxy terminal leucine-rich repeat (LRR). The first of these genes to be cloned were the *Arabidopsis thaliana* RPS2 [2] and *Nicotiana tabacum* N [41] genes. The N gene represents the first member of a subclass with Toll-Interleukin-1 like receptor domains at the amino terminus. The RPS2 gene represents the first member of the CC-NBS-LLR subclass with leucine zippers or coiled coil (CC) motifs at the amino terminus. This subclass is sometimes also referred to as non-TIR.

A third major class of resistance genes, the xLRR class, consists of those encoding proteins composed almost entirely of leucine rich repeats (LRRs) that are predicted to reside in an extracellular environment based on their amino acid sequence [21]. The Cf-9 gene [22] was the first gene cloned in this class. Most of the genes in this class have been cloned from tomato (Cf genes) and confer resistance against the leaf mold *Cladosporium fulvum*. The $V_f$ gene from apple confers resistance to apple scab and belongs to the xLRR class of resistance genes [1].

A fourth class of resistance genes consists of those encoding proteins with an amino terminal serine/threonine protein kinase domain with homology to the Pto gene, a carboxy terminal LRR domain with homology to the Cf genes and a central putative transmembrane region [38]. These genes have all the hallmarks of a transmembrane receptor kinase. Receptor kinases are often involved in mammalian ligand mediated signalling (e.g. hormone receptors) with the protein kinase acting as the signalling domain inside the cell and the LRR conferring specificity in the extracellular environment [3]. The Xa21 gene from rice is a member of this class.

A small number of other disease resistance genes that do not fit neatly into one of these four classes have recently been cloned. These include the mlo gene [5] from barley, the $Hs1^{Pro-1}$ gene [6] from sugar beet and the Ve genes [23] from tomato. The mlo gene has a putative 7 transmembrane structure and shares no domains with other cloned resistance genes whereas the $Hs1^{Pro-1}$ gene contains LRRs and the Ve gene contains LRRs, PEST sequences, leucine zippers and potential signals for receptor mediated endocytosis.

Powdery mildew resistance in apple is subject to heterogeneity at the phenotypic, and possibly also genetic, levels. Typically resistant progeny are not reliably identifiable based on nursery phenotypes [20] or using (macroscopic) symptom development in the field. Because of this, resistance is sometimes not scored until the plants have matured in the orchard over several years [10]. This makes the screening for resistance against this important pathogen of apple by traditional means especially difficult and time consuming.

The cloning of a gene for resistance against apple powdery mildew would constitute a significant advance and would have a number of advantages over the traditional breeding routes for resistance.

It is therefore an object of the invention to provide compositions and methods useful for conferring powdery mildew resistance in plants and/or at least to provide the public with a useful choice to this end.

SUMMARY OF THE INVENTION

In the first aspect the invention provides an isolated polynucleotide encoding a polypeptide that comprises the sequence of SEQ ID NO: 1 or a fragment or variant thereof, wherein the fragment or variant confers resistance to powdery mildew in a plant.

Preferably the polypeptide or variant has a sequence characteristic of a non-TIR class disease resistance protein. More preferably the polypeptide or variant has a sequence characteristic of a CC-NBS-LRR class disease resistance protein.

Preferably the fragment comprises sequences characteristic of a coiled coil (CC) domain and a nucleotide binding site (NBS) domain of a non-TIR class disease resistance protein. More preferably the fragment comprises sequences characteristic of a coiled coil (CC) domain and a nucleotide binding site (NBS) domain of a CC-NBS-LRR class disease resistance protein.

Preferably the CC domain is at the N-terminal end of the polypeptide relative to the NBS domain.

In one embodiment the fragment comprises a sequence with at least 70% identity to the sequence of SEQ ID NO: 6.

In a further embodiment the fragment comprises a sequence with at least 70% identity to the sequence of SEQ ID NO: 5.

In a further embodiment the fragment comprises a sequence the sequence of SEQ ID NO: 6.

In a further embodiment the fragment comprises a sequence the sequence of SEQ ID NO: 5.

In a further embodiment the variant comprises a sequence with at least 70% identity to the sequence of SEQ ID NO: 1.

In a further embodiment the polypeptide comprises the sequence of SEQ ID NO: 1.

In a further aspect the invention provides an isolated polynucleotide comprising the sequence of SEQ ID NO: 3 or a fragment or variant thereof, wherein the fragment or variant encodes a polypeptide that confers resistance to powdery mildew in a plant.

Preferably the polynucleotide or variant encodes a polypeptide with a sequence characteristic of a non-TIR class disease resistance protein. More preferably the polypeptide has a sequence characteristic of a CC-NBS-LRR class disease resistance protein.

Preferably the fragment encodes a polypeptide comprising sequences characteristic of a coiled coil (CC) domain and a nucleotide binding site (NBS) domain of a non-TIR class disease resistance protein. More preferably the fragment encodes a polypeptide comprising sequences characteristic of a coiled coil (CC) domain and a nucleotide binding site (NBS) domain of a CC-NBS-LRR class disease resistance protein.

Preferably the CC domain is at the N-terminal end of the polypeptide relative to the NBS domain.

In one embodiment the fragment comprises a sequence with at least 70% sequence identity to SEQ ID NO: 8.

In one embodiment the fragment comprises a sequence with at least 70% sequence identity to SEQ ID NO: 7.

In a further embodiment the fragment comprises the sequence of SEQ ID NO: 8.

In a further embodiment the fragment comprises the sequence of SEQ ID NO: 7.

In one embodiment the variant comprises a sequence with at least 70% sequence identity to sequence of SEQ ID NO: 3.

In a further embodiment the polynucleotide comprises the sequence of SEQ ID NO: 3.

In a further embodiment the variant comprises a sequence with at least 70% sequence identity to the sequence of SEQ ID NO: 2.

In a further embodiment the polynucleotide comprises the sequence of SEQ ID NO: 2.

In a further aspect the invention provides an isolated polypeptide comprising the amino acid sequence of SEQ ID NO: 1, or a fragment or variant thereof, wherein the fragment or variant confers resistance to powdery mildew in a plant.

Preferably the polypeptide or variant has a sequence characteristic of a non-TIR class disease resistance protein.

More preferably the polypeptide or variant has a sequence characteristic of a CC-NBS-LRR class disease resistance protein.

Preferably the fragment comprises sequences characteristic of a coiled coil (CC) domain and a nucleotide binding site (NBS) domain of a non-TIR class disease resistance protein. More preferably the fragment comprises sequences characteristic of a coiled coil (CC) domain and a nucleotide binding site (NBS) domain of a CC-NBS-LRR class disease resistance protein.

Preferably the CC domain is at the N-terminal end relative to the NBS domain.

In one embodiment the fragment comprises a sequence with at least 70% identity to the sequence of SEQ ID NO: 6.

In a further embodiment the fragment comprises a sequence with at least 70% identity to the sequence of SEQ ID NO: 5.

In a further embodiment the fragment comprises the sequence of SEQ ID NO: 6.

In a further embodiment the fragment comprises the sequence of SEQ ID NO: 5.

In a further embodiment the variant comprises a sequence with at least 70% identity to the sequence of SEQ ID NO: 1.

In a further embodiment the polypeptide comprises the sequence of SEQ ID NO: 1.

In a further aspect the invention provides an isolated polynucleotide encoding a polypeptide that comprises the sequence of SEQ ID NO: 6 or a variant thereof, wherein the variant confers resistance to powdery mildew in a plant.

Preferably the polypeptide or variant comprises sequences characteristic of a coiled coil (CC) domain and a nucleotide binding site (NBS) domain of a non-TIR class disease resistance protein. More preferably the fragment comprises sequences characteristic of a coiled coil (CC) domain and a nucleotide binding site (NBS) domain of a CC-NBS-LRR class disease resistance protein.

In one embodiment the variant comprises a sequence with at least 70% identity to the sequence of SEQ ID NO: 6.

In a further embodiment the variant comprises a sequence with at least 70% identity to the sequence of SEQ ID NO: 5.

In a further embodiment the polypeptide comprises the sequence of SEQ ID NO: 6.

In a further embodiment the polypeptide comprises the sequence of SEQ ID NO: 5.

In a further embodiment the polypeptide comprises a sequence with at least 70% identity to the sequence of SEQ ID NO: 1.

Preferably the polypeptide encodes a polypeptide with sequences characteristic of a CC-NBS-LRR class disease resistance protein.

In a further embodiment the polypeptide comprises the sequence of SEQ ID NO: In a further aspect the invention provides an isolated polynucleotide comprising the sequence of SEQ ID NO: 8 or a variant thereof, wherein the variant encodes a polypeptide that confers resistance to powdery mildew in a plant.

Preferably the polypeptide comprises sequences characteristic of a coiled coil (CC) and nucleotide binding site (NBS) domain of a non-TIR class disease resistance protein. More preferably the polypeptide comprises sequences characteristic of a coiled coil (CC) and a nucleotide binding site domain of a CC-NBS-LRR class disease resistance protein.

Preferably the CC domain is at the N-terminal end relative to the NBS domain.

In one embodiment the variant comprises a sequence with at least 70% sequence identity to the sequence of SEQ ID NO: 8.

In one embodiment the polynucleotide comprises a sequence with at least 70% sequence identity to the sequence of SEQ ID NO: 7.

In one embodiment the polynucleotide comprises the sequence of SEQ ID NO: 8.

In one embodiment the polynucleotide comprises the sequence of SEQ ID NO: 7.

In one embodiment the polynucleotide comprises a sequence with at least 70% sequence identity to the sequence of SEQ ID NO: 1.

In one embodiment the polynucleotide comprises a sequence with at least 70% sequence identity to the sequence of SEQ ID NO: 2.

In one embodiment the polynucleotide comprises the sequence of SEQ ID NO: 1.

In one embodiment the polynucleotide comprises the sequence of SEQ ID NO: 2.

In a further aspect the invention provides an isolated polypeptide comprising the amino acid sequence of SEQ ID NO: 6, or a variant thereof, wherein the variant confers resistance to powdery mildew in a plant.

Preferably the variant comprises sequences characteristic of a coiled coil (CC) and a nucleotide binding site (NBS) domain of a non-TIR class disease resistance protein. More preferably the polypeptide comprises sequences characteristic of a coiled coil (CC) and a nucleotide binding site domain of a CC-NBS-LRR class disease resistance protein.

Preferably the CC domain is at the N-terminal end relative to the NBS domain.

In one embodiment the variant comprises a sequence with at least 70% identity to the sequence of SEQ ID NO: 6.

In a further embodiment the polypeptide comprises a sequence with at least 70% identity to the sequence of SEQ ID NO: 5.

In a further embodiment the polypeptide comprises a sequence with at least 70% identity to the sequence of SEQ ID NO: 1.

Preferably the polypeptide comprises sequences characteristic of a CC-NBS-LRR class disease resistance protein.

In a further embodiment the polypeptide comprises the sequence of SEQ ID NO: 6.

In a further embodiment the polypeptide comprises the sequence of SEQ ID NO: 5.

In a further embodiment the polypeptide comprises the sequence of SEQ ID NO: 1.

In a further aspect the invention provides an isolated polynucleotide encoding a polypeptide of the invention.

In a further aspect the invention provides an isolated polynucleotide comprising:
 a) a polynucleotide comprising a fragment, of at least 15 nucleotides in length, of a polynucleotide of the invention;
 b) a polynucleotide comprising a complement, of at least 15 nucleotides in length, of the polynucleotide of the invention; or
 c) a polynucleotide comprising a sequence, of at least 15 nucleotides in length, capable of hybridising to the polynucleotide of the invention under stringent hybridisation conditions.

In a further aspect the invention provides a genetic construct which comprises a polynucleotide of the invention.

In a further aspect the invention provides an expression construct which comprises a polynucleotide of the invention.

In a further aspect the invention provides an RNAi construct which comprises a polynucleotide of the invention.

In a further aspect the invention provides a vector comprising an expression construct, genetic construct or RNAi construct of the invention.

In a further aspect the invention provides a host cell comprising an expression construct or genetic construct of the invention.

In a further aspect the invention provides a host cell genetically modified to express a polynucleotide or polypeptide of the invention.

Preferably the host cell is genetically modified to express a polynucleotide encoding a polypeptide that confers powdery mildew resistance on a plant.

In a further aspect the invention provides a plant cell which comprises an expression construct, genetic construct or RNAi construct of the invention.

In a further aspect the invention provides a plant cell genetically modified to express a polynucleotide of the invention, or a polypeptide of the invention.

Preferably the plant cell is genetically modified to express a polynucleotide encoding a polypeptide that confers powdery mildew resistance on a plant.

In a further aspect the invention provides a plant which comprises a plant cell of the invention.

Preferably the plant has increased resistance to powdery mildew.

In a further aspect the invention provides a method for producing a plant cell or plant with increased resistance to powdery mildew, the method comprising transformation of a plant cell or plant with a polynucleotide encoding polypeptide with the amino acid sequence of SEQ ID NO: 1 or a fragment or variant thereof, wherein the fragment or variant confers resistance to powdery mildew in a plant.

Preferably the polypeptide has a sequence characteristic of a CC-NBS-LRR class disease resistance protein.

Preferably the fragment comprises sequences characteristic of a coiled coil (CC) domain and a nucleotide binding site (NBS) domain of a non-TIR class disease resistance protein. More preferably the polypeptide comprises sequences characteristic of a coiled coil (CC) and a nucleotide binding site domain of a CC-NBS-LRR class disease resistance protein.

In one embodiment the fragment comprises a sequence with at least 70% identity to the sequence of SEQ ID NO: 6.

In a further embodiment the fragment comprises a sequence with at least 70% identity to the sequence of SEQ ID NO: 5.

In a further embodiment the fragment comprises the sequence of SEQ ID NO: 6.

In a further embodiment the fragment comprises a sequence the sequence of SEQ ID NO: 5.

In a further embodiment the variant comprises a sequence with at least 70% identity to the sequence of SEQ ID NO: 1.

In a further embodiment the polypeptide comprises the sequence of SEQ ID NO: 1.

In a further aspect the invention provides a method for producing a plant cell or plant with increased resistance to powdery mildew, the method comprising transformation of a plant cell or plant with a polynucleotide comprising the sequence of SEQ ID NO: 3 or a fragment or variant thereof, wherein the fragment or variant encodes a protein that confers powdery mildew resistance in a plant.

Preferably the polypeptide has a sequence characteristic of a CC-NBS-LRR class disease resistance protein.

In one embodiment the fragment comprises a sequence with at least 70% sequence identity to SEQ ID NO: 8.

In one embodiment the fragment comprises a sequence with at least 70% sequence identity to SEQ ID NO: 7.

In a further embodiment the fragment comprises the sequence of SEQ ID NO: 8.

In a further embodiment the fragment comprises the sequence of SEQ ID NO: 7.

In one embodiment the variant comprises a sequence with at least 70% sequence identity to sequence of SEQ ID NO: 3.

In a further embodiment the polynucleotide comprises the sequence of SEQ ID NO: 3.

In a further embodiment the variant comprises a sequence with at least 70% sequence identity to the sequence of SEQ ID NO: 2.

In a further embodiment the polynucleotide comprises the sequence of SEQ ID NO: 2.

In a further aspect the invention provides a method for producing a plant cell or plant with increased resistance to powdery mildew, the method comprising transformation of a plant cell or plant with a polynucleotide encoding polypeptide with the amino acid sequence of SEQ ID NO: 6 or a variant thereof, wherein the variant confers resistance to powdery mildew in a plant.

Preferably the variant comprises sequence characteristic of a coiled coil (CC) domain and a nucleotide binding site (NBS) domain of a CC-NBS-LRR class disease resistance protein.

In one embodiment the variant comprises a sequence with at least 70% identity to the sequence of SEQ ID NO: 6.

In a further embodiment the polypeptide comprises a sequence with at least 70% identity to the sequence of SEQ ID NO: 5.

In a further embodiment the polypeptide comprises the sequence of SEQ ID NO: 6.

In a further embodiment the polypeptide comprises the sequence of SEQ ID NO: 5.

In a further embodiment the polypeptide comprises a sequence with at least 70% identity to the sequence of SEQ ID NO: 1.

Preferably the variant encodes a polypeptide with sequences characteristic of a CC-NBS-LRR class disease resistance protein.

In a further embodiment the polypeptide comprises the sequence of SEQ ID NO: 1.

In a further aspect the invention provides a method for producing a plant cell or plant with increased resistance to powdery mildew, the method comprising transformation of a plant cell or plant with a polynucleotide comprising the sequence of SEQ ID NO: 8 or a variant thereof, wherein the variant encodes a polypeptide that confers powdery mildew resistance in a plant.

Preferably the polypeptide comprises sequences characteristic of a coiled coil (CC) domain and a nucleotide binding site (NBS) domain of a CC-NBS-LRR class disease resistance protein.

Preferably the CC domain is at the N-terminal end of the protein relative to the NBS domain.

In one embodiment the variant comprises a sequence with at least 70% sequence identity to the sequence of SEQ ID NO: 8.

In one embodiment the polynucleotide comprises a sequence with at least 70% sequence identity to the sequence of SEQ ID NO: 7.

In one embodiment the polynucleotide comprises a sequence with at least 70% sequence identity to the sequence of SEQ ID NO: 1.

In one embodiment the polynucleotide comprises a sequence with at least 70% sequence identity to the sequence of SEQ ID NO: 2.

In one embodiment the variant comprises the sequence of SEQ ID NO: 8.

In one embodiment the polynucleotide comprises the sequence of SEQ ID NO: 7.

In one embodiment the polynucleotide comprises the sequence of SEQ ID NO: 1.

In one embodiment the polynucleotide comprises the sequence of SEQ ID NO: 2.

In a further aspect the invention provides a method for selecting a plant with increased resistance to powdery mildew, the method comprising testing of a plant for altered expression of a polynucleotide of the invention.

In a further aspect the invention provides a method for selecting a plant with increased resistance to powdery mildew, the method comprising testing of a plant for altered expression of a polypeptide of the invention.

In a further aspect the invention provides a plant cell or plant produced by the method of the invention. Preferably the plant is genetically modified to include a polynucleotide or polypeptide of the invention.

In a further aspect the invention provides a group of plants selected by the method of the invention.

In a further aspect the invention provides an antibody raised against a polypeptide of the invention.

The polynucleotides and variants of polynucleotides, of the invention may be derived from any species. The polynucleotides and variants may also be recombinantly produced and also may be the products of "gene shuffling' approaches.

In one embodiment the polynucleotide or variant, is derived from a plant species.

In a further embodiment the polynucleotide or variant, is derived from a gymnosperm plant species.

In a further embodiment the polynucleotide or variant, is derived from an angiosperm plant species.

In a further embodiment the polynucleotide or variant, is derived from a monocotyledonous plant species.

In a further embodiment the polynucleotide or variant, is derived from a dicotyledonuous plant species.

The polypeptides and variants of polypeptides of the invention may be derived from any species. The polypeptides and variants may also be recombinantly produced and may also be expressed from the products of "gene shuffling' approaches.

In one embodiment the polypeptides or variants of the invention are derived from plant species.

In a further embodiment the polypeptides or variants of the invention are derived from gymnosperm plant species.

In a further embodiment the polypeptides or variants of the invention are derived from angiosperm plant species.

In a further embodiment the polypeptides or variants of the invention are derived from monocotyledonous plant species.

In a further embodiment the polypeptides or variants of the invention are derived from dicotyledonous plant species.

The plant cells and plants of the invention, including those from which the polynucleotides, variant polynucleotides, polypeptide and variant polypeptides may be derived, and including plant cells and plants to be transformed or selected, may be from any species.

In one embodiment the plant cells and plants are from gymnosperm species.

In a further embodiment the plant cells and plants are from an angiosperm species.

In a further embodiment the plant cells and plants are from a dicotyledonuous species.

In a further embodiment the plant cells and plants are from a fruit species selected from a group comprising but not limited to the following genera: *Actinidia, Malus, Citrus, Fragaria, Vaccinium, Pyrus, Prunus, Rosa, Fragaria, Rubus, Cydonia Eriobotya, Mespilus, Photinia, Pyracantha, Sorbus, Humus, Ficus, Morus, Ulmus, Cucumus, Cucurbita, Arachis, Cicer, Lupinus, Cyamopsis, Lotus, Glycine, Phaseolus, Vigna, Medicago, Trifolium, Pisum, Vicia, Betula, Fagus, Juglans, Ricinus, Manihot, Hevea, Euphorbia, Saliceae.*

Particularly preferred fruit plant species are: *Actidinia deliciosa, A. chinensis, A. eriantha, A. arguta,* hybrids of the four *Actinidia* species, *Malus domestica, Malus zumi, Malus sylvestris, Malus sieversii* and *Malus sieboldii.*

The most preferred plant family is the Rosaceae.

The most preferred genus is *Malus*.

The most preferred *Malus* species are *Malus zumi* and *Malus domestica*.

In a further embodiment the plant cells and plants are from a vegetable species selected from a group comprising but not limited to the following genera: *Brassica, Lycopersicon* and *Solanum*.

Particularly preferred vegetable plant species are: *Lycopersicon esculentum* and *Solanum tuberosum*.

In a further embodiment the plant cells and plants of the invention are from monocotyledonous species.

In a further embodiment the plant cells and plants are from a crop species selected from a group comprising but not limited to the following genera: *Glycine, Zea, Hordeum* and *Oryza*.

Particularly preferred crop plant species are: *Oryza sativa, Glycine max* and *Zea mays*.

DETAILED DESCRIPTION

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

Polynucleotides and Fragments

The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments.

A "fragment" of a polynucleotide sequence provided herein is a subsequence of the polynucleotide sequence consisting of a contiguous stretch of nucleotides of the polynucleotide sequence, e.g., a sequence that is at least 15 nucleotides in length. The fragments of the invention preferably comprise at least 15 nucleotides, preferably at least 20 nucleotides, more preferably at least 30 nucleotides, more preferably at least 50 nucleotides, more preferably at least 50 nucleotides and most preferably at least 60 nucleotides of contiguous nucleotides of a polynucleotide of the invention. A fragment of a polynucleotide sequence can be used in antisense, gene silencing, triple helix or ribozyme technology, or as a primer, a probe, included in a microarray, or used in polynucleotide-based selection methods of the invention.

The term "primer" refers to a short polynucleotide, usually having a free 3' OH group, that is hybridized to a template and used for priming polymerization of a polynucleotide complementary to the target.

The term "probe" refers to a short polynucleotide that is used to detect a polynucleotide sequence, that is complementary to the probe, in a hybridization-based assay. The probe may consist of a "fragment" of a polynucleotide as defined herein.

Polypeptides and Fragments

The term "polypeptide", as used herein, encompasses amino acid chains of any length but preferably at least 5 amino acids, including full-length proteins, in which amino acid residues are linked by covalent peptide bonds. Polypeptides of the present invention may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof.

A "fragment" of a polypeptide is a subsequence of the longer polypeptide, consisting of a contiguous stretch of amino acids of the longer polypeptide, that performs a function that is required for the biological activity and/or provides three dimensional structure of the longer polypeptide. The term may refer to a polypeptide, an aggregate of a polypeptide such as a dimer or other multimer, a fusion polypeptide, a polypeptide fragment, a polypeptide variant, or derivative thereof capable of performing the above enzymatic activity.

The term "isolated" as applied to the polynucleotide or polypeptide sequences disclosed herein is used to refer to sequences that are removed from their natural cellular environment. An isolated molecule may be obtained by any method or combination of methods including biochemical, recombinant, and synthetic techniques.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

The term "derived from" with respect to polynucleotides or polypeptides of the invention being derived from a particular genus or species, means that the polynucleotide or polypeptide has the same sequence as a polynucleotide or polypeptide found naturally in that genus or species. The polynucleotide or polypeptide, derived from a particular genus or species, may therefore be produced synthetically or recombinantly.

Variants

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. Variants may also be naturally occurring or non-naturally occurring recombinants between alleles of these homologues, paralogues and orthologues. In certain embodiments, variants of the inventive polypeptides and polypeptides possess biological activities that are the same or similar to those of the inventive polypeptides or polypeptides. The term "variant" with reference to polypeptides and polypeptides encompasses all forms of polypeptides and polypeptides as defined herein.

Polynucleotide Variants

Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequence of the present invention. Identity is found over a comparison window of at least 20 nucleotide positions, preferably at least 50 nucleotide positions, more preferably at least 100 nucleotide positions, and most preferably over the entire length of a polynucleotide of the invention.

Polynucleotide sequence identity can be determined in the following manner. The subject polynucleotide sequence is compared to a candidate polynucleotide sequence using BLASTN (from the BLAST suite of programs, version 2.2.5 [November 2002]) in bl2seq (Tatiana A. Tatusova, Thomas L. Madden (1999), "Blast 2 sequences—a new tool for comparing protein and nucleotide sequences", FEMS Microbiol Lett. 174:247-250), which is publicly available from NCBI. The default parameters of bl2seq are utilized except that filtering of low complexity parts should be turned off.

The identity of polynucleotide sequences may be examined using the following unix command line parameters:

bl2seq -i nucleotideseq1 -j nucleotideseq2 -F F -p blastn

The parameter -F F turns off filtering of low complexity sections. The parameter -p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48,443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp. 276-277) which can be obtained from the internet (hgmp.mrc.ac.uk site, Software/EMBOSS). The European Bioinformatics Institute server also provides the facility to perform EMBOSS-needle global alignments between two sequences on line at "ebi.ac.uk/emboss/align".

Alternatively the GAP program may be used which computes an optimal global alignment of two sequences without penalizing terminal gaps. GAP is described in the following paper: Huang, X. (1994) On Global Sequence Alignment. Computer Applications in the Biosciences 10, 227-235.

A preferred method for calculating polynucleotide % sequence identity is based on aligning sequences to be compared using Clustal X (Jeanmougin et al., 1998, *Trends Biochem. Sci.* 23, 403-5.)

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI via the internet.

The similarity of polynucleotide sequences may be examined using the following unix command line parameters:

bl2seq -i nucleotideseq1 -j nucleotideseq2 -F F -p tblastx

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than $1\times10^{-6}$ more preferably less than $1\times10^{-9}$, more preferably less than $1\times10^{-12}$, more preferably less than $1\times10^{-15}$, more preferably less than $1\times10^{-18}$, more preferably less than $1\times10^{-21}$, more preferably less than $1\times10^{-30}$, more preferably less than $1\times10^{-40}$, more preferably less than $1\times10^{-50}$, more preferably less than $1\times10^{-60}$, more preferably less than $1\times10^{-70}$, more preferably less than $1\times10^{-80}$, more preferably less than $1\times10^{-90}$ and most preferably less than $1\times10^{-100}$ when compared with any one of the specifically identified sequences.

Alternatively, variant polynucleotides of the present invention hybridize to the specified polynucleotide sequences, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing,). Tm for polynucleotide molecules greater than about 100 bases can be calculated by the formula Tm=81.5+0.41% (G+C-log(Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 by is reduced by approximately (500/oligonucleotide length)° C.

With respect to the DNA mimics known as peptide nucleic acids (PNAs) (Nielsen et al., Science. 1991 Dec. 6; 254(5037):1497-500) Tm values are higher than those for DNA-DNA or DNA-RNA hybrids, and can be calculated using the formula described in Giesen et al., Nucleic Acids Res. 1998 Nov. 1; 26(21):5004-6. Exemplary stringent hybridization conditions for a DNA-PNA hybrid having a length less than 100 bases are 5 to 10° C. below the Tm.

Variant polynucleotides of the present invention also encompasses polynucleotides that differ from the sequences of the invention but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available bl2seq program from the BLAST suite of programs (version 2.2.5 [November 2002]) from NCBI via the internet and the tblastx algorithm as previously described.

Polypeptide Variants

The term "variant" with reference to polypeptides encompasses naturally occurring, recombinantly and synthetically produced polypeptides. Variant polypeptide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequences of the present invention. Identity is found over a comparison window of at least 20 amino acid positions, preferably at least 50 amino acid positions, more preferably at least 100 amino acid positions, and most preferably over the entire length of a polypeptide of the invention.

Polypeptide sequence identity can be determined in the following manner. The subject polypeptide sequence is compared to a candidate polypeptide sequence using BLASTP (from the BLAST suite of programs, version 2.2.5 [November 2002]) in bl2seq, which is publicly available via the internet from NCBI. The default parameters of bl2seq are utilized except that filtering of low complexity regions should be turned off.

Polypeptide sequence identity may also be calculated over the entire length of the overlap between a candidate and subject polynucleotide sequences using global sequence alignment programs. EMBOSS-needle (available at on the internet, supra) and GAP (Huang, X. (1994) On Global Sequence Alignment. Computer Applications in the Biosciences 10, 227-235) as discussed above are also suitable global sequence alignment programs for calculating polypeptide sequence identity.

A preferred method for calculating polypeptide % sequence identity is based on aligning sequences to be compared using Clustal X (Jeanmougin et al., 1998, *Trends Biochem. Sci.* 23, 403-5.)

Polypeptide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) via the internet from NCBI. The similarity of polypeptide sequences may be examined using the following unix command line parameters:

```
bl2seq-i peptideseq1-j peptideseq2 -F F-p blastp
```

Variant polypeptide sequences preferably exhibit an E value of less than $1\times10^{-6}$ more preferably less than $1\times10^{-9}$, more preferably less than $1\times10^{-12}$, more preferably less than $1\times10^{-15}$, more preferably less than $1\times10^{-18}$, more preferably less than $1\times10^{-21}$, more preferably less than $1\times10^{-30}$, more preferably less than $1\times10^{-40}$, more preferably less than $1\times10^{-50}$, more preferably less than $1\times10^{-60}$, more preferably less than $1\times10^{-70}$, more preferably less than $1\times10^{-80}$, more preferably less than $1\times10^{-90}$ and most preferably $1\times10^{-100}$ when compared with any one of the specifically identified sequences.

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

The function of a polypeptide variant in conferring resistance to powdery mildew may be assessed by the methods described in the Example section herein.

Constructs, Vectors and Components Thereof

The term "genetic construct" refers to a polynucleotide molecule, usually double-stranded DNA, which may have inserted into it another polynucleotide molecule (the insert polynucleotide molecule) such as, but not limited to, a cDNA molecule or a molecule derived from genomic DNA region covering, but not restricted to, the open reading frame and any introns and exons within that region. A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA or be expressed transiently. The genetic construct may be linked to a vector.

The term "vector" refers to a polynucleotide molecule, usually double stranded DNA, which is used to transport the genetic construct into a host cell. The vector may be capable of replication in at least one additional host system, such as E. coli.

The term "expression construct" refers to a genetic construct that includes the necessary elements that permit transcribing the insert polynucleotide molecule, and, optionally, translating the transcript into a polypeptide. An expression construct typically comprises in a 5' to 3' direction:
  a) a promoter functional in the host cell into which the construct will be transformed,
  b) the polynucleotide to be expressed, and
  c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence is identified by the presence of a 5' translation start codon and a 3' translation stop codon. When inserted into a genetic construct, a "coding sequence" is capable of being expressed when it is operably linked to promoter and terminator sequences.

"Operably-linked" means that the sequenced to be expressed is placed under the control of regulatory elements that include promoters, tissue-specific regulatory elements, temporal regulatory elements, enhancers, repressors and terminators.

The term "noncoding region" refers to untranslated sequences that are upstream of the translational start site and downstream of the translational stop site. These sequences are also referred to respectively as the 5' UTR and the 3' UTR. These regions include elements required for transcription initiation and termination and for regulation of translation efficiency.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to nontranscribed cis-regulatory elements upstream of the coding region that regulate gene transcription. Promoters comprise cis-initiator elements which specify the transcription initiation site and may include conserved boxes such as the TATA box, and motifs that are bound by transcription factors.

A "transgene" is a polynucleotide that is taken from one organism and introduced into a different organism by transformation. The transgene may be derived from the same species or from a different species as the species of the organism into which the transgene is introduced.

An "inverted repeat" is a sequence that is repeated, where the second half of the repeat is in the complementary strand, e.g.,

```
(5')GATCTA . . . TAGATC(3')

(3')CTAGAT . . . ATCTAG(5')
```

Read-through transcription will produce a transcript that undergoes complementary base-pairing to form a hairpin structure provided that there is a 3-5 by spacer between the repeated regions.

Host Cells

Host cells may be derived from, for example, bacterial, fungal, insect, mammalian or plant organisms.

A "transgenic plant" refers to a plant which contains new genetic material as a result of genetic manipulation or transformation. The new genetic material may be derived from a plant of the same species as the resulting transgenic plant or from a different species.

The applicants have identified a novel gene (SEQ ID NO: 2) that encodes a novel polypeptide (SEQ ID NO: 1) that confers powdery mildew resistance to a plant. SEQ ID NO: 3 shows the cDNA/open reading frame encoding the novel polypeptide of SEQ ID NO: 1.

The applicants have also shown that a polynucleotide sequence encoding a truncated polypeptide comprising just the coiled coil (CC) domain and the nucleotide binding site (NBS) domain is sufficient to confer powdery mildew resistance to a plant.

The invention provides genetic constructs, vectors comprising the polynucleotides, including polynucleotides encoded the truncated polypeptide. The invention provides genetically modified host cells, plant cells and plants containing the novel polynucleotide sequences, genetic constructs and vectors. The invention also provides plants comprising the plant cells of the invention.

The invention provides plants altered in resistance to powdery mildew, relative to suitable control plants. The invention provides plants with increased resistance to powdery mildew.

The invention also provides methods for the production of such plants, and methods of selection of such plants.

The term "powdery mildew" as used herein refers to the commonly known disease of several plant species caused by organisms selected from but not limited to the following genera *Podosphaera, Blumeria, Arthrocladiella, Brasiliomyces, Caespitotheca, Cystotheca, Erysiphe, Golovinomyces, Leveillula, Microsphaera, Neoerysiphe, Oidiopsis, Oidium, Ovulariopsis, Parauncinula, Phyllactinia, Pleochaeta, Reticuloidium, Sawadaea, Sphaerotheca, Typhulochaeta* and *Uncinula*.

Preferably the causative pathogen is from the genus *Podosphaera*.

Preferably the causative pathogen is from the species *Podosphaera leucotricha*.

The term "increased resistance to powdery mildew" means that the plants of the invention, or plants produced or selected by the methods of the invention show reduced symptoms of powdery mildew infection, when challenged with causative pathogens, than do control plants under the same conditions.

Suitable control plants include non-transformed plants of the same species or variety or plants transformed with control constructs, such as, for example, empty vector constructs.

With respect to the selection methods of the invention, suitable control plants include non-selected members of the population from which selected plants are selected.

Methods for Isolating or Producing Polynucleotides

The polynucleotide molecules of the invention can be isolated by using a variety of techniques known to those of ordinary skill in the art. By way of example, such polypeptides can be isolated through use of the polymerase chain reaction (PCR) described in Mullis et al., Eds. 1994 The Polymerase Chain Reaction, Birkhauser, incorporated herein by reference. The polypeptides of the invention can be amplified using primers, as defined herein, derived from the polynucleotide sequences of the invention.

Further methods for isolating polynucleotides of the invention include use of all, or portions of, the polypeptides having the sequence set forth herein as hybridization probes. The technique of hybridizing labelled polynucleotide probes to polynucleotides immobilized on solid supports such as nitrocellulose filters or nylon membranes, can be used to screen a genomic or cDNA libraries. Exemplary hybridization and wash conditions are: hybridization for 20 hours at 65° C. in 5. 0×SSC, 0.5% sodium dodecyl sulfate, 1×Denhardt's solution; washing (three washes of twenty minutes each at 55° C.) in 1.0×SSC, 1% (w/v) sodium dodecyl sulfate, and optionally one wash (for twenty minutes) in 0.5×SSC, 1% (w/v) sodium dodecyl sulfate, at 60° C. An optional further wash (for twenty minutes) can be conducted under conditions of 0.1×SSC, 1% (w/v) sodium dodecyl sulfate, at 60° C.

The polynucleotide fragments of the invention may be produced by techniques well-known in the art such as restriction endonuclease digestion, oligonucleotide synthesis and PCR amplification.

A partial polynucleotide sequence may be used, in methods well-known in the art to identify the corresponding full length polynucleotide sequence. Such methods include PCR-based methods, 5'RACE (Frohman M A, 1993, Methods Enzymol. 218: 340-56) and hybridization-based method, computer/database-based methods. Further, by way of example, inverse PCR permits acquisition of unknown sequences, flanking the polynucleotide sequences disclosed herein, starting with primers based on a known region (Triglia et al., 1998, *Nucleic Acids Res* 16, 8186, incorporated herein by reference). The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. Additionally when down-regulation of a gene is the desired result, it may be necessary to utilise a sequence identical (or at least highly similar) to that in the plant, for which reduced expression is desired. For these reasons among others, it is desirable to be able to identify and isolate orthologues of a particular gene in several different plant species.

Variants (including orthologues) may be identified by the methods described herein.

Methods for Identifying Variants

Physical Methods

Variant polypeptides may be identified using PCR-based methods (Mullis et al., Eds. 1994 The Polymerase Chain Reaction, Birkhauser). Typically, the polynucleotide sequence of a primer, useful to amplify variants of polynucleotide molecules of the invention by PCR, may be based on a sequence encoding a conserved region of the corresponding amino acid sequence.

Alternatively library screening methods, well known to those skilled in the art, may be employed (Sambrook et al., Molecular Cloning: A Laboratory Manual, 2nd Ed. Cold Spring Harbor Press, 1987). When identifying variants of the probe sequence, hybridization and/or wash stringency will typically be reduced relatively to when exact sequence matches are sought.

Polypeptide variants may also be identified by physical methods, for example by screening expression libraries using antibodies raised against polypeptides of the invention (Sambrook et al., Molecular Cloning: A Laboratory Manual, 2nd Ed. Cold Spring Harbor Press, 1987) or by identifying polypeptides from natural sources with the aid of such antibodies.

Computer Based Methods

The variant sequences of the invention, including both polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29: 1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [November 2002]) including BLASTN, BLASTP, BLASTX, tBLASTN and tBLASTX, which are publicly available from NCBI on the internet or from the National Center for Biotechnology Information (NCBI), National Library of Medicine, Building 38A, Room 8N805, Bethesda, Md. 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25: 3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research, 22:4673-4680 or on the internet, address www-igbmc.u-strasbg.fr/BioInfo/ClustalW/Top or T-COFFEE (Cedric Notredame, Desmond G. Higgins, Jaap Heringa, T-Coffee: A novel method for fast and accurate multiple sequence alignment, J. Mol. Biol. (2000) 302: 205-217)) or PILEUP, which uses progressive, pairwise alignments (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

Coiled-coil (CC) regions within proteins can be detected by utilising the programme Pepcoil (Lupas A, van Dyke M & Stock J 1991. Science 252:1162-1164) which calculates probablilities that particular windows of 28 amino acid residues will form a coiled-coil structure.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (www.expasy.org/prosite) contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

The function of a variant polynucleotide of the invention as encoding a polypeptide conferring resistance to powdery mildew can be analysed by methods disclosed herein and well known to those skilled in the art. Such methods may involve transforming susceptible plants with polynucleotides of the invention and testing the resistance of transformed plants to challenge with powdery mildew pathogens. Such methods are described in the Examples section of this specification.

Methods for Isolating Polypeptides

The polypeptides of the invention, including variant polypeptides, may be prepared using peptide synthesis methods well known in the art such as direct peptide synthesis using solid phase techniques (e.g. Stewart et al., 1969, in Solid-Phase Peptide Synthesis, WH Freeman Co, San Francisco Calif., or automated synthesis, for example using an Applied Biosystems 431A Peptide Synthesizer (Foster City, Calif.). Mutated forms of the polypeptides may also be produced during such syntheses.

The polypeptides and variant polypeptides of the invention may also be purified from natural sources using a variety of techniques that are well known in the art (e.g. Deutscher, 1990, Ed, Methods in Enzymology, Vol. 182, *Guide to Protein Purification*,).

Alternatively the polypeptides and variant polypeptides of the invention may be expressed recombinantly in suitable host cells and separated from the cells as discussed below.

Methods for Producing Constructs and Vectors

The genetic constructs of the present invention comprise one or more polynucleotide sequences of the invention and/or polynucleotides encoding polypeptides of the invention, and may be useful for transforming, for example, bacterial, fungal, insect, mammalian or plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Polynucleotides, Constructs or Vectors The invention provides a host cell which comprises a genetic construct or vector of the invention.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987; Ausubel et al., Current Protocols in Molecular. Biology, Greene Publishing, 1987) for recombinant production of polypeptides of the invention. Such methods may involve the culture of host cells in an appropriate medium in conditions suitable for, or conducive to, expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Methods for Producing Plant Cells and Plants Comprising Constructs and Vectors

The invention further provides plant cells which comprise a genetic construct of the invention, and plant cells modified to alter expression of a polynucleotide or polypeptide of the invention. Plants comprising such cells also form an aspect of the invention.

Methods for transforming plant cells, plants and portions thereof with polypeptides are described in Draper et al., 1988, Plant Genetic Transformation and Gene Expression. A Laboratory Manual, Blackwell Sci. Pub. Oxford, p. 365; Potrykus and Spangenburg, 1995, Gene Transfer to Plants. Springer-Verlag, Berlin.; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

Methods for Genetic Manipulation of Plants

A number of plant transformation strategies are available (e.g. Birch, 1997, Ann Rev Plant Phys Plant Mol Biol, 48, 297, Hellens R P, et al (2000) Plant Mol Biol 42: 819-32, Hellens R et al Plant Meth 1: 13). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. The expressed polynucleotide/polypeptide may be derived from the plant species to be transformed or may be derived from a different plant species.

Transformation strategies may be designed to reduce expression of a polynucleotide/polypeptide in a plant cell, tissue, organ or at a particular developmental stage which/when it is normally expressed. Such strategies are known as gene silencing strategies.

Genetic constructs for expression of genes in transgenic plants typically include promoters for driving the expression of one or more cloned polynucleotide, terminators and selectable marker sequences to detect the presence of the genetic construct in the transformed plant.

The promoters suitable for use in the constructs of this invention are functional in a cell, tissue or organ of a monocot or dicot plant and include cell-, tissue- and organ-specific promoters, cell cycle specific promoters, temporal promoters, inducible promoters, constitutive promoters that are active in most plant tissues, and recombinant promoters. Choice of promoter will depend upon the temporal and spatial expression of the cloned polynucleotide, so desired. The promoters may be those normally associated with a transgene of interest, or promoters which are derived from genes of other plants, viruses, and plant pathogenic bacteria and fungi. Those skilled in the art will, without undue experimentation, be able to select promoters that are suitable for use in modifying and modulating plant traits using genetic constructs comprising the polynucleotide sequences of the invention. Examples of constitutive plant promoters include the CaMV 35S promoter, the nopaline synthase promoter and the octopine synthase promoter, and the Ubi 1 promoter from maize. Plant promoters which are active in specific tissues, respond to internal developmental signals or external abiotic or biotic stresses are described in the scientific literature. Exemplary promoters are described, e.g., in WO 02/00894, which is herein incorporated by reference.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zein gene terminator, the *Oryza sativa* ADP-glucose pyrophosphorylase terminator and the *Solanum tuberosum* PI-II terminator.

Selectable markers commonly used in plant transformation include the neomycin phophotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenberg. Eds) Springer Verlag. Berline, pp. 325-336.

Gene silencing strategies may be focused on the gene itself or regulatory elements which effect expression of the encoded polypeptide. "Regulatory elements" is used here in the widest possible sense and includes other genes which interact with the gene of interest.

Genetic constructs designed to decrease or silence the expression of a polynucleotide/polypeptide of the invention may include an antisense copy of a polynucleotide of the invention. In such constructs the polynucleotide is placed in an antisense orientation with respect to the promoter and terminator.

An "antisense" polynucleotide is obtained by inverting a polynucleotide or a segment of the polynucleotide so that the transcript produced will be complementary to the mRNA transcript of the gene, e.g.,

```
5'GATCTA 3'        3'CTAGAT 5'
(coding strand)    (antisense strand)

3'CUAGAU 5' mRNA   5'GAUCUCG 3' antisense RNA
```

Genetic constructs designed for gene silencing may also include an inverted repeat. An 'inverted repeat' is a sequence that is repeated where the second half of the repeat is in the complementary strand, e.g.,

```
5'-GATCTA . . . TAGATC-3'
3'-CTAGAT . . . ATCTAG-5'
```

The transcript formed may undergo complementary base pairing to form a hairpin structure. Usually a spacer of at least 3-5 by between the repeated region is required to allow hairpin formation.

Another silencing approach involves the use of a small antisense RNA targeted to the transcript equivalent to an miRNA (Llave et al., 2002, Science 297, 2053). Use of such small antisense RNA corresponding to polynucleotide of the invention is expressly contemplated.

The term genetic construct as used herein also includes small antisense RNAs and other such polypeptides effecting gene silencing.

Transformation with an expression construct, as herein defined, may also result in gene silencing through a process known as sense suppression (e.g. Napoli et al., 1990, Plant Cell 2, 279; de Carvalho Niebel et al., 1995, Plant Cell, 7, 347). In some cases sense suppression may involve overexpression of the whole or a partial coding sequence but may also involve expression of non-coding regions of the gene, such as an intron or a 5' or 3' untranslated region (UTR). Chimeric partial sense constructs can be used to coordinately silence multiple genes (Abbott et al., 2002, Plant Physiol. 128(3): 844-53; Jones et al., 1998, Planta 204: 499-505). The use of such sense suppression strategies to silence the expression of a polynucleotide of the invention is also contemplated.

The polynucleotide inserts in genetic constructs designed for gene silencing may correspond to coding sequence and/or non-coding sequence, such as promoter and/or intron and/or 5' or 3' UTR sequence, or the corresponding gene.

Other gene silencing strategies include dominant negative approaches and the use of ribozyme constructs (McIntyre, 1996, Transgenic Res, 5, 257)

Pre-transcriptional silencing may be brought about through mutation of the gene itself or its regulatory elements. Such mutations may include point mutations, frameshifts, insertions, deletions and substitutions.

The following are representative publications disclosing genetic transformation protocols that can be used to genetically transform the following plant species: Rice (Alam et al., 1999, Plant Cell Rep. 18, 572); apple (Yao et al., 1995, Plant Cell Reports 14, 407-412); maize (U.S. Pat. Nos. 5,177,010 and 5,981,840); wheat (Ortiz et al., 1996, Plant Cell Rep. 15, 1996, 877); tomato (U.S. Pat. No. 5,159,135); potato (Kumar et al., 1996 Plant J. 9: 821); cassava (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Nos. 5,846,797 and 5,004,863); grasses (U.S. Pat. Nos. 5,187,073 and 6,020,539); peppermint (Niu et al., 1998, Plant Cell Rep. 17, 165); citrus plants (Pena et al., 1995, Plant Sci. 104, 183); caraway (Krens et al., 1997, Plant Cell Rep, 17, 39); banana (U.S. Pat. No. 5,792,935); soybean (U.S. Pat. Nos. 5,416, 011; 5,569,834; 5,824,877; 5,563,04455 and 5,968,830); pineapple (U.S. Pat. No. 5,952,543); poplar (U.S. Pat. No. 4,795,855); monocots in general (U.S. Pat. Nos. 5,591,616 and 6,037,522); *brassica* (U.S. Pat. Nos. 5,188,958; 5,463, 174 and 5,750,871); cereals (U.S. Pat. No. 6,074,877); pear (Matsuda et al., 2005, Plant Cell Rep. 24(1):45-51); *Prunus* (Ramesh et al., 2006 Plant Cell Rep. 25(8):821-8; Song and Sink 2005 Plant Cell Rep. 2006; 25(2):117-23; Gonzalez Padilla et al., 2003 Plant Cell Rep. 22(1):38-45); strawberry (Oosumi et al., 2006 Planta. 223(6):1219-30; Folta et al., 2006 Planta April 14; PMID: 16614818), rose (Li et al., 2003), *Rubus* (Graham et al., 1995 Methods Mol. Biol. 1995; 44:129-33), tomato (Dan et al., 2006, Plant Cell Reports V25:432-441), and *Actinidia eriantha* (Wang et al., 2006, Plant Cell Rep. 25, 5: 425-31). Transformation of other species is also contemplated by the invention. Suitable methods and protocols are available in the scientific literature.

Several further methods known in the art may be employed to alter expression of a nucleotide and/or polypeptide of the invention. Such methods include but are not limited to Tilling (Till et al., 2003, Methods Mol Biol, 2%, 205), so called "Deletagene" technology (Li et al., 2001, Plant Journal 27(3), 235) and the use of artificial transcription factors such as synthetic zinc finger transcription factors. (e.g. Jouvenot et al., 2003, Gene Therapy 10, 513). Additionally antibodies or fragments thereof, targeted to a particular polypeptide may also be expressed in plants to modulate the activity of that polypeptide (Jobling et al., 2003, Nat. Biotechnol., 21(1), 35). Transposon tagging approaches may also be applied. Additionally peptides interacting with a polypeptide of the invention may be identified through technologies such as phase-display (Dyax Corporation). Such interacting peptides may be expressed in or applied to a plant to affect activity of a polypeptide of the invention. Use of each of the above approaches in alteration of expression of a nucleotide and/or polypeptide of the invention is specifically contemplated.

The terms "to alter expression of" and "altered expression" of a polynucleotide or polypeptide of the invention, are intended to encompass the situation where genomic DNA corresponding to a polynucleotide of the invention is modified thus leading to altered expression of a polynucleotide or polypeptide of the invention. Modification of the genomic DNA may be through genetic transformation or other methods known in the art for inducing mutations. The "altered expression" can be related to an increase or decrease in the amount of messenger RNA and/or polypeptide produced and may also result in altered activity of a polypeptide due to alterations in the sequence of a polynucleotide and polypeptide produced.

Methods of Selecting Plants

Methods are also provided for selecting plants with altered resistance to powdery mildew. Such methods involve testing of plants for altered expression of a polynucleotide or polypeptide of the invention. Such methods may be applied at a young age or early developmental stage when the altered resistance to powdery mildew may not necessarily be easily measurable.

The expression of a polynucleotide, such as a messenger RNA, is often used as an indicator of expression of a corresponding polypeptide. Exemplary methods for measuring the expression of a polynucleotide include but are not limited to Northern analysis, RT-PCR and dot-blot analysis (Sambrook et al., Molecular Cloning: A Laboratory Manual, 2nd Ed. Cold Spring Harbor Press, 1987). Polynucleotides or portions of the polynucleotides of the invention are thus useful as probes or primers, as herein defined, in methods for the identification of plants with altered powdery mildew resistance. The polynucleotides of the invention may be used as probes in hybridization experiments, or as primers in PCR based experiments, designed to identify such plants.

Alternatively antibodies may be raised against polypeptides of the invention. Methods for raising and using antibodies are standard in the art (see for example: Antibodies, A Laboratory Manual, Harlow A Lane, Eds, Cold Spring Harbour Laboratory, 1998). Such antibodies may be used in methods to detect altered expression of polypeptides which modulate powdery mildew resistance in plants. Such methods may include ELISA (Kemeny, 1991, A Practical Guide to ELISA, N.Y. Pergamon Press) and Western analysis (Towbin & Gordon, 1994, J Immunol Methods, 72, 313).

These approaches for analysis of polynucleotide or polypeptide expression and the selection of plants with altered resistance to powdery mildew are useful in conventional breeding programs designed to produce resistant varieties.

Plants

The term "plant" is intended to include a whole plant, any part of a plant, propagules and progeny of a plant.

The term 'propagule' means any part of a plant that may be used in reproduction or propagation, either sexual or asexual, including seeds and cuttings.

The plants of the invention may be grown and either selfed or crossed with a different plant strain and the resulting hybrids, with the desired phenotypic characteristics, may be identified. Two or more generations may be grown to ensure that the subject phenotypic characteristics are stably maintained and inherited. Plants resulting from such standard breeding approaches also form an aspect of the present invention.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

BRIEF DESCRIPTION OF THE DRAWINGS

The present invention will be better understood with reference to the accompanying drawings in which:

FIG. 1 shows a Southern blot analysis of genomic DNA from a test population of powdery mildew resistant and susceptible parents and progeny of the cross 'Royal Gala' X A689-24. DNA samples were digested with DraI, and the Southern blot hybridized with the mf1c9 (NBS) probe. Lane 1; Powdery mildew (PM) resistant parent A689-24. lane 2; PM susceptible parent 'Royal Gala'. lanes 3-5; PM resistant progeny. lanes 6-8; PM susceptible progeny. Two polymorphic restriction fragments (approximately 5.7 kb and 5.5 kb in size) putatively segregating with the resistance phenotype are shown by arrows.

FIG. 2A shows a diagram of a Southern blot analysis of restriction fragment sizes in the cosmid clone pk4-051-2N. DNA of the cosmid clone was cut with the restriction endonucleases indicated, separated by gel electrophoresis, transferred to N+ nylon membrane and probed with the NBS clone mf1c9. Lane 1; ApaI, lane 2; BamHI, lane 3; DraI lane 4; EcoRV, lane 5; KpnI, lane 6; SalI, lane 7; SpeI, lane 8; XhoI, lane 9; NotI and SpeI, lane 10; NotI and XhoI, lane 11; HindIII endonuclease digest of Lambda marker. Three fragments that were subcloned are indicated with white arrows.

FIG. 2B shows a schematic diagram of the restriction sites, coding region and surrounding sequenced region of the Pl2.1 candidate gene. The 4.1 kb open reading frame is shown as a grey box and the sequenced 8.5 kb AvrII genomic DNA fragment containing a small 95 by intron (light grey), the 4.4 kb cDNA fragments and a scale bar of 2 kb in dark grey are indicated below the figure. Restriction endonuclease sites; P; SpeI, A; AvrII, D; DraI, X; XhoI, V; EcoRV, S; SacI, B; BamHI. The dotted line indicates the position of the 2NA fragment used as a probe in subsequent analysis.

FIG. 3 shows DNA sequence (SEQ ID NO:2) and translation (SEQ ID NO:1) of the Pl2.1 candidate gene region. Based on comparisons between cDNA and genomic sequence, an intron in the 5' UTR is shown in grey and the deduced translation of an uninterupted 1367 residue open reading frame is shown from base 2788 to base 6891 with the amino acid translation shown in bold as an additional line below the corresponding DNA sequence. Underlined regions mark the position of the Pl2.1 primers used in the analysis. As named in the text they are given in the following order; 5'UTR, Pl2.1 5' utr F1, Pl2.1 rt 5'F1, Pl2.1 5' CCF1 and Pl2.1 3' CCR1 (overlapping in sequence and indicated within the same region), F2 P2N, R2 P2N, R1-2NA, F1-2NA, Pl2.1 3' utr R1 and 3'UTR respectively. Two XmnI restriction sites used to develop the deletion construct are italicized at positions 4796-4805 and 6156-6165.

FIG. 4 shows an RFLP linkage analysis with an internal fragment of the cosmid pk051-2N resistance gene candidate Pl2.1 A. Southern blot of EcoRV digested genomic DNA probed with the 2NA internal fragment of the cosmid R gene candidate. lane 1-1 kb marker lane 2; the susceptible parent 'Royal Gala'; lane 3—the resistant parent A689-24; lanes 4 to 9—susceptible progeny; lanes 10 to 19-resistant progeny; note that the progeny in lane 6 was subsequently identified as a probable rogue based on microsatellite analysis. The two arrows on the right mark two polymorphic restriction fragment (approximately 4.9 kb and 4.7 kb in size) segregating with the resistance phenotype. B. Segregation analysis in the 'Pinkie' X 'Braeburn' population. Southern blot of genomic DNA cut with the restriction endonuclease DraI and probed with the 2NA fragment produced by PCR amplification of the corresponding region from the cosmid clone with primers F1-2NA and R12NA. Lane 1; 1 kb marker, lane 2; Lambda HindIII marker, lane 3; 'Pinkie', lane 4; 'Braeburn', lane 5; A689-24, lane 6 to lane 16; progeny of the 'Pinkie' X 'Braeburn' population. Three black arrows on the left indicate RFLPs segregating as a closely linked set and including two RFLPs of identical size segregating with resistance in the 'Royal Gala' X A689-24 population, the top fragment indicated by the arrows does not segregate in the 'Royal Gala' X A689-24 population, but segregates in a 3:1 ratio in the 'Pinkie' X 'Braeburn' population.

FIG. 5A shows an analysis of meiotic cross-over events in the region of the Pl2 resistance gene. DNA samples of progeny were analysed with the genetic markers indicated below. Key; AC, the SCAR marker NZscOPAC15/AZ16; Pl2 the powdery mildew (cumulative) resistance phenotype; N18, U2, and S5, the SCAR markers OPN18, NZscOPUO2 and S5 respectively; XO the actual number of cross-overs characterized in the region indicated by the filled in box. An estimated distance based on the % of deduced cross-overs is given in italics below the diagram and the black bar indicates the region expanded in FIG. 5B. Note that the distance was calculated based on the proportion of cross-overs in the total number of progeny fully characterized for the flanking markers concerned—in the case of region A that was 217 progeny, for regions B and C that was the full dataset of 443 progeny, and for region D that was 190 progeny.

FIG. 5B shows a more detailed analysis of meiotic cross-over events in the region between N18 and the Pl2 resistance gene. Key; as for FIG. 5A; RV, the 4.9 kb and 4.7 kb EcoRV restriction fragment markers, SNP, the SNP marker derived from the Pl2.1 candidate gene (note although this marker is shown to the right of the Pl2 gene it could be on either side of this gene or in the gene itself). An estimated distance based on the % of deduced cross-overs is given in italics below the diagram, the distance between the SNP marker and the Pl2 gene is underlined. Note that the distance was calculated based on the proportion of cross-overs in the following way—in the case of region B1 cross-overs in the full dataset of 443 progeny, for region B2 the proportion of cross-overs in a subset of 13 progeny with cross-overs between OPN18 and the resistance gene which were also analysed for the presence of the EcoRV RFLP markers (note that 7 progeny with possible gene conversion events involving this region were not counted), and for region C1 based on finding no progeny with cross-overs between the SNP marker and the powdery mildew phenotype out of 411 that were analysed for the SNP marker, the flanking NZscOPU02 and OPN18 markers and the powdery mildew phenotype (cumulative) score.

Figure 6A:
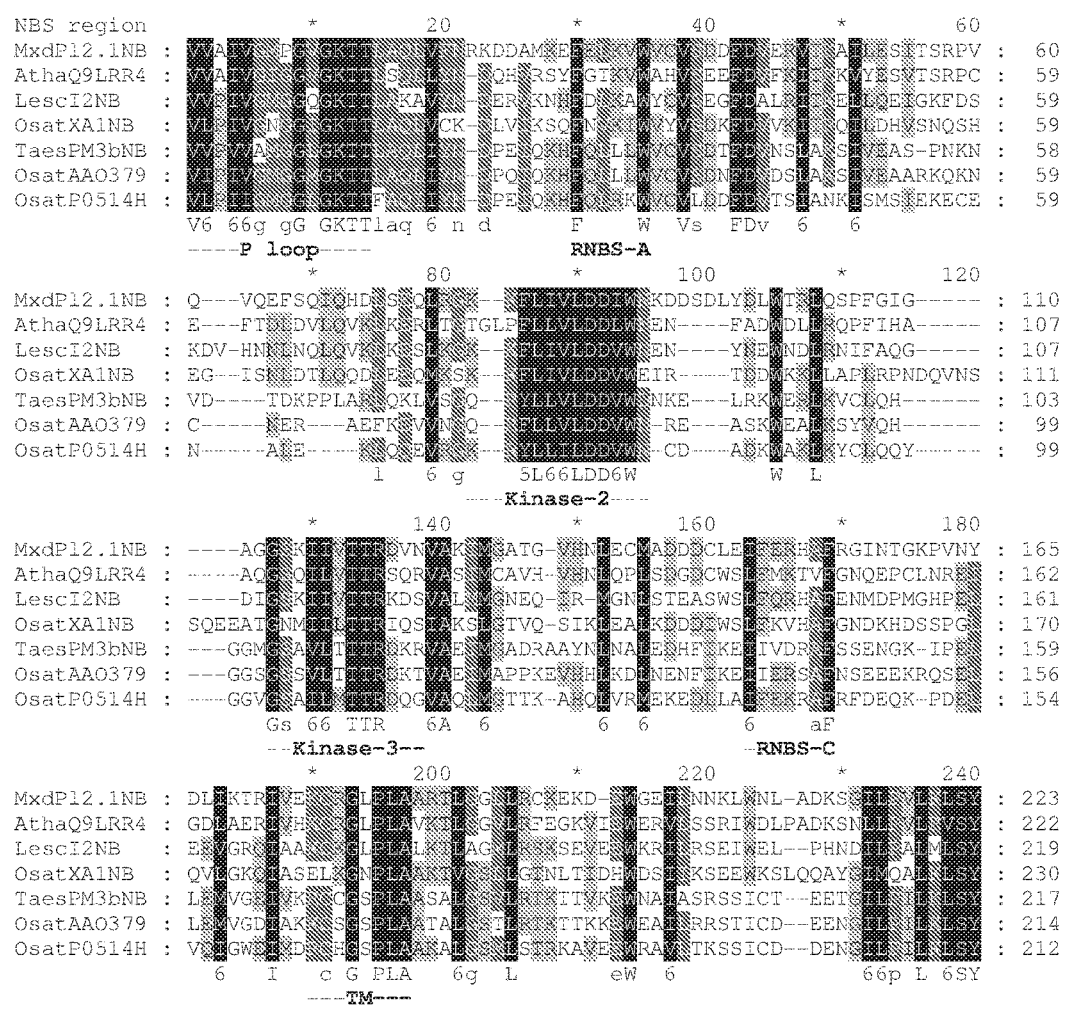

FIG. 6A shows alignments of the MxdPl2.1 protein with known resistance genes and candidate genes from other plants. The N terminal CC region and the central NBS region sequences were aligned using the Gonnet scoring matrix and the complete alignment option in ClustalX [39] which compares all sequences by pairwise alignments, constructs a dendrogram and then performs the final multiple alignment using the dendrogram as a guide. Alignments are displayed using Genedoc [31]. The consensus protein sequence is shown under the alignment with similarity groups used (1=DN 2=EQ 3=ST 4=KR 5=FYW 6=ILVM). Characteristic motifs in the CC and NBS regions are indicated in bold below the consensus sequence, dashes being used to indicate the approximate length of the motifs. Genbank sequence identifications for abbreviations in the alignment; MxdPl21 the apple Pl2.1 candidate gene CC region (SEQ ID NO:22), AthaQ9LRR4 (*Arabidopsis*, Q9LRR4) CC region (SEQ ID NO:23), Lescl2 CC region (tomato, AAD27815) (SEQ ID NO:24), TaesPM3b CC region (wheat, AAQ96158) (SEQ ID NO:26), OsatXA1 CC region (rice, BAA25068) (SEQ ID NO:25), OsatAAO379 CC region (rice, AAO37954) (SEQ ID NO:27), OsatP0514H (rice, BAD52970) (SEQ ID NO:28). Genbank sequence identifications for abbreviations in the alignment; MxdPl21 the apple Pl2.1 candidate gene NBS region (SEQ ID NO:29), AthaQ9LRR4 NBS region (*Arabidopsis*, Q9LRR4) (SEQ ID NO:30), Lescl2 NBS region (tomato, AAD27815) (SEQ ID NO:31), TaesPM3b NBS region (wheat, AAQ96158) (SEQ ID NO:32), OsatXA1 NBS region (rice, BAA25068) (SEQ ID NO:33), OsatAAO379 NBS region (rice, AAO37954) (SEQ ID NO:34), OsatP0514H NBS region (rice, BAD52970) (SEQ ID NO:35).

FIG. 6B shows alignment of the 32 putative leucine rich repeats (LRR) in Pl2.1 to each other, alignments were performed by matching the repeats to the LRR core LXX-LXLXXC/N consensus sequence shown above the first deduced LRR. The short remaining C terminal sequence is also shown after the deduced LRR 32. C) adjusted alignments were converted into phylogenetic trees using ClustalX [39], bootstrapped 1000 times and drawn by NJ plot [32], trees display bootstrap values and the bar in the right hand corner is a scale for branch lengths. Abbreviations as for A) with an additional motif identifier at the end of the name; CC signifies the coiled coil region, NB signifies the nucleotide binding site region and LRR signifies the leucine rich repeat region. The beginning and end of the region deleted in the Pl2 deletion construct are underlined in LRR 5 and LRR 23 respectively. For each of the LRRs, the amino acid coordinates within SEQ ID NO:1 are as follows:
LRR1, amino acids 550-577;
LRR2 amino acids 578-603:
LRR3, amino acids 604-626;
LRR4, amino acids 627-646;
LRR5, amino acids 647-674;
LRR6, amino acids 675-703;
LRR7, amino acids 704-729;
LRR8, amino acids 730-759;
LRR9, amino acids 760-786;
LRR10, amino acids 787-807;
LRR11, amino acids 808-834;
LRR12, amino acids 835-864;
LRR13, amino acids 865-888;
LRR14, amino acids 889-908;
LRR15, amino acids 909-932;
LRR16, amino acids 933-958;
LRR17, amino acids 959-985;
LRR18, amino acids 986-1017;
LRR19, amino acids 1018-1041;
LRR20, amino acids 1042-1064;
LRR21, amino acids 1065-1089;
LRR22, amino acids 1090-1108;
LRR23, amino acids 1109-1127;
LRR24, amino acids 1128-1152;
LRR25, amino acids 1153-1178;
LRR26, amino acids 1179-1202;
LRR27, amino acids 1203-1223;
LRR28, amino acids 1224-1243;
LRR29, amino acids 1244-1273;
LRR30, amino acids 1274-1298;
LRR31, amino acids 1299-1320;
LRR32, amino acids 1321-1342; and
remainder, amino acids 1343-1367.

Figure 7:
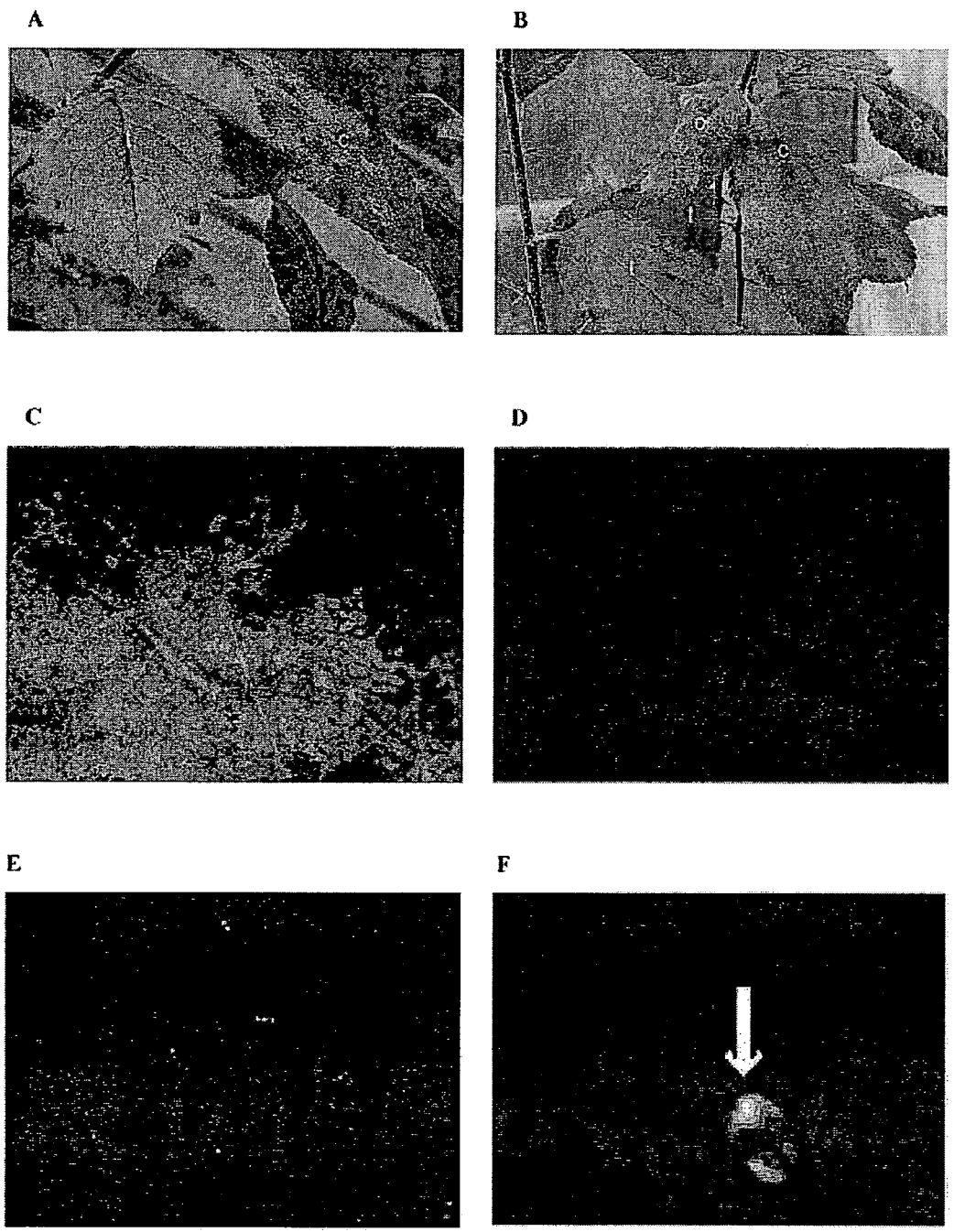

FIG. 7 shows macroscopic and microscopic reactions on untransformed 'Royal Gala' and Pl2.1 transgenic 'Royal Gala' plants infected with powdery mildew. A)-B) Macroscopic symptoms on control (c) untransformed and transformed (t) 'Royal Gala' C)-E) microscopic symptoms and reactions with a scale bar showing size. C) Abundant hyphal growth on 'Royal Gala' untransformed youngest leaves (leaf 1-20). D) Line A24 Youngest leaves (leaf 1-20) almost no spores visible. E) Line A24 middle of the plant (leaves 20-40) with spores visible but mostly not germinated. F) Line A24, 12× magnified view of un-germinated powdery mildew spore marked with arrow from view E).

FIG. 8 microscopic reactions on transformed Pl2.1 transgenic 'Royal Gala' plants infected with powdery mildew (scale bar shown). A) Line 24 field of view with no visible hypersensitive response (HR) reactions on older leaves (leaf 40-80). B)-F) fields of view with HR reactions on older leaves (leaf 40-80). B) Line A24, showing a chain of HR reactions associated with hyphae more easily visible in another plane of view. C) Line A7, showing a hypha closely associated with a single HR reaction. D) Line A7, the same view taken at different exposure and plane of view to highlight the presence of a hypha protruding from the main hyphal branch down to the HR reaction. E) Line A5, showing a series of HR reactions occurring directly below powdery mildew hyphae. F) Line A25, showing a chain of HR reactions directly below a hypha which was more visible in a different plane of view.

FIG. 9 shows representative microscopic images of leaf tissue innoculated with powdery mildew for the plants described in Example 4: A) Pl2.1 A25 line, youngest leaves (leaf 1-20) with no spores visible. B) Royal Gala control micrografted line showing abundant hyphal growth on 'Royal Gala' untransformed youngest leaves (leaf 1-20). C) Pl2.1 DA4 deletion line, youngest leaves (leaf 1-20) with no spores visible.

EXAMPLES

The invention will now be illustrated with reference to the following non-limiting example.

Example 1

Isolation of the Powdery Mildew Resistance Gene of the Invention

Plant Material and Population Assessments

Three segregating families were used for the mapping analysis presented below. Two of these families (S2 and S9) have the same parents (the susceptible variety 'Royal Gala' crossed with the powdery mildew resistant clone A689-24) but were derived from seed generated in subsequent years (1993 and 1994).

The powdery mildew phenotype of each individual of the populations was assessed after the seedlings had been transplanted into the orchard for 2 to 6 years. Each year powdery mildew growth on the progeny was scored using a 5 point scale where 0 represents no visible symptoms of powdery mildew growth (resistant or escape plant) and 5 represents abundant powdery mildew growth (susceptible plant). An average score over the years was used to test segregation of the gene for goodness of fit with the model of a single major gene.

It is difficult to assign progeny with intermediate scores (between 1 and 2) to their appropriate resistance class since the field based assessment of mildew resistance suffers from some problems [10, 20]. Therefore we modified the suggestion of Dunemann et al. [10] that scores of 0 or 1 indicate resistance by taking an average score of less than or equal to 1 as resistant and an average score greater than 2 as susceptible, scores in between were treated as inconclusive.

According to the method of Gardiner et al. [36], a small subset of three resistant and three susceptible progeny from these 2 populations were used to generate a mini-population that could be rapidly screened by Southern hybridisation with multiple probes.

A third population ('Pinkie' X 'Braeburn') was used to confirm co-segregation of restriction fragments from 'Pinkie' since this cultivar contains the Pl2 gene and was the genomic DNA source for the large DNA insert library used below.

DNA Isolation, Primers and PCR

Genomic DNA was extracted from the parents and progeny of the above apple crosses using the Nucleon Phytopure Plant DNA extraction kit (Amersham Biosciences) and following the manufacturers instructions. Primers used for PCR were purchased from Invitrogen Corporation (Carlsbad, Calif. USA). The name and sequence of the primers used was as follows; Pl2.1 specific SNP primers; R2 P2N (SEQ ID NO:9) (the mismatched site is underlined) 5' TCATAATTTACCGGCTTTCCTG 3', F2 P2N (SEQ ID NO:10) 5' TCTGATGACTTC GATGTTGAA 3', 2NA probe primers; F1-2NA (SEQ ID NO:11) 5' CACCA-CAAAAAGAGGCAGT G 3' R1-2NA (SEQ ID NO:12) 5' CATTGCTGGTCGATTTGATG 3'. The reaction conditions and sequence of the SCAR primers were based on published protocols as follows; S5 [19] and NZscOPU02, OPN18, NZscOPAC16/OPAZ16 [16]. The specific SNP marker used the same conditions specified for marker NZscOPU02 with the PCR reaction containing 1% formamide. The PCR programme used consisted of an initial denaturing step of 94° C. for 4 min followed by 30 cycles of 94° C. for 30 s, 52° C. for 30 s and 72° C. for 30 s and a final extension step of 72° C. for 5 min. Two sets of Pl2.1 specific primers that together span the entire Pl2.1 open reading frame were used in reverse transcriptase (RT)-PCR reactions to assess if the entire Pl2.1 transcript (and therefore the entire Pl2.1 gene) is present in the transformants. Set 1 amplifies the region from just outside the initiating methionine to the 3' end of the coiled coil domain and set 2 amplifies from the 3' end of the coiled coil region to the beginning of 3' UTR. The name and sequence of these primers pairs is: set 1—Pl2.1 5' utr F1 (SEQ ID NO:13) (GCGATTCGGTCTTTCTTTGA) and Pl2.1 3' CCR1 (SEQ ID NO:14) (CTACACCAAAATT-GACGGCATCTGT); set 2—Pl2.1 5' CCF1 (SEQ ID NO:15) (CAAAAAAATACGAGCATACAGATGCC) and Pl2.1 3' utr R1 (SEQ ID NO:16) (AAAACATTCCTC-GACAGATGA). The RT-PCR reactions consisted of 2 uL of diluted cDNAs in a 20 uL reaction volume using Platinum Taq polymerase (Invitrogen, Carlsbad). The following PCR programme was used: an initial denaturation cycle at 94° C. for 4 min; followed by 20 touchdown cycles of 94° C. for 30s, 65° C. to 55° C. (0.5° C. decrease at each cycle) for 30s, 72° C. for 30s; followed by 10 cycles at 94° C. for 30s, 55° C. for 30s and 72° C. for 30s, and a final extension at 72° C. for 5 min. Transcript expression analysis was performed with the transformants and control in the following way. Quantitative real time (qRT)-PCR reactions were set up and consisted of 5 uL of diluted cDNAs used in 20 uL reaction volume in an AB17700 Real time PCR machine following the manufacturers instructions (ABI, Foster City, USA). A Pl2.1-specific primer pair was used to amplify a 135 by Pl2.1-specific PCR product. The PCR programme used was as follows; 10 min at 95° C., followed by a 40 cycles of a two step PCR consisting of 95° C. for 15s and 60° C. for 1 min. The name of the primers used is Pl2.1rt 5' F1 (SEQ ID NO:17) (sequence AGGAATCGCGAAGT CTACCA) and Pl2.1 3' CCR1 (sequence given above); A pair of primers that amplify an apple actin gene were used as the internal control. The same PCR conditions and reaction set up was used for this internal control. The name and sequence of the primers used are ACT2F (SEQ ID NO:18) (GCAGAGCGT-GAAATTGTGAG) and ACT2R (SEQ ID NO:19) (ATGAC-CTGCCCATCTGGTAA).

Southern Blot Analysis, RFLP Mapping PCR Mapping and Linkage Analysis:

Restriction digests were performed according to the manufacturers instructions and Southern blotting was performed according to the method of Sambrook et al. [35]. The same technique was used to generate blots of mini-populations for rapid screening and blots containing the entire progeny set from populations S2, S9 and 'Pinkie' X 'Braeburn'. The size of RFLPs was estimated by scanning lumi-grams with the geldoc (BioRad) system and using labeled marker lanes to estimate the size of the hybridising bands. A number of existing SCAR markers that are known to be closely linked to the Pl2 resistance gene based on previous analysis [16] were also included in the mapping analysis and 456 progeny were scored for the closest known flanking markers (N18 and NZscOPU2 SCAR). In one case sequence data from the Pl2.1 candidate gene and an NBS gene sequence database developed previously by the applicants (data not shown) was used to develop a PCR-based single nucleotide polymorphism test that was used to accurately place a candidate gene onto the Pl2 genetic map. This test used the primers R2P2N and F2 P2N given above and the R2

P2N primer contained a deliberate mismatch following the method of Drenkard et al. [9]. As gene conversion events can interfere with the ordering of markers that are close together, fine scale ordering of markers was based on progeny containing recombination events that were diagnostic for marker order and using that information to develop the most parsimonious marker order.

Screening of a Cosmid Library from 'Pinkie'

A 7n haploid equivalent cosmid library (SuperCos 1168, 960 clones) generated by Sau3AI partial digestion of genomic DNA from the resistant cv 'Pinkie' was screened with the NBS clone that revealed RFLPs linked to powdery mildew resistance. One duplicate copy of the cosmid library was used to generate 6 copies of a high density (3×3) array of 384 well plates on Hybond N+ membranes using the 384 pin HDR tool of the Biomek 2000 by the following method. Hybond N+ membranes were overlayed on LB agar omnitray plates containing 75 ml of solidified LB agar medium. The culture medium from four 384 well microtitre plates was subsequently inoculated in duplicate spots onto a single Hybond membrane (with one of the nine available positions being left empty). These plates were then grown at 37° C. overnight and the membranes were removed and processed by a colony hybridisation method [35]. Hybridisation was carried out by using ECL labeled insert DNA and following the manufacturers instructions (MD Biosciences, Zurich) for probing and stringent washing conditions.

Screening of NBS Clones to Identify RFLPs Segregating with Powdery Mildew Resistance The applicants previously constructed a phylogenetic tree from the NBS regions of putative apple resistance gene analogue clones that were isolated by PCR (data not shown). Representatives from the main branches of this phylogenetic tree were screened across mini-population blots by Southern hybridisation in order to search for restriction fragment length polymorphisms (RFLPs) that putatively segregate with the powdery mildew resistance phenotype. Clones that generated RFLPs putatively linked to the powdery mildew resistance gene Pl2 were then screened across an enlarged population to test if the co-segregation with phenotype remained consistent.

RNA Extraction and cDNA Cloning

RNA was extracted from 'Pinkie' by the method of Chang et al. [7]. DNA sequence data from the putative 3' untranslated region of a homologous ESTs with a high degree of sequence identity to Pl2.1 was used to identify a GC clamp next to the poly A region that was used to reverse transcribe RNA of 'Pinkie'. DNA sequence data generated from the resistance gene candidate Pl2.1 was used to design 2 specific cDNA primers; (SEQ ID NO:20) 3'UTR (sequence 5' CTTGACCCAAACCAAAATATG 3') and 5'UTR (SEQ ID NO:21) (5' TTGACTGTTGATCTTCCCTTC 3'). These primers were used to amplify cDNA copies of the gene from reverse transcribed RNA of 'Pinkie'. The following PCR programme was used to amplify candidate cDNAs that match the DNA sequence of Pl2.1; 4 min at 95° C., followed by a 30 cycles of a three step PCR consisting of 95° C. for 30s, 55° C. for 30s and 68° C. for 90s. The reaction concentrations were 0.2 uM for dNTPs and 2 uM of each primer and amplification was driven by 2 units of the Expand DNA Polymerase (Roche) system in a final reaction volume of 50 ul.

RNA was extracted from transformants using 100 mg of leaf tissues with the RNeasy Plant Mini Kit (Qiagen, Hilden, Germany). Then 500 ng of total RNAs were used to make first-strand cDNA using SuperScriptII (Invitrogen, Carlsbad, USA). The synthesised cDNA was diluted 10-fold in TE buffer and stored at −20° C. until further use for RT-PCR and qRT-PCR analysis of the transformants.

DNA Sequencing and Sequence Analysis

DNA sequencing reactions (using universal forward, reverse or custom designed primers for primer walking reactions) were performed by a cycle sequencing method according to manufacturers instructions using ABI Big dye terminator sequencing mix (Applied Biosystems, Foster City, Calif.) and analysed on an ABI PRISM™377-XL or ABI3100 genetic analyser sequencers. The results from the DNA sequencer were analysed using ABI PRISM™ DNA sequencing analysis software version 3.0 (Applied Biosystems, Foster City, Calif.). Base calling was performed by the semiadaptive base calling method and the resulting files were imported into Sequencher™ 3.0 (Genecodes Corp., Ann Arbor, Mich.) where the sequences from forward, reverse and primer walking reactions for the same clone were aligned and manually checked and edited. In the case of the resistance gene analogue Pl2.1 all of the sequences (including 3 independently cloned cDNA copies, 5' and 3' sequences) were joined together into a single project to identify putative start and stop sites, the open reading frame and any putative introns/exons.

Progeny and Orchard Based Powdery Mildew Phenotype Analysis

Progeny were screened with 6 microsatellite markers and 12 progeny were identified as having a marker profile that was inconsistent with being derived from a cross between 'Royal Gala' and A689-24A689-24. These progeny were eliminated from further consideration. The remaining progeny of the S2 and S9 crosses were analysed for mildew resistance in the field over several growing seasons from 1998 to 2002 and classified as resistant (scoring an average of 1 or less), susceptible (scoring an average of 2 or greater) or inconclusive. The phenotype score of the majority of the 443 progeny putatively placed them into either the resistant or susceptible classes (198 resistant versus 221 susceptible). Taking marker data into consideration, the resistant and susceptible classes showed 97% and 96% concordance respectively between the anticipated phenotype based on marker profile and the observed phenotype in the orchard. By deduction there is a high probability that the linked Pl2 allele is identical by descent (IBD) amongst (but not between) each of these two classes. Based on this interpretation, powdery mildew resistance segregated in a simple 1:1 ratio (Probability Chi squared=0.26) in this population suggesting that the gene might be amenable to being cloned by map-based techniques. The remaining 24 progeny were treated as inconclusive scoring an average between 1 and 2. Genetic marker data analysis of these progeny confirmed that these scores generated the greatest degree of discordance between marker profile and observed phenotype. It indicated that 10 of these progeny showed alleles IBD from the chromosome carrying the resistance allele of Pl2 and 14 showed alleles IBD from the chromosome carrying the susceptible allele of Pl2.

Mapping Strategy and Identification of an RGA that Co-Segregates with Resistance The 443 progeny of the S2 and S9 populations were genotyped and scored for the presence or absence of the flanking OPN18 and NZscOPU02 SCAR markers. Progeny from these populations were also screened with a number of nucleotide binding site domain fragments isolated previously by PCR (data not shown). Given that a large database of NBS sequences had been developed a process needed to be developed to prioritise the clones to be mapped. We based this process on the position of NBS sequences on a phylogenetic tree. Fourteen NBS clones were chosen from main branches of a phylogenetic tree constructed (data not shown). These were screened by hybridisation across Southern blots of genomic DNA digested with EcoRV and DraI containing a small exploratory set of resistant and susceptible progeny and the two parents of crosses S2 and S9 (mini-population).

One of these original 14 clones, mf1c9, showed a possible co-segregation pattern of polymorphic restriction fragments with powdery mildew resistance in the mini-population (FIG. 1). Two RFLP fragments in each of two different restriction endonuclease digests (4.9 kb and 4.7 kb EcoRV fragments and 5.7 kb and 5.5 kb DraI fragments) were present in the resistant progeny and absent from the susceptible progeny. A series of 11 to 13 restriction fragments were revealed with this probe, suggesting the presence of a large gene family of homologous resistance gene candidates. A high rate of co-segregation of the EcoRV RFLPs with the resistance phenotype and their absence in susceptible progeny (93% concordance) was confirmed by the analysis of an enlarged dataset of 150 phenotyped individuals using Southern blots of genomic DNA. Almost complete concordance between the presence or absence of both of the OPN18 and NZscOPU02 SCAR markers and the presence or absence of these two RFLPs was found. Just one individual exhibited the RFLP fragments but lacked both the OPN18 and NZscOPU02 SCAR markers.

Figure 2A:
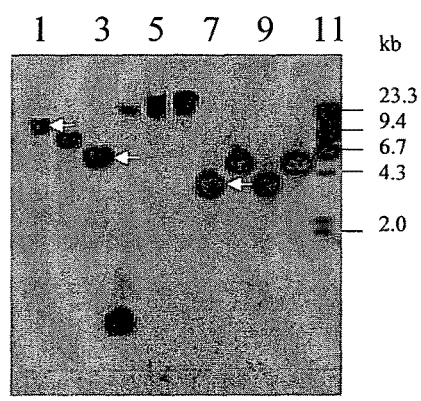
Figure 2B:
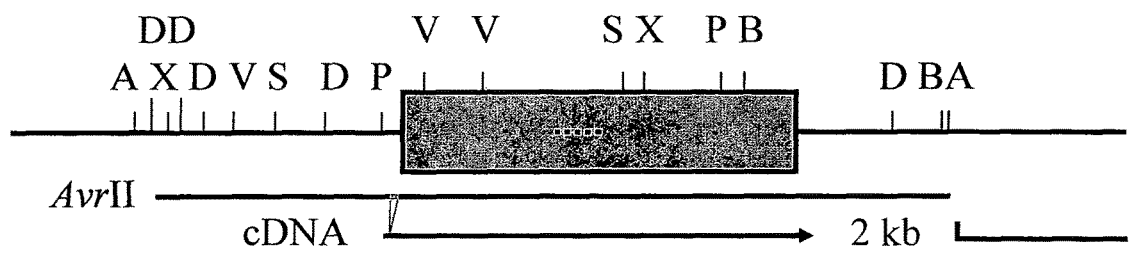

Screening the Pinkie Cosmid Library and Sequencing of a $Pl_2$ Candidate Gene Region The mf1c9 clone was used as a hybridisation probe to screen the cosmid library for candidate genes homologous to the probe in order to be able to correlate the segregation patterns of specific RFLPs with a specific gene candidate. The screen with mf1c9 identified two positive clones Pk4-051-2N and Pk4-051-4F. Restriction mapping and hybridisation analysis of these clones identified that both contained a 5.7 kb DraI restriction fragment that is the same size as one of the RFLPs above that putatively co-segregates with the powdery mildew resistance phenotype and is therefore a candidate for the Pl2 resistance gene. The two cosmids showed identical restriction endonuclease profiles and the results for Pk4-051-2N are shown in FIG. 2A. Analysis of Pk4-051-2N identified restriction fragments of convenient size for sub-cloning that hybridised to the probe mf1c9 which were selected as initial sub-cloning targets (9 kb ApaI—lane 1, 5.7 kb DraI—lane 3 and 3.6 kb SpeI—lane 7). Initial blast searches with sequence information from these clones suggested the presence of at least one open reading frame with homology to the known tomato wilt (*Fusarium oxysporum*) disease resistance gene I2 [37]. Further restriction enzyme analyses of the cosmid clones (not presented) were used to identify sub-cloning strategies for regions near the gene not contained in these initial clones (AvrII, SacI). These fragment were cloned and sequenced and a restriction map derived from this sequence information is shown in FIG. 2B. The complete DNA sequence of the AvrII fragment and its deduced amino acid translation is shown in FIG. 3.

Figure 4A:
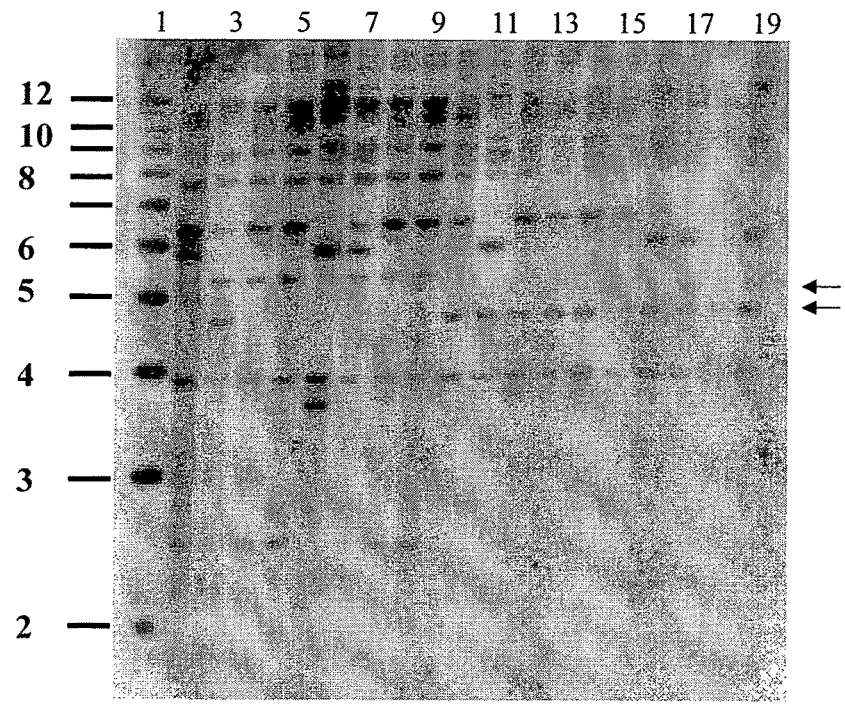
Figure 4B:
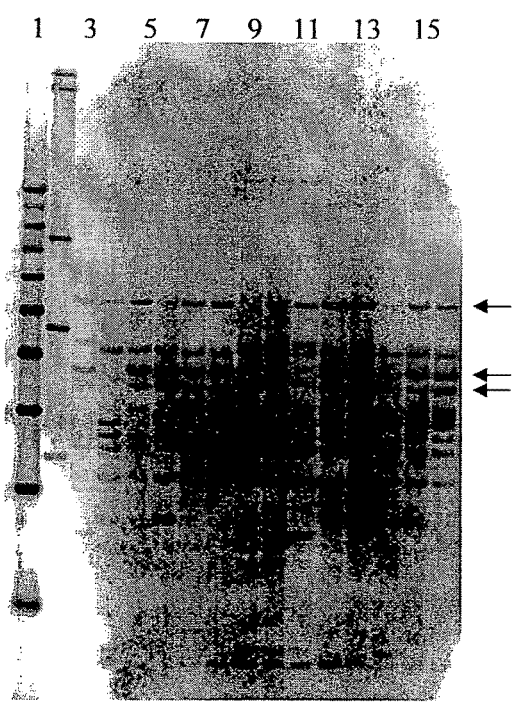

PCR Based Mapping and RFLP Mapping with the 2NA Fragment from Candidate Gene $Pl_{2.1}$ A fragment from the middle of the candidate gene clone (2NA, position shown in FIG. 2B.) was used as a probe for further RFLP mapping of this candidate gene and other candidate genes able to hybridise to this fragment. This region of the gene showed 43% identity at the protein level over 133 residues to a region identified by Simons et al. [37] as a leucine rich region containing a potential leucine zipper domain within the tomato I2 gene. Genomic DNA of parents and progeny of the S2 and S9 populations was digested with restriction endonuclease EcoRV and polymorphic RFLPs segregating in these populations were analysed by Southern blotting and hybridization with the 2NA probe (FIG. 4A). This data was added to the data derived from the powdery mildew phenotype scores and SCAR mapping data. The two polymorphic RFLPs scored (4.9 kb and 4.7 kb fragments) showed almost perfect co-segregation with the set of flanking markers surrounding the resistance gene. A similar RFLP analysis to investigate co-segregation of DraI RFLPs was also carried out in the population 'Pinkie' X 'Braeburn' (FIG. 4B.). This indicated that three RFLPs including the 5.7 kb and 5.5 kb DraI fragments and a third 6.2 kb DraI fragment co-segregate, we named the gene represented by the 5.7 kb RFLP Pl2.1 whereas the 5.5 kb and 6.2 kb fragments represent additional candidate genes for the Pl2 mediated resistance.

Figure 5A:
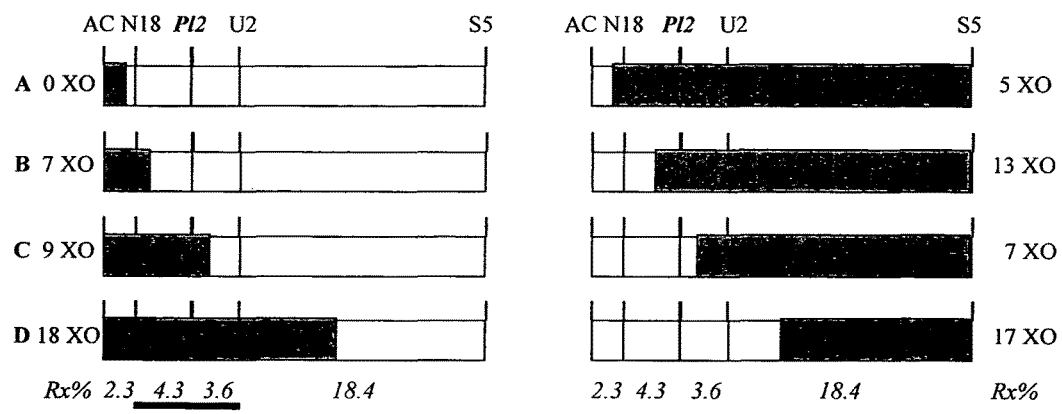
Figure 5B:
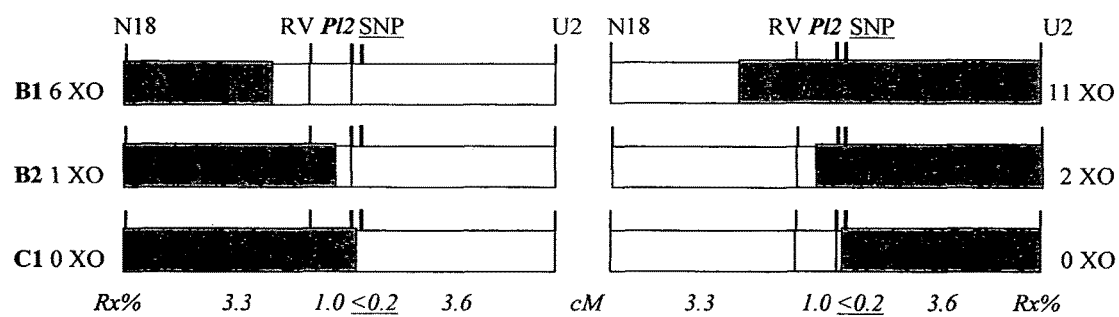

A PCR based SNP marker likely to be specific to the Pl2.1 candidate gene (5.7 kb DraI fragment) was designed based on the sequences of the NBS region of the gene. The polymorphic site was identified by comparing this sequence with our large database of other apple NBS sequences. This marker was screened over the entire S2 and S9 populations and this marker data together with RFLP marker data (where the markers could be confidently scored) were integrated into a genetic map. Flanking markers were previously ordered with respect to each other and the resistance phenotype by JoinMap [16] while the most parsimonious order of the closer (resistance candidate gene based) markers to the resistance phenotype was determined by choosing the order that required invoking the smallest number of double cross-over or gene conversion events possible. This allowed us to identify likely gene conversion events. The resulting gene order and the deduced number and location of meiotic cross-over events are shown in FIG. 5. Based on this analysis only 3 putative cross-over events were found between the Pl2 candidate gene represented by the EcoRV fragments and the resistance phenotype and no cross-over events were detected between the 5.7 kb DraI fragment of Pl2.1, the Pl2.1 SNP marker and the resistance phenotype.

Among the progeny showing no recombination events near the Pl2 locus there were ten progeny (five resistant and 5 susceptible) where the phenotype of the progeny did not match the anticipated phenotype based on IBD. Progeny like this have been labeled Genotype-Phenotype Incongruence (GPI) progeny and sometimes excluded from particular analyses to determine the exact position of resistance genes [12, 18]. These progeny can be interpreted in several possible ways as either gene conversion events (in which case changes in any candidate gene would be expected but not necessarily always detectable by the marker display methods used), a double cross-over event between the closest flanking markers on either side and the resistance gene, or a progeny where the resistance phenotype has not fully penetrated. Lack of penetration of the resistance phenotype could be because of other factors segregating in the background of the progeny, due to the biology of the pathogen, or a combination of quantitative factors coming together to give resistance in the absence of a major resistance gene. Evidence for gene conversion at one of the markers around the gene was found amongst four of the five resistant progeny. These GPI progeny could give misleading evidence against associations between candidate genes and their phenotypic effects, as it is not possible to distinguish between many of these possibilities and only some of them would eliminate candidate genes from contention for being responsible for the Pl2 mediated resistance.

Only the recombinations which are likely to be due to meiotic cross-over events were therefore considered useful to eliminate candidate genes from contention. Such cross-over events should have evidence of recombination in the flanking markers as well as possibly some of the closer gene markers not derived from the gene(s) primarily responsible for the Pl2 powdery mildew resistance phenotype. Considering only such recombination events, we could not detect any cross-over events between the Pl2.1 candidate gene and the resistance phenotype. Therefore the analysis was consistent with the Pl2.1 candidate gene being responsible for the powdery mildew resistance phenotype of the Pl2 locus. The sequence of the full-length Pl2.1 protein is shown in SEQ ID NO: 1. The sequence of the Pl2.1 gene is shown in SEQ ID NO: 2. The sequence of the open reading frame/cDNA encoding Pl2.1 is shown in SEQ ID NO: 3.

Gene constructs containing the Pl2.1 coding region and up and downstream regulatory regions were introduced into a plant transformation vector in order to assay gene function by transformation.

Example 2

Characterisation of the Pl2.1 Protein and Comparison with Other CC-NBS-LRR Known Resistance Genes Similarity with other known resistance genes can be used to indicate the presence of a series of protein domains required to impart an ability to confer resistance. BlastP searches with the deduced protein sequences of the $Pl_{2.1}$ candidate gene identified a number of genes from other species, including three known resistance genes, I2 from tomato [37], Pm3b from wheat [42] and Xa1 from rice [44], as the closest matches. The Q9LRR4 gene from *Arabidopsis*, with similarity to the known resistance gene RPP13, is the closest match in *Arabidopsis* (FIG. 6A).

The highest degree of identity was in the NBS region where Q9LRR4 was the closest match at 46% identity followed by I2 (42% identity), PM3b and Xa1 (34% and 33% identity respectively).

Lower levels of identity were found between the proteins encoded by these genes in the CC region (32%, 25% and 18% for Q9LRR4, I2 and PM3b respectively), whereas Xa1 contained a much longer N terminal region which was difficult to align with the other 3 proteins.

In the LRR region the I2 protein was the most similar to $Pl_{2.1}$ at 28% identity.

Figure 6C:
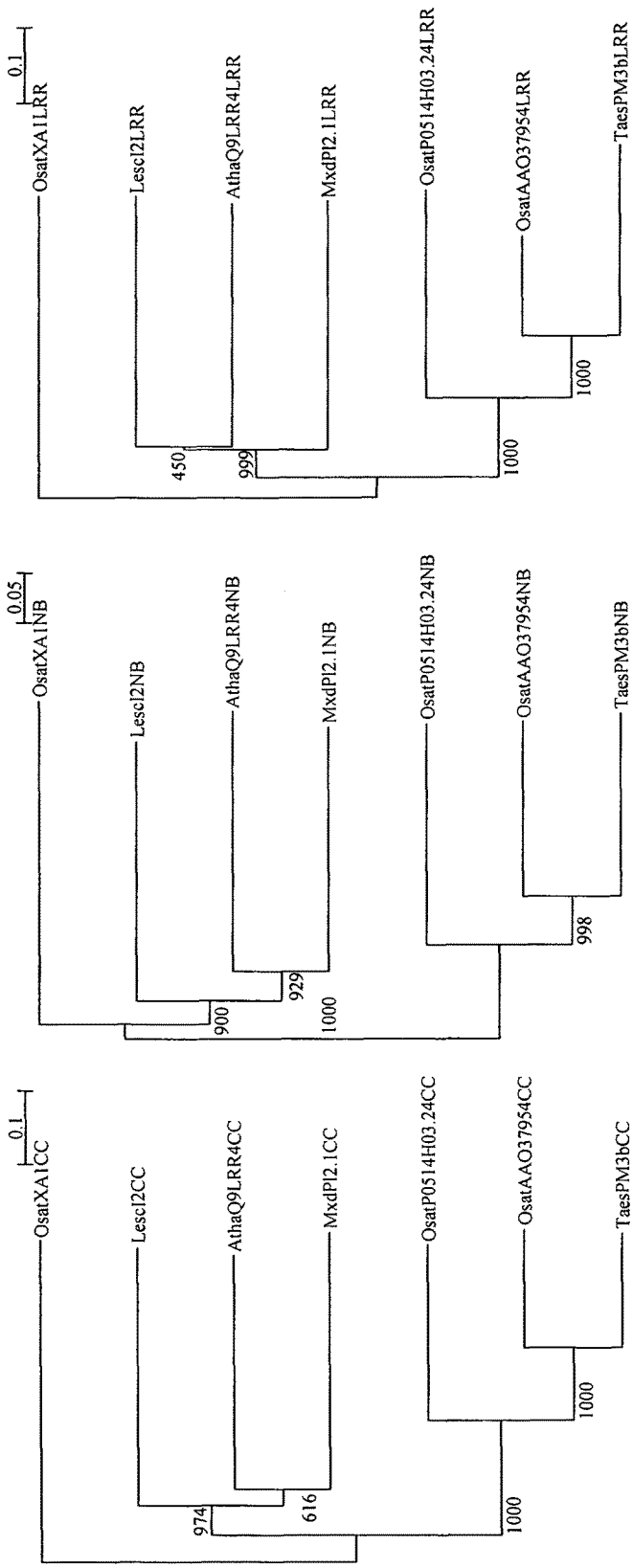

Phylogenetic trees drawn from these alignments show a similar relationship between the proteins regardless of the region of the alignment used to draw the tree (FIG. 6C). The trees and alignments also contain sequences from two rice proteins (identified by their accession numbers AAO37954 and P0514H03.24) that have previously been shown [42] to fall into a common clade with the wheat PM3b protein.

Example 3

Use of Polynucleotides of the Invention Encoding the Full Length Pl2.1 Protein to Confer Powdery Mildew Resistance Plant Transformation Vector Constructs, Transformation and Transcription Analysis An 8.5 kb AvrII fragment containing the entire putative open reading frame of the resistance gene candidate Pl2.1 and 4.4 kb of adjacent sequence (2.8 kb at the 5' end and 1.6 kb at the 3' end) was cloned into the plant transformation binary vector pART27 [17] to generate the vector pPl2.1-clone10. This pPl2.1-clone10 was introduced into *Agrobacterium tumefaciens* strain LBA4404 and kanamycin resistant transformants of apple were selected using plant transformation protocols previously described by Yao et al. [43]. Putative transformants were analysed by PCR to determine whether the entire Pl2.1 gene was introduced and transcription of the gene was analysed by qRT PCR according to the method of Zhang et al. [45].

Functional Analysis of Pl2.1 Transformants

Twenty-five independent transformed lines of 'Royal Gala' were generated by transformation with the pPl2.1-clone10 construct. Single shoots regenerated from each callus were separated and multiplied by subculturing to derive multiple copies of 25 independent lines. Shoots of each copy of each independent line were rooted and transferred into the glass house for growing under controlled conditions.

To test for the presence of an intact Pl2.1 transgene a small leaf was removed from each of the putative transformed plants at an early stage of growth and both DNA and RNA isolated from this leaf for subsequent PCR based analysis. RT-PCR analysis using two sets of Pl2.1-specific primer pairs suggested all transformants tested (a total of 8 lines) had full-length Pl2.1 transcripts. qRT-PCR analysis showed that there was a varying degree of Pl2.1 transcript level in these lines. Table 1 shows a difference of up to 9-fold among the 11 independently transformed lines that were tested. The level of Pl2.1 transcripts detected in Royal Gala was so low that it is not statistically significant above background.

TABLE 1 qPCR of transformants

| Transformant line | Average Expression | Standard Deviation |
|---|---|---|
| A2 | 0.32 | 0.068 |
| A4 | 0.35 | 0.023 |
| A6 | 0.65 | 0.036 |
| A7 | 0.30 | 0.034 |
| A8 | 0.39 | 0.037 |
| A10 | 0.34 | 0.036 |
| A14 | 1.97 | 0.111 |
| A15 | 0.22 | 0.032 |
| A18 | 0.45 | 0.009 |
| A19 | 1.06 | 0.024 |
| A25 | 0.64 | 0.063 |
| Control | 0.01 | 0.005 |

Table 1. Quantitative PCR (qPCR) of 11 independently transformed lines carrying the Pl2.1 gene. The relative expression level of 11 independent lines was assessed using the primer pair Pl2.1rt 5' F1 and Pl2.1 3' CCR1 and compared with an Actin internal control (using primers ACT2F and ACT2R) and an untransformed Royal Gala control. Values are given as ratios relative to expression of the Actin gene in each sample which was set arbitrarily at 1.0. Standard deviations were calculated based on the analysis which was done in triplicate.

Representatives of the transformed plants and control plants were introduced into a glasshouse in order to test the effect of the candidate gene on the powdery mildew phenotype of the normally susceptible 'Royal Gala' host.

A minimum of three copies of 9 independent lines were generated and introduced into the glasshouse together with control untransformed 'Royal Gala'. The challenge was initiated by introducing 'Royal Gala' plants heavily infected with powdery mildew and the infection process on the uninfected control and transgenic plants was followed over a period of several months at the macroscopic symptom level.

In the first season in the glasshouse macroscopic symptoms were recorded by visual inspection and estimating the proportion of the top 20 leaves heavily infected with mildew. At the end of the first season plants were pruned down to a 50 cm height and treated with Hicane to induce uniform budbreak [14].

The results of monitoring the macroscopic symptoms of these plants during the first spring-summer season are presented in Table 2.

TABLE 2

Macroscopic phenotypic scoring of transformants

| Line | Description | Months after challenge | | |
|---|---|---|---|---|
| | | 1 | 2 | 6 |
| 'Royal Gala' A2 | Pl2.1 Transformant | 0*[1] | 0 | 0 |
| 'Royal Gala' A3 | Pl2.1 Transformant | 0 | 0 | 0 |
| 'Royal Gala' A4 | Pl2.1 Transformant | 0 | 0 | 0 |
| 'Royal Gala' A5 | Pl2.1 Transformant | 0 | 0 | 0*[2] |
| 'Royal Gala' A7 | Pl2.1 Transformant | 0 | 0 | 0 |
| 'Royal Gala' A8 | Pl2.1 Transformant | 0 | 0 | 0 |
| 'Royal Gala' A10 | Pl2.1 Transformant | 0 | 0 | 0 |
| 'Royal Gala' A24 | Pl2.1 Transformant | 0 | 0 | 0*[2] |
| 'Royal Gala' A25 | Pl2.1 Transformant | 0 | 0 | 0 |
| 'Royal Gala' | Untransformed | 53 ± 15%*[3] | 82% ± 8%*[3] | 93% ± 3%*[3] |

Table 2. Powdery mildew phenotypes of 9 independent transformed lines of 'Royal Gala' with the Pl2.1 gene in the first year in the glasshouse. Plants were maintained in triplicate in a glasshouse into which heavily infected mildew plants were introduced and the infection of transgenic and susceptible control plants was followed over 6 months. 0*[1] clear, no visible symptoms on any leaves, *[2]some fungal growth just visible to the naked eye *[3]proportion (percentage) of the top 20 leaves infected with visible symptoms over an average of 3 plants scored (standard deviation).

Examples of the appearance of these plants are illustrated in FIG. 7 (panels A and B). Macroscopic powdery mildew infection symptoms appeared consistently on the untransformed control plants and appeared on most of their leaves over time. In contrast no macroscopic symptoms could be detected on any of the lines transformed with the Pl21 gene in this first year of infection.

Microscopic symptoms of infection on Pl2.1 transgenic plants were too difficult to detect on a regular basis in order to be able to assess the response of the host when it carries the candidate gene.

The plants were maintained in the glasshouse over winter and treated with Hicane in the spring to induce budbreak. A natural infection cycle was allowed to initiate infection in the second season in the glasshouse. The infections were followed by regular macroscopic observations of the plants. Susceptible control plants again rapidly became infected with powdery mildew. Three months into the second season a detailed microscopic analysis of the response of the plants was carried out by inspecting several leaves from each plant proceeding from the youngest to the oldest leaf to determine if there were any spores or hyphae present, whether these spores germinated or the hyphae attempted to penetrate the host and the range of responses of the control and transgenic plants to powdery mildew. Example of the response of the control and Pl2.1 transgenic plants to powdery mildew spores detected by monitoring the microscopic symptoms during this second period of infection are presented in FIG. 7 (panels C to E) and FIG. 8.

On the control plants the leaves were usually covered with dense growth of powdery mildew hyphae over a period of a few weeks (FIG. 7C). In contrast the transgenic plants containing the Pl2.1 gene contained few or no spores on the youngest leaves (FIG. 7D). A few spores could be detected on middle aged leaves (FIG. 7E), but in most cases these spores were not germinating (FIG. 7F).

This initially made it difficult to detect whether the plants responded with a hypersensitive reaction to attempts by the spores to penetrate the host. A more detailed examination some of the older leaves from the transgenic plants (FIG. 8) did however reveal increasing numbers of germinating powdery mildew spores and hyphae, albeit that this growth was always much slower and at a much lower level than found on the susceptible controls.

Even on the older leaves there were still many ungerminated spores visible and no obvious response from the host was visible in most fields of view (FIG. 8A). However some of the hyphae on these plants were closely associated with a response that has the hallmarks of a hypersensitive response (HR), as illustrated in FIG. 8B to 8F.

Two of the nine lines eventually showed some signs of fungal growth that were just visible to the naked eye (lines A5 and A24), but even these were clearly distinguishable from the control plants which were heavily infected by this stage.

These observations were consistent between the replicates of the individual transformed and control lines. At the microscopic level all of the lines examined which contained the Pl2.1 gene showed HR-like reactions. In many cases several HR reactions could be found in a single field of view and usually some signs of hyphal growth could be found adjacent or right above these reactions when focusing the microscope on different planes of view. The range of HR reactions is displayed in FIG. 8. This data suggests that the Pl2.1 gene is responsible for at least a major part of the resistance response (if not the entire response) conferred by the Pl2 powdery mildew resistance locus and operates, at least in part, by the mechanism of a hypersensitive response.

SUMMARY

A targeted map-based cloning strategy has been used in apple to identify a gene for the $Pl_2$ locus that co-segregates with the $Pl_2$ resistance phenotype. This candidate gene, named $Pl_{2.1}$, has been fully sequenced, consists of a continuous open reading frame of over 1300 amino acids and has all of the hallmark domains of a plant disease resistance gene in the coiled-coil, nucleotide binding site domain, leucine-rich repeat (CC-NBS-LRR) class. When this gene was transformed into susceptible apple plants they showed an enhanced resistance to mildew in glasshouse trials associated with hypersensitive response reactions. This allele of the $Pl_{2.1}$ locus therefore confers powdery mildew resistance in apple. This finding constitutes the first plant resistance gene in the NBS class cloned from the Rosaceae for which a function has been confirmed and the first powdery mildew resistance gene cloned within the Rosaceae.

Example 4

Expression of a Truncated Pl2.1 Protein, Including Only a Coiled-Coil and a Nucleotide Binding Site Domain, Confers Powdery Mildew Resistance in Transgenic Plants The applicants also prepared a Pl2.1 deletion construct that would express a truncated Pl2.1 protein. Two XmnI restriction sites identified in FIG. 3 were used to excise a 1.4 kb fragment from the Pl2.1 gene while retaining its original promoter and terminator sequences. In addition to excising the 1.4 kb fragment, the excision results in most of the remaining leucine rich repeat region being out of frame with the N terminal portion of the Pl2.1 gene. FIG. 6B shows where these deletion events occur within the leucine rich repeat region. Plants carrying this modified construct would thus express a protein with only the first two domains (the coiled-coil and nucleotide binding site domains) intact. This allowed the applicants to test if the first two domain are sufficient to provide resistance. The sequence of the Pl2.1 deletion construct is shown in SEQ ID NO: 4. The sequence of the truncated Pl2.1 protein, expressed by the construct of SEQ ID NO: 4, is shown in SEQ ID NO: 5. The cDNA sequence encoding the truncated Pl2.1 protein is shown in SEQ ID NO: 7. The sequence of a truncated Pl2.1 protein extending from the full-length N-terminus to the end of the NBS domain is shown in SEQ ID NO: 6. The cDNA encoding the polypeptide of SEQ ID NO: 6 is shown in SEQ ID NO: 8.

The Pl2.1 deletion construct was cloned into pART27, introduced into *A. tumefaciens* strain LBA4404 and used to transform apple as described in Example 3.

Functional Analysis of Pl2.1 Deletion and Full-Length Pl2.1 Transformants

Further testing was carried out in the glasshouse in the third season to assess the effect of grafting and to compare symptom development on transgenic plants carrying a complete open reading frame of Pl2.1 with plants carrying a deletion allele of Pl2.1 and missing more than half of the protein in the correct reading frame. Five of the Pl2.1 plant lines tested in Example 3 (lines A3, A5 A7 A8 and A25) were used to prepare plants for testing using the simple test of bench-grafting onto Royal Gala stock plants, and five plant lines carrying a Pl2.1 deletion allele (lines DA2, DA3, DA4 DA5 and DA6) were used to prepare plants for testing using the simple test of micro-grafting onto Royal Gala stock plants to create a suitable comparison between these two types of lines and the bench-grafted (line B) and micro-grafted (line M) control lines. The results of monitoring the macroscopic symptoms of these plants during the third spring-summer season are presented in Table 3. Examples of the microscopic appearance of these plants are illustrated in FIG. 9 (panels A, B and C). Microscopic powdery mildew infection symptoms appeared consistently on the grafted untransformed control lines and appeared on most of their leaves over time. In contrast no microscopic symptoms could be detected on any of the grafted transformant lines carrying the complete Pl2.1 gene. This illustrates that grafting is a simple test that can speed up the analysis of testing for the function of genes of this nature. In addition no microscopic symptoms could be detected on any of the grafted transformant lines carrying the Pl2.1 deletion allele. This illustrates that the Pl2.1 protein sustaining large deletions of more than half of the Pl2.1 gene can still provide functional resistance. This also provides strong evidence that proteins including only the first two domains are sufficient to provide the resistance function.

TABLE 3

Phenotypic comparison of transformants with PL2.1 full length or deletion allele

| Line (clones) | Description | Days after challenge 40 | 60 |
|---|---|---|---|
| Royal Gala A3 (2) | Pl2.1 Transformant | 0 | 0 |
| Royal Gala A5 (2) | Pl2.1 Transformant | 0 | 0 |
| Royal Gala A7 (1) | Pl2.1 Transformant | 0 | 0 |
| Royal Gala A8 (1) | Pl2.1 Transformant | 0 | 0 |
| Royal Gala A25 (2) | Pl2.1 Transformant | 0 | 0 |
| Royal Gala B (3) | Bench-graft controls | 60 | 90 |
| Royal Gala DA2 (5) | Pl2.1 deletion allele | 0 | 0 |
| Royal Gala DA3 (2) | Pl2.1 deletion allele | 0 | 0 |
| Royal Gala DA4 (5) | Pl2.1 deletion allele | 0 | 0 |
| Royal Gala DA5 (3) | Pl2.1 deletion allele | 0 | 0 |
| Royal Gala DA6 (1) | Pl2.1 deletion allele | 0 | 0 |
| Royal Gala M (5) | Micro-graft controls | 60 | 90 |

Table 3. Powdery mildew phenotypes of 5 independent transformed lines of 'Royal Gala' with the full length Pl2.1 gene and 5 independent transformed lines with the Pl2.1 deletion allele in the third year in the glasshouse. Transformed shoots were used as micrografts onto M9 rootstocks. When the shoots were approximately 30 cm in length, the shoots were cut back and single node cuttings were grafted on to Royal Gala stock plants. Full length Pl2.1 transformants were bench grafted whereas transformants carrying the Pl2.1 deletion allele were micro-grafted. Royal Gala control plants were bench-grafted and micro-grafted at the same time. These plants were grown for a further three months, then exposed to powdery mildew spores and the infection of transgenic and untransformed plants was followed over 2 months. The resulting phenotypes were scored as for Table 2.

REFERENCES

1. Belfanti E, Silfverberg-Dilworth E, Tartarini S, Patocchi A, Barbieri M, Zhu J, Vinatzer B A, Gianfranceschi L, Gessler C, Sansavini S: The HcrVf2 gene from a wild apple confers scab resistance to a transgenic cultivated variety. Proceedings of the National Academy of Sciences of the United States of America 101: 886-890 (2004).
2. Bent A F, Kunkel B N, Dahlbeck D, Brown K L, Schmidt R, Giraudat J, Leung J, Staskawicz B J: Rps2 of *Arabidopsis thaliana*: a leucine-rich repeat class of plant disease resistance genes: Science Washington 265: 1856-1860 (1994).
3. Braun T, Schofield P R, Sprengel R: Amino-terminal leucine rich repeats in gonadotrophin receptors determine hormone selectivity. EMBO J. 10: 1885-1890 (1991).
4. Brueggeman R, Rostoks N, Kudrna D, Kolian A, Han F, Chen J, Druka A, Steffenson B, Kleinhofs A: The barley stem rust-resistance gene Rpg1 is a novel disease-resistance gene with homology to receptor kinases. Proc Natl Acad Sci USA 99: 9328-9333 (2002).
5. Buschges R, Hollricher K, Panstruga R, Simons G, Wolter M, Frijters A, Daelen Rv, Lee Tvd, Diergaarde P, Groenendijk J, Topsch S, Vos P, Salamini F, Schulze Lefert P, Van Daelen R, Van der Lee T: The barley Mlo gene: a novel control element of plant pathogen resistance. Cell Cambridge 88: 695-705 (1997).
6. Cai D, Kleine M, Kifle S, Harloff H J, Sandal N N, Marcker K A, Klein-Lankhorst R M, Salentijn E, Lange W, Stiekema W J, Wyss U, Grundler F M, Jung C: Positional cloning of a gene for nematode resistance in sugar beet. Science 275: 832-4 (1997).
7. Chang S, Puryear J, Cairney J: A simple and efficient method for isolating RNA from pine trees Plant Molecular Biology Reporter 11: 113-116 (1993).
8. Dayton D F: Genetic immunity to apple incited by *Podpshaera leucotricha*. HortScience 12: 225-226 (1977).
9. Drenkard E, Richter B G, Rozen S, Stutius L M, Angell N A, Mindrinos M, Cho R J, Oefner P J, Davis R W, Ausubel F M: A simple precedure for the analysis of single nucleotide polymorphisms facilitates map-based cloning in *Arabidopsis*. Plant physiol Md: 1926-(2000).
10. Dunemann F, Bracker G, Markussen T, Roche P, Tobutt K R, Alston F H: Identification of molecular markers for the major mildew resistance gene Pl$_2$ in apple. Acta Horticulturae 484: 411-416 (1999).
11. Durel C E, Laurens F, Fouillet A, Lespinasse Y: Utilization of pedigree information to estimate genetic parameters from large unbalanced data sets in apple. Theor. Appl Genet. 96: 1077-1085 (1998).
12. Erdin N, Tartarini S, Broggini G A L, Gennari F, al e: Mapping of the apple scab-resistance gene Vb. Genome 49: 1238 (2006).
13. Fischer C, Schmidt H, Kellerhals M: Breeding apple cultivars with multiple resistance. Progress in temperate fruit breeding Wadenswil-Einsiedeln: Switzerland, 30 Aug. to 3 Sep., 1993. 1994, 43-48 (1994).
14. Fuchigami L H, Nee C-C: Degree growth stage model and rest-breaking mechnaisms in temperate woody perennials. HortScience 22: 836-845 (1987).
15. Gallott J C, Lamb R C, Aldwinckle H S: Resistance to powdery mildew from some small-fruited *Malus* cultivars. Hortscience 20: 1085-1087 (1985).
16. Gardiner S, Murdoch J, Meech S, Rusholme R, Bassett H, Cook M, Bus V, Rikkerink E, Gleave A, Crowhurst R, Ross G, Warrington I: Candidate resistance genes from an EST database prove a rich source of markers for major genes conferring resistance to important apple pests and diseases. Acta Horticulturae: 141-151 (2003).
17. Gleave A P: A versatile binary vector system with a T-DNA organisational structure conducive to efficient integration of cloned DNA into the plant genome. Plant Molecular Biology 20: 1203-1207 (1992).
18. Gygax M, Gianfranceschi L, Liebhard R, Kellerhals M, Gessler C, Patocchi A: Molecular markers linked to the apple scab resistance gene Vbj derived from *Malus baccata jackii*. Theoretical and Applied Genetics 109: 1702-1717 (2004).
19. Hemmat M, Weeden N F, Aldwinckle H S, Brown S K: Molecular markers for the scab resistance (Vf) region in apple. Journal of the American Society of Horticultural Science 123: 992-996 (1998).
20. Jame J, Verhaegh J J, den Nijs A P M: Early selection for partial resistance to powdery mildew, *Podosphaera leucotricha* (Ell. et Ev.) Salm. in apple progenies. Euphytica 77: 7-9 (1994).
21. Jones D A, Jones J D G: The role of leucine-rich repeat proteins in plant defences. Adv. Bot. Res. Adv. Plant Pathol., pp. 89-167 (1997).
22. Jones D A, Thomas C M, Hammond Kosack K E, Balint Kurd P J, Jones J D G: Isolation of the tomato Cf-9 gene for resistance to *Cladosporium fulvum* by transposon tagging. Science Washington 266: 789-793 (1994).
23. Kawchuk L M, Hachey J, Lynch D R, Kulcsar F, van Rooijen G, Waterer D R, Robertson A, Kokko E, Byers R, Howard R J, Fischer R, Prüfer D: Tomato Ve disease resistance genes encode cell surface-like receptors. Proc. Nat. Acad. Sci. 98: 6511-6515 (2001).
24. Knight R L, Alston F H: Sources of field immunity to mildew (*Podosphaera leucotricha*). Can J Genet Cytol. 10: 294-298 (1968).
25. Korban S S, Dayton D F: Evaluation of *Malus* germplasm for resistance to powdery mildew. HortScience 18: 219-220 (1983).
26. Kruger J: Breeding for mildew resistance in apples at Ahrensburg: sources and stability. Gartenbauwissenschaft 60: 269-275 (1995).
27. Lespinasse Y, Rousselle Bourgeois F, Rousselle P: Breeding apple tree: aims and methods. Proceedings of the Joint Conference of the EAPR Breeding & Varietal Assessment Section and the EUCARPIA Potato Section France: 12-17 Jan. 1992. 1992, 103-110 (1992).
28. Liu J, Liu X, Dai L, Wang G: Recent Progress in Elucidating the Structure, Function and Evolution of Disease Resistance Genes in Plants. Journal of Genetics and Genomics 34: 765-776 (2007).
29. Markussen T, Kruger J, Schmidt H, Dunemann F: Identification of PCR-based markers linked to the powdery-mildew-resistance gene Pl$_1$ from *Malus* robusta in cultivated apple. Plant Breeding 114: 530-534 (1995).
30. Martin G B, Frary A, Wu T Y, Brommonschenkel S, Chunwongse J, Earle E D, Tanksley S D: A member of the tomato Pto gene family confers sensitivity to fenthion resulting in rapid cell death. Plant Cell 6: 1543-1552 (1994).
31. Nicholas K B, Nicholas H B J, Deerfield D W I: Gene-doc: Analysis and visualization of genetic variation. EMBNEW. NEWS 4: 14 (1997).
32. Perrière G, Gouy M: WWW-Query: An on-line retrieval system for biological sequence banks. Biochimie 78: 364-369 (1996).
33. Riely B K, Martin G B: Ancient origin of pathogen recognition specificity conferred by the tomato disease resistance gene Pto. Proc Natl Acad Sci USA 98: 2059-2064 (2001).
34. Rosebrock T R, Zeng L R, Brady J J, Abramovitch R B, Xiao F M, Martin G B: A bacterial E3 ubiquitin ligase targets a host protein kinase to disrupt plant immunity. Nature (London) 448: 370-374 (2007).
35. Sambrook J, Fritsch E F, Maniatis T: Molecular cloning: a laboratory manual. Cold Spring Harbor Laboratory Press; Cold Spring Harbor, N.Y.; USA (1989).
36. Scotti P D, Dearing S C, PRESENT RBJRA: A simple technique to distinguish between two species of the mussel genus *Perna*. New Zealand Journal of Marine and Freshwater Research (2005).
37. Simons G, Groenendijk J, Wijbrandi J, Reijans M, Groenen J, Diergaarde P, Van der Lee T, Bleeker M, Onstenk J, de Both M, Haring M, Mes Cornelissen B, Zabeau M, Vos P: Dissection of the *Fusarium* I2 Gene Cluster in Tomato Reveals Six Homologs and One Active Gene Copy. Plant Cell 10: 1055-1068 (1998).
38. Song W, Wang G, Chen L, Kim H, Pi L, Holsten T, Gardner J, Wang B, Zhai W, Zhu L, Fauquet C, Ronald P, Song W Y, Wang G L, Chen L L, Kim H S, Pi L Y, Wang B, Zhai W X, Zhu L H: A receptor kinase-like protein encoded by the rice disease resistance gene, Xa21. Science Washington 270: 1804-1806 (1995).
39. Thompson J D, Gibson T J, Plewniak F, Jeanmougin F, Higgins D G: The ClustalX windows interface: flexible strategies for multiple sequence alignment aided by quality analysis tools. Nucleic Acids Research 24: 4876-4882 (1997).
40. Visser T, Verhaegh J J: Resistance to powdery mildew (*Podosphaera leucotricha*) of apple seedlings growing under glasshouse and nursery conditions. Proc Eucarpia Meeting of Fruit Tree Breeding, Angers: pp 111-120 (1979).
41. Whitham S, Dinesh Kumar S P, Choi D, Hehl R, Con C, Baker B: The product of the tobacco mosaic virus resistance gene N: similarity to Toll and the interleukin-1 receptor. Cell Cambridge 78: 1101-1115 (1994).
42. Yahiaoui N, Srichumpa P, Dudler R, Keller B: Genome analysis at different ploidy levels allows cloning of the powdery mildew resistance gene Pm3b from hexaploid wheat. Plant Journal 37: 528-538 (2004).

43. Yao J L, Cohen D, Atkinson R, Richardson K, Morris B: Regeneration of transgenic plants from the commercial apple cultivar Royal Gala. Plant Cell Reporter 14: 407-412 (1995).
44. Yoshimura S, Yamanouchi U, Katayose Y, Toki S, Wang Z X, Kono I, Kurata N, Yano M, Iwata N, Sasaki T: Expression of Xal, a bacterial blight-resistance gene in rice, is induced by bacterial inoculation. Proc. Natl. Acad. Sci. U.S.A. 95: 1663-1668 (1998).
45. Zhang B, Chen K, Bowen J, Allan A, Espley R, Karunairetnam S, Ferguson I: Differential expression within the LOX gene family in ripening kiwifruit. J. Exp. Bot. 57: 3825-3836 (2006).

| SEQ ID NO: | Sequence type | Information | Species |
|---|---|---|---|
| 1 | polypeptide | full-length Pl2.1 protein | Malus zumi |
| 2 | polynucleotide | Pl2.1 gene | Malus zumi |
| 3 | polynucleotide | open reading frame/cDNA encoding full-length Pl2.1 protein | Malus zumi |
| 4 | polynucleotide | Pl2.1 deletion construct for expessing truncated Pl2.1 protein of SEQ ID NO: 5 | Malus zumi |
| 5 | polypeptide | truncated Pl2.1 protein | Malus zumi |
| 6 | polypeptide | fragment containing CC domain and NBS domain only of Pl2.1 protein | Malus zumi |
| 7 | polynucleotide | cDNA encoding truncated Pl2.1 protein of SEQ ID NO: 5 | Artificial |
| 8 | polynucleotide | cDNA encoding truncated Pl2.1 protein of SEQ ID NO: 6 | Artificial |
| 9 | polynucleotide | R2 P2N primer | Artificial |
| 10 | polynucleotide | F2 P2N primer | Artificial |
| 11 | polynucleotide | F1 2NA probe primer | Artificial |
| 12 | polynucleotide | R1 2NA probe primer | Artificial |
| 13 | polynucleotide | 1-Pl2.1 5' utr F1 primer | Artificial |
| 14 | polynucleotide | Pl2.1 3' CCR1 primer | Artificial |
| 15 | polynucleotide | Pl2.1 5' CCF1 primer | Artificial |
| 16 | polynucleotide | Pl2.1 3' utr R1 primer | Artificial |
| 17 | polynucleotide | Pl2.1rt 5' F1 primer | Artificial |
| 18 | polynucleotide | ACT2F primer | Artificial |
| 19 | polynucleotide | ACT2R primer | Artificial |
| 20 | polynucleotide | cDNA primer 3'UTR | Artificial |
| 21 | polynucleotide | cDNA primer 5'UTR | Artificial |

The invention claimed is:

1. A host cell, plant cell, plant, plant part or plant propagule, that contains a transgene comprising a polynucleotide encoding a polypeptide, said polypeptide comprising a sequence with at least 98% identity to the amino acid sequence of at least one of:
   a) SEQ ID NO: 1,
   b) SEQ ID NO: 5, and
   c) SEQ ID NO: 6;
wherein the polypeptide confers resistance to the powdery mildew fungus *Podosphaera leucotricha* in a Rosaceae plant.

2. The host cell, plant cell, plant, plant part, or plant propagule, of claim 1, wherein the polypeptide comprises the amino acid sequence of at least one of:
   a) SEQ ID NO: 1,
   b) SEQ ID NO: 5, and
   c) SEQ ID NO: 6.

3. The host cell, plant cell, plant, plant part, or plant propagule, of claim 1 wherein the polypeptide comprises the amino acid sequence of SEQ ID NO: 1.

4. The host cell, plant cell, plant, plant part, or plant propagule, of claim 1 wherein the polypeptide comprises the amino acid sequence of SEQ ID NO: 5.

5. The host cell, plant cell, plant, plant part, or plant propagule, of claim 1 wherein the polypeptide comprises the amino acid sequence of SEQ ID NO: 6.

6. The host cell, plant cell, plant, plant part, or plant propagule, of claim 1, wherein the polynucleotide comprises the sequence with at least 95% identity to at least one of:
   a) SEQ ID NO: 2,
   b) SEQ ID NO: 3,
   c) SEQ ID NO: 7, and
   d) SEQ ID NO: 8.

7. The host cell, plant cell, plant, plant part, or plant propagule, of claim 1, wherein the polynucleotide comprises the sequence of at least one of:
   a) SEQ ID NO: 2,
   b) SEQ ID NO: 3,
   c) SEQ ID NO: 7, and
   d) SEQ ID NO: 8.

8. An expression construct comprising a promoter operably linked to a polynucleotide encoding a polypeptide, said polypeptide comprising a sequence with at least 98% identity to the amino acid sequence of at least one of:
   a) SEQ ID NO: 1
   b) SEQ ID NO: 5, and
   c) SEQ ID NO: 6;
wherein the polypeptide confers resistance to the powdery mildew fungus *Podosphaera leucotricha* in a Rosaceae plant, and wherein the promoter is heterologous to the polynucleotide.

9. A host cell, plant cell, plant, plant part, or plant propagule, comprising the expression construct of claim 8.

10. A method for producing a plant cell or plant with increased resistance to powdery mildew, the method comprising transforming a plant cell or plant with a polynucleotide encoding a polypeptide, said polypeptide comprising a sequence with at least 98% identity to the amino acid sequence of at least one of:
    a) SEQ ID NO: 1,
    b) SEQ ID NO: 5, and
    c) SEQ ID NO: 6;
wherein the polypeptide confers resistance to the powdery mildew fungus *Podosphaera leucotricha* in a Rosaceae plant.

11. The method of claim 10, wherein the polynucleotide is part of an expression construct.

12. A method for producing a progeny of the plant of claim 1 with increased resistance to powdery mildew, the method comprising at least one of:
    a) breeding using the plant as a male or female parent to produce the progeny plant, and
    b) asexually reproducing the plant to produce the progeny plant;
wherein the progeny plant contains the transgene.

13. A method for producing a plant cell or plant with increased resistance to powdery mildew, the method comprising transformation of a plant cell or plant comprising a polynucleotide encoding a polypeptide, said polypeptide comprising a sequence with at least 95% identity to the amino acid sequence of at least one of:
    a) SEQ ID NO: 1,
    b) SEQ ID NO: 5, and
    c) SEQ ID NO: 6;
wherein the polypeptide confers resistance to the powdery mildew fungus *Podosphaera leucotricha* in a Rosaceae plant.

14. A method for producing a polypeptide conferring resistance to powdery mildew, the method comprising expressing in a plant cell or plant a polynucleotide encoding a polypeptide, said polypeptide comprising a sequence with at least 95% identity to the amino acid sequence of at least one of:
    a) SEQ ID NO: 1,
    b) SEQ ID NO: 5, and
    c) SEQ ID NO: 6;
wherein the polypeptide confers resistance to the powdery mildew fungus *Podosphaera leucotricha* in a Rosaceae plant.

* * * * *